(12) United States Patent
Jackson et al.

(10) Patent No.: US 11,993,640 B2
(45) Date of Patent: May 28, 2024

(54) TREATING INFLAMMATORY LUNG DISEASE

(71) Applicants: United States Government as represented by the Department of Veterans Affairs, Washington, DC (US); University of Miami, Miami, FL (US)

(72) Inventors: Robert M. Jackson, Miami, FL (US); Andrew V. Schally, Miami Beach, FL (US); Renzhi Cai, Miami, FL (US)

(73) Assignee: The United States Government as Represented by the Department of Veterans Affairs, Washington, DC (US)

(*) Notice: Subject to any disclaimer, the term of this patent is extended or adjusted under 35 U.S.C. 154(b) by 201 days.

(21) Appl. No.: 17/396,577

(22) Filed: Aug. 6, 2021

(65) Prior Publication Data

US 2022/0000983 A1 Jan. 6, 2022

Related U.S. Application Data

(63) Continuation of application No. PCT/US2020/017375, filed on Feb. 8, 2020.

(60) Provisional application No. 62/869,687, filed on Jul. 2, 2019, provisional application No. 62/803,170, filed on Feb. 8, 2019.

(51) Int. Cl.
| | | |
|---|---|---|
| *A61K 38/25* | (2006.01) | |
| *A61P 11/00* | (2006.01) | |
| *A61P 35/00* | (2006.01) | |
| *C07K 14/60* | (2006.01) | |
| *A61K 38/00* | (2006.01) | |

(52) U.S. Cl.
CPC ............ *C07K 14/60* (2013.01); *A61K 38/25* (2013.01); *A61P 11/00* (2018.01); *A61P 35/00* (2018.01); *A61K 38/00* (2013.01)

(58) Field of Classification Search
CPC ........ C07K 14/60; A61K 38/25; A61K 38/00; A61P 11/00; A61P 35/00
See application file for complete search history.

(56) References Cited

U.S. PATENT DOCUMENTS

| | | | |
|---|---|---|---|
| 4,659,693 | A | 4/1987 | Nester |
| 4,914,189 | A | 4/1990 | Schally et al. |
| 5,084,555 | A | 1/1992 | Coy et al. |
| 5,550,212 | A | 8/1996 | Zarandi et al. |
| 5,942,489 | A | 8/1999 | Schally et al. |
| 6,057,422 | A | 5/2000 | Schally et al. |
| 6,124,263 | A | 9/2000 | Muccioli et al. |
| 7,452,865 | B2 | 11/2008 | Schally et al. |
| 8,227,405 | B2 | 7/2012 | Schally et al. |
| 8,227,421 | B2 | 7/2012 | Schally et al. |
| 8,691,942 | B2 | 4/2014 | Schally et al. |
| 9,260,504 | B2 | 2/2016 | Schally et al. |
| 2007/0042950 | A1 | 2/2007 | Schally et al. |
| 2011/0066230 | A1 | 3/2011 | Schally et al. |
| 2013/0261055 | A1 | 10/2013 | Schally et al. |
| 2014/0206836 | A1 | 7/2014 | Schally et al. |
| 2015/0166617 | A1 | 6/2015 | Schally et al. |
| 2017/0202907 | A1* | 7/2017 | Romero-Lucas ...... A61K 38/16 |
| 2018/0250358 | A1 | 9/2018 | Schally et al. |
| 2019/0300590 | A1 | 10/2019 | Bhandari |
| 2021/0395327 | A1 | 12/2021 | Jackson et al. |

FOREIGN PATENT DOCUMENTS

| | | | |
|---|---|---|---|
| CA | 2733440 | 2/2010 | |
| CN | 1326353 A | 12/2001 | |
| CN | 102170864 | 8/2011 | |
| EP | 2222272 | 11/2012 | |
| EP | 2478011 | 8/2014 | |
| WO | 9116923 | 11/1991 | |
| WO | 9742223 | 11/1997 | |
| WO | 0031136 | 6/2000 | |
| WO | 2005016953 | 2/2005 | |
| WO | 2005113822 | 12/2005 | |
| WO | 2009/120831 | 10/2009 | |
| WO | 2009120831 | 10/2009 | |
| WO | WO-2009120831 A2 * | 10/2009 | ............ A61K 38/25 |
| WO | 2010015818 | 2/2010 | |
| WO | 2011034976 | 3/2011 | |
| WO | 2014004934 | 1/2014 | |
| WO | 2019060601 | 3/2019 | |
| WO | 2020163833 | 8/2020 | |
| WO | 2021011874 | 1/2021 | |
| WO | 2021222129 | 11/2021 | |

OTHER PUBLICATIONS

Cleveland Clinic, Pulmonary Fibrosis, https://my.clevelandclinic.org/health/diseases/10959-pulmonary-fibrosis#symptoms-and-causes, accessed online Jul. 13, 2023.*
Rutherford, Robert et al.: "Mycobacteria in Pathogenesis of Sarcoidosis," Chest., 2004; 125(1):354.
Fang, Chuling, et al.: "Immunological Evidence for the Role of Mycobacteria in Sarcoidosis: A Meta-Analysis," PLOS ONE, 2016, No. 10:1-14.
Iannuzzi, Michael C. et al.: "Sarcoidosis," The New England Journal of Medicine, 2007, No. 357:2153-2165.
Barabutis, Nektarios et al: "Antioxidant activity of growth hormone-releasing hormone antagonists in LNCaP human prostate cancer line," PNAS, Dec. 2008, vol. 105, No. 51:20470-20475.
Baughman, Robert P. et al: "A retrospective pilot study examining the use of Acthar gel in sarcoidosis patients," Respiratory Medicine, 2016, vol. 110:66-72.

(Continued)

*Primary Examiner* — Julie Ha
*Assistant Examiner* — Erinne R Dabkowski
(74) *Attorney, Agent, or Firm* — Stanley A. Kim

(57) ABSTRACT

Described herein are compositions and methods for treating pulmonary fibrosis and cancer. The compositions include growth hormone releasing hormone peptides. The methods include reducing lung inflammation, lung scarring, reducing expression of T cell receptor complex genes as well as inhibiting tumor growth.

4 Claims, 17 Drawing Sheets

Specification includes a Sequence Listing.

(56) References Cited

OTHER PUBLICATIONS

Baughman, Robert P. et al: "Clinical characteristics of patients in a case control study of sarcoidosis," Am J Respir Crit Care Med, 2001, vol. 164:1885-1889.

Brownell, Isaac et al: "Evidence for mycobacteria in sarcoidosis," Am J Respir Cell Mol Biol, 2011, vol. 45:899-905.

Auerbach, Robert et al: "Angiogenesis assays: Problems and pitfalls," Cancer and Metastasis Review, 2000, vol. 19:167-172.

Cervini, Laura A. et al:"Human Growth Hormone-Releasing Hormone hGHRH(1-29)-NH2: Systematic Structure-Activity Relationship Studies," J. Med. Chem, 1998, vol. 41: 717-727.

Dermer, Gerald B.: "Another Anniversary for the War on Cancer," Biotechnology, 1994, vol. 12: 320.

Gura, Trisha: "Systems for Identifying New Drugs are Often Faulty," Science, 1997, vol. 278, Issue 5340: 1041-1042.

Halmos, Gabor et al.: "Human renal cell carcinoma expresses distinct binding sites for growth hormone-releasing hormone," PNAS, Sep. 2000, vol. 97, No. 19: 10555-10560.

Jaffe, Craig A. et al.: "Suppression of growth hormone (GH) hypersecretion due to Ectopic GH-releasing hormne (GHRH) by a selective GHRH antagonist," Journal of Clinical Endocrinology and Metabolism, 1996, vol. 82, No. 2: 634-637.

Jain, Rakesh K. et al: "Quantitative angiogenesis assays: Progress and problems," Nature Medicine, 1997, vol. 3, No. 11: 1203-1208.

Kiaris, Hippokratis et al: "Expression of a splice variant of the receptor for GHRH in 3T3 fibroblasts activates cell proliferation responses to GHRH analogs," PNAS, Jan. 2002, vol. 99, No. 1: 196-200.

Klukovits, Anna et al.: "Novel antagonists of growth hormone-releasing hormone inhibit growth and vascularization of human experimental ovarian cancers," Cancer, 2012: 670-680.

Etsch, Markus et a.: "Growth hormone-releasing hormone (GHRH) antagonists inhibit the proliferation of androgen-dependent and-independent prostate cancers," PNAS, Feb. 2003, vol. 100, No. 3: 1250-1255.

Merrifield, R.B.: Solid phase peptide synthesis. I. The synthesis of a tetrapeptide, Syntheisis of a Tetrapeptide, Jul. 1963, vol. 85: 2149-2154.

Perez, Roberto et al.: "Antagonists of growth hormone-releasing hormone suppress in vivo tumor growth and gene expression in triple negative breast cancers," Oncotarget, 2012, vol. 3: 988-997.

Plonowski, Artur et al.: "Inhibition of proliferation of PC-3 human prostrate cancer by antagonists of growth hormone-releasing hormone: Lack of correlation with the levels of serum IGF-I and expression of Tumoral IGF-II and vascular endothelial growth factor, " The Prostrate, 2002, vol. 52: 173-182.

Pozsgai, Eva et al.: "The effect of GHRH antagonists on human glioblastomas and their mechanism of action," Int. J. Cancer, 2010, vol. 127: 2313-2322.

Pozsgai, Eva et al.: "The effect of a novel antagonist of growth hormone releasing hormone on cell proliferation and on the key cell signaling pathways in nine different breast cancer cell lines," Int Journal of Oncology, 2011, vol. 39: 1025-1032.

Rekasi, Zoltan et al.: "Antagonists of growth hormone-releasing hormone and vasoactive intestinal peptide inhibit tumor proliferation by different mechanisms: Evidence from in vitro studies on human prostatic and pancreatic cancers," Endocrinology, 2000, vol. 141, No. 6: 2120-2128.

Rekasi, Zoltan et al.: "Islolation and sequencing of cDNAs for splice variants of growth hormone-releasing hormone receptors from human cancers," PNAS, Sep. 2000, vol. 97, No. 19: 10561-10566.

Schally, Andrew V. et al.: "Antagonistic analogs of growth hormone-releasing hormone: New potential antitumor agents," TEM, 1999, vol. 10, No. 10: 383-391.

Schally, Andrew V. et al.: "Hypothalamic hormones and cancer," Frontiers in Neuroendocrinology, 2002, vol. 22: 248-291.

Schally, Andrew V. et al.: "Antagonists of growth hormone-releasing hormone in oncology," Combinatorial Chemistry & High Throughput Screening, 2006, vol. 9: 163-170.

Siejka, A. et al.: "GH-RH antagonist (MZ-4-71) inhibits VEGF secretion and proliferation of murine endothelial cells," Life Sciences, 2003, vol. 72: 2473-2479.

Szepeshazi, Karoly et al.: "Antagonists of GHRH decrease production of GH and IGF-I in MXT mouse mammary cancers and inhibit tumor growth," Endocrinology, 2001, vol. 14: 4371-4378.

Szereday, Zoltan et al.: "Antagonists of growth hormone-releasing hormone inhibit the proliferation of experimental non-small cell lung carcinoma," Cancer Research, 2003, vol. 63: 7913-7919.

Toth, Katalin et al.: "New analogs of human growth hormone-releasing hormone (1-29) with high and prolonged antagonistic activity," J. Peptide Res., 1998, vol. 51: 134-141.

Varga, Jozsef L. et al.: "Synthesis and biological evaluation of antagonists of growth hormone-releasing hormone with high and protracted in vivo activities," Proc. Natl. Acad. Sci., 1999, vol. 96: 692-697.

Varga, Jozsef L. et al.: "Increased activity of antagonists of growth hormone-releasing hormone substituted at positions 8, 9, and 10," PNAS, Feb. 2004, vol. 101, No. 6: 1708-1713.

Voskoglou-Nomikos, Theodora et al.: "Clinical predictive value of the in vitro cell line, human xenograft, and mouse allograft preclinical cancer models," Clinical Cancer Research, 2003, vol. 9: 4227-4239.

Zarandi, Marta et al.: "Potent agonists of growth hormone-releasing hormone," Int. J. Peptide Protein Res., 1992, vol. 39: 211-217.

Zarandi, M. et al.: "Synthesis and biological activities of highly potent antagonists of growth hormone-releasing hormone," Proc. Natl. Acad. Sci., 1994 vol. 91: 12298-12302.

"Restenosis Treatment," web page , <https://www/news-medical.net/health/Restenosis-Treatment.aspx>, 7 pages, retrieved from website on Mar. 18, 2022.

Cabrera, Sandra et al.: "Gene expression profiles reveal molecular mechanisms involved in the progression and resolution of bleomycin-induced lung fibrosis," Am J Physiol Lung Cell Mol Physiol, 2013, vol. 304: 593-601.

Chen, Edward S. et al.: "Etiology of sarcoidosis," Clin Chest Med, 2008, vol. 29: 365-377.

Cui, Tengjiao et al.: "Agonistic analogs of growth hormone releasing hormone (GHRH) promote wound healing by stimulating the proliferation and survival of human dermal fibroblasts through ERK and AKT pathways," Aug. 2016, Oncotarget, vol. 7, No. 33: 52661-52672.

Dubaniewicz, Anna et al.: "Mycobacterium tuberculosis complex and mycobacterial heat shock proteins in lymph hode tissue from patient with pulmonary sarcoidosis," Journal of Clinical Microbiology, 2006, vol. 44, No. 9: 3448-3451.

Elhai, Muriel et al.: "OX40L blockade protects against inflammation-driven fibrosis," PNAS, Jun. 2016: E3901-E3910.

Facchetti, Fabio et al.: "Expression of Inducible nitric oxide synthase in human granulomas and histiocytic reactions," American Journal of Pathology, Jan. 1999, vol. 154, No. 1: 145-152.

Fu, Yung-Kang et al.: "A novel role of growth hormone and insulin-like growth factor-1," The Journal of Immunology, 1991 vol. 146: 1602-1608.

Havt, Alexandre et al.: "The expression of the pituitary growth hormone-releasing hormone receptor and its splice variants in normal and neoplastic human tissues," PNAS, Nov. 2005, vol. 102, No. 48: 17424-17429.

Huang, Xinqiang et al.: "Molecular characterization of a precision-cut rat lung slice model for the evaluation of antifibrotic drugs," Am J Physiol Lung Cell Mol Physiol, 2019, vol. 316: L348-L357.

Jenkins, R. Gisli et al.: "An official american thoracic society workshop report: Use of animal models for the preclinical assessment of potential therapies for pulmonary fibrosis," Am J Respir Cell Mol Biol, 2017, vol. 56, No. 5: 667-679.

Koh, Timothy J. et al.: "Inflammation and wound healing: the role of the macrophage," Expert Review in Molecular Medcine, Jul. 2011, vol. 13, e23: 1-12.

Kral, Julia Barbara et al.: "Sustained PI3K Activation exaerbates BLM-induced lung fibrosis via activation of pro-inflammatory and pro-fibrotic pathways," Scientific Reports, Mar. 2016, pp. 1-16.

(56) References Cited

OTHER PUBLICATIONS

Kucera, Gena P. et al: "Occupational risk factors for sarcoidosis in African-American siblings," CHEST, May 2003, vol. 5: 1527-1535.
Lazarus, Angeline: "Sarcoidosis: Epidemiology, etiology, pathogenesis, and genetics," DM, Nov. 2009: 649-660.
Miller, Milton A et al.: "Effect of acthar-c (ACTH) in sarcoidosis," Case Reports, Feb. 1952:776-784.
Mirsaeidi, Mehdi et al.: "Racial difference in sarcoidosis mortality in the United States," CHEST, Feb. 2015, vol. 147, No. 2: 438-449.
Jackson, Robert M. et al.: "Growth hormone-releasing hormone receptor antagonist MIA-602 modulates mouse lung inflammation and fibrosis due to bleomycin," European Respiratory journal, 2018, 52 Suppl. 62:1-2; (Only Abstract—No Full-Text Version is Available).
Qin, Yong Jie et al.: "Antagonist of GH-releasing hormone receptors alleviates experimental ocular inflammation," PNAS, Dec. 2014, vol. 111, No. 51:18303-18308.
Newman, Lee S. et al.: "A case control etiologic study of sarcoidosis," Am J Respir Crit Care Med, 2004, vol. 170: 1324-1330.
Nunes, Hilario et al.: Sarcoidosis, Orphanet Journal of Rare Diseases, 2007, vol. 2, No. 46: 1-8.
Ocampo-Lin, Blanca et al.: "Nocturnal growth hormone (GH) secretion is eliminated by infusion of GH-releasing hormone antagonist," Journal of Clinical Endocrinology and Metabolism, 1996, vol. 81, No. 12: 4396-4399.
Oswald-Richter, Kyra A. et al.: "Dual analysis for mycobacteria and propionibacteria in sarcoidosis BAL," J Clin Immunol, 2012, vol. 32: 1129-1140.
Patterson, Karen C. et al.: "Pulmonary fibrosis in sarcoidosis," Ann Am Thorac Soc, Aug. 2013, vol. 10, No. 4: 362-370.
Ren, Jia Lin et al.: "Growth hormone-releasing hormone receptor mediates cytokine production in ciliary and iris epithelial cells during LPS-induced ocular inflammation," Experimental Eye Research, 2019, vol. 181: 277-284.
Ryter Stefan W. et al.: "Mitochondrial dysfunction as a pathogenic mediator of chronic obstructive pulmonary disease and idiopathic pulmonary fibrosis," Ann Am Thorac Soc, Dec. 2018, vol. 15, Supplement 4: S266-S272.
Hung, Chi F. et al.: "Role of IGF-1 pathway in lung fibroblast activation," Respiratory Research, 2013, vol. 14: 1-.
Schally, Andrew V. et al.: "Hypothalamic and other peptide hormones," Endocrine Therapy, 2003, Section 14: 911-926.
Simonian, Philip L. et al.: "Regulatory role of γδ T cells in the recruitment of CD4+ and CD8+ T cells to lung and subsequent pulmonary fibrosis," The Journal of Immunology, 2006, vol. 177: 4436-4443.
Bellyei, Szabolcs et al.: "GHRH antagonists reduce the invasive and metastatic potential of human cancer cell lines in vitro," Cancer Letters, 2010, vol. 293: 31-40.
Warwick-Davies, Jan et al.: "Growth hormone is a human macrophage activating factor," The Journal of Immunology, 1995, vol. 154: 1909-1918.
Waters, David W. et al.: "STAT3 regulates the onset of oxidant-induced senescence in lung fibroblasts," Am J Respir Cell Mol Biol, 2019, vol. 61, Issue No. 1: 61-73.
Zarandi, Marta et al.: "Synthesis and structure-activity studies on novel analogs of human growth hormone releasing hormone (GHRH) with enhanced inhibitory activities on tumor growth," Peptides, 2017, vol. 89: 60-70.
Zhang, Chongxu et al.: "Growth hormone-releasing hormone receptor antagonist modulates lung inflammation and fibrosis due to bleomycin," Lung, 2019, vol. 197: 541-549.
Chen, Edward et al.: "Serum amyloid A regulates granulomatous inflammation in sarcoidosis through toll-like receptor-2," Am J Respir Crit Care Med, 2010, vol. 181: 360-373.
Gan, Jinfeng et al.: Growth hormone-releasing hormone receptor antagonists inhibit human gastric cancer through downregulation of PAK1-STAT3/NF-κB signaling, PNAS, 2016, vol. 113, No. 51: 14745-14550.

* cited by examiner

SEQUENCE LISTING

```
<160> NUMBER OF SEQ ID NOS: 24

<210> SEQ ID NO 1
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada, p-cePhAC, D-Phe-Ada, or
      PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
```

```
<223> OTHER INFORMATION: 5FPhe or Cpa
<220> FEATURE:
<221> NAME/KEY: MISC_FEATURE
<222> LOCATION: (8)..(8)
<223> OTHER INFORMATION: Ala or Asn
<220> FEATURE:
<221> NAME/KEY: MISC_FEATURE
<222> LOCATION: (9)..(9)
<223> OTHER INFORMATION: Arg or Har
<220> FEATURE:
<221> NAME/KEY: MISC_FEATURE
<222> LOCATION: (10)..(10)
<223> OTHER INFORMATION: Tyr(Me), Amp or 5FPhe
<220> FEATURE:
<221> NAME/KEY: MISC_FEATURE
<222> LOCATION: (11)..(11)
<223> OTHER INFORMATION: Arg or His
<220> FEATURE:
<221> NAME/KEY: MISC_FEATURE
<222> LOCATION: (12)..(12)
<223> OTHER INFORMATION: Lys or Orn
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (20)..(20)
<223> OTHER INFORMATION: Arg or His
<220> FEATURE:
<221> NAME/KEY: MISC_FEATURE
<222> LOCATION: (21)..(21)
<223> OTHER INFORMATION: Lys or Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har, Har-NH2 or Har-NHCH3
<220> FEATURE:
<221> NAME/KEY: MISC_FEATURE
<222> LOCATION: (30)..(30)
<223> OTHER INFORMATION: present or absent and, when present, is
      Ada-NH2, Ada-NHCH or Ada-NHCH2CH3

<400> SEQUENCE: 1

Tyr Arg Asp Ala Ile Xaa Thr Xaa Xaa Xaa Xaa Xaa Val Leu Xaa Gln
1               5                  10                  15

Leu Ser Ala Xaa Xaa Leu Leu Gln Asp Ile Xaa Arg Xaa Xaa
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: 5FPhe or Cpa
<220> FEATURE:
```

```
<221> NAME/KEY: MISC_FEATURE
<222> LOCATION: (8)..(8)
<223> OTHER INFORMATION: Ala or Asn
<220> FEATURE:
<221> NAME/KEY: MISC_FEATURE
<222> LOCATION: (9)..(9)
<223> OTHER INFORMATION: Har
<220> FEATURE:
<221> NAME/KEY: MISC_FEATURE
<222> LOCATION: (10)..(10)
<223> OTHER INFORMATION: Tyr(Me) or 5FPhe
<220> FEATURE:
<221> NAME/KEY: MISC_FEATURE
<222> LOCATION: (15)..(15)
<223> OTHER INFORMATION: Abu
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har or Har-NHCH3
<220> FEATURE:
<221> NAME/KEY: MISC_FEATURE
<222> LOCATION: (30)..(30)
<223> OTHER INFORMATION: Har or Har-NHCH3
<220> FEATURE:
<221> NAME/KEY: MISC_FEATURE
<222> LOCATION: (30)..(30)
<223> OTHER INFORMATION: is present or absent and, when present, is
      Ada-NH2 or Ada-NHCH3

<400> SEQUENCE: 2

Tyr Arg Asp Ala Ile Xaa Thr Xaa Xaa Xaa Arg Lys Val Leu Xaa Gln
1               5                   10                  15

Leu Ala Arg Lys Leu Leu Gln Asp Ile Xaa Arg Xaa Xaa
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: 5FPhAC-Ada is bound to Tyr
<220> FEATURE:
<221> NAME/KEY: MISC_FEATURE
<222> LOCATION: (2)..(2)
<223> OTHER INFORMATION: D-isoform
<220> FEATURE:
<221> NAME/KEY: MISC_FEATURE
<222> LOCATION: (6)..(6)
<223> OTHER INFORMATION: 5FPhe
<220> FEATURE:
<221> NAME/KEY: MISC_FEATURE
<222> LOCATION: (9)..(9)
<223> OTHER INFORMATION: homoarginine
<220> FEATURE:
<221> NAME/KEY: MOD_RES
<222> LOCATION: (10)..(10)
<223> OTHER INFORMATION: METHYLATION
<220> FEATURE:
<221> NAME/KEY: misc_feature
<222> LOCATION: (15)..(15)
```

<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (28)..(28)
<223> OTHER INFORMATION: DArg - NHCH3

<400> SEQUENCE: 3

Tyr Arg Asp Ala Ile Phe Thr Ala Xaa Tyr Arg Lys Val Leu Xaa Gln
1               5                   10                  15

Leu Ser Ala Arg Lys Leu Leu Gln Asp Ile Xaa Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: homoarginine
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

<400> SEQUENCE: 4

Tyr Arg Asp Ala Ile Xaa Thr Asn Xaa Tyr Arg Lys Val Leu Xaa Gln
1               5                   10                  15

Leu Ser Ala Arg Lys Leu Leu Gln Asp Ile Xaa Arg Xaa
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature

```
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (29)..(29)
<223> OTHER INFORMATION: Har - Ada-NH2

<400> SEQUENCE: 5

Tyr Arg Asp Ala Ile Xaa Thr Ala Xaa Tyr Arg Lys Val Leu Xaa Gln
1               5                   10                  15

Leu Ser Ala Arg Lys Leu Leu Gln Asp Ile Xaa Arg Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Homoarginine
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

<400> SEQUENCE: 6

Tyr Arg Asp Ala Ile Xaa Thr Ala Xaa Xaa Arg Lys Val Leu Xaa Gln
1               5                   10                  15
```

```
Leu Ser Ala Arg Lys Leu Leu Gln Asp Ile Xaa Arg Xaa
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Homoarginine
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Homoarginine
<220> FEATURE:
<221> NAME/KEY: MISC_FEATURE
<222> LOCATION: (29)..(29)
<223> OTHER INFORMATION: Har-NHCH3

<400> SEQUENCE: 7

Tyr Arg Asp Ala Ile Xaa Thr Ala Xaa Xaa Arg Lys Val Leu Xaa Gln
1               5                   10                  15

Leu Ser Ala Arg Lys Leu Leu Gln Asp Ile Xaa Arg Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
```

```
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Homoarginine
<220> FEATURE:
<221> NAME/KEY: MOD_RES
<222> LOCATION: (29)..(29)
<223> OTHER INFORMATION: AMIDATION

<400> SEQUENCE: 8

Tyr Arg Asp Ala Ile Xaa Thr Ala Xaa Tyr Arg Lys Val Leu Xaa Gln
1               5                   10                  15

Leu Ser Ala His Xaa Leu Leu Gln Asp Ile Xaa Arg Arg
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Homoarginine
<220> FEATURE:
<221> NAME/KEY: MOD_RES
<222> LOCATION: (29)..(29)
<223> OTHER INFORMATION: AMIDATION

<400> SEQUENCE: 9

Tyr Arg Asp Ala Ile Xaa Thr Ala Xaa Tyr Arg Lys Val Leu Xaa Gln
1               5                   10                  15

Leu Ser Ala Arg Lys Leu Leu Gln Asp Ile Xaa Arg Xaa
            20                  25
```

<210> SEQ ID NO 10
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Homoarginine
<220> FEATURE:
<221> NAME/KEY: MOD_RES
<222> LOCATION: (29)..(29)
<223> OTHER INFORMATION: AMIDATION

<400> SEQUENCE: 10

Tyr Arg Asp Ala Ile Xaa Thr Ala Arg Xaa Arg Lys Val Leu Xaa Gln
1               5                   10                  15

Leu Ser Ala His Xaa Leu Leu Gln Asp Ile Xaa Arg Xaa
            20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to D-Phe-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE

```
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Homoarginine
<220> FEATURE:
<221> NAME/KEY: MOD_RES
<222> LOCATION: (29)..(29)
<223> OTHER INFORMATION: AMIDATION

<400> SEQUENCE: 11

Tyr Arg Asp Ala Ile Xaa Thr Ala Arg Tyr Arg Lys Val Leu Xaa Gln
1               5                   10                  15

Leu Ser Ala His Xaa Leu Leu Gln Asp Ile Xaa Arg Xaa
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (10)..(10)
<223> OTHER INFORMATION: Amp
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (29)..(29)
<223> OTHER INFORMATION: Har-NHCH3

<400> SEQUENCE: 12

Tyr Arg Asp Ala Ile Xaa Thr Ala Arg Xaa Arg Lys Val Leu Xaa Gln
1               5                   10                  15

Leu Ser Ala His Xaa Leu Leu Gln Asp Ile Xaa Arg Xaa
            20                  25
```

```
<210> SEQ ID NO 13
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har-NHCH3

<400> SEQUENCE: 13

Tyr Arg Asp Ala Ile Xaa Thr Asn Arg Tyr Arg Lys Val Leu Xaa Gln
1               5                   10                  15

Leu Ser Ala Arg Lys Leu Leu Gln Asp Ile Xaa Arg Xaa
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
```

```
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Aoc-NHCH3

<400> SEQUENCE: 14

Tyr Arg Asp Ala Ile Xaa Thr Asn Xaa Tyr Arg Lys Val Leu Xaa Gln
1               5                   10                  15

Leu Ser Ala Arg Lys Leu Leu Gln Asp Ile Xaa Arg Xaa
            20                  25

<210> SEQ ID NO 15
<211> LENGTH: 29
<212> TYPE: PRT
<213> ORGANISM: Artificial Sequence
<220> FEATURE:
<223> OTHER INFORMATION: Syntthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Aoc-NHCH3

<400> SEQUENCE: 15

Tyr Arg Asp Ala Ile Xaa Thr Asn Xaa Tyr Arg Lys Val Leu Xaa Gln
1               5                   10                  15

Leu Ser Ala Arg Lys Leu Leu Gln Asp Ile Xaa Arg Xaa
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
```

```
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (12)..(12)
<223> OTHER INFORMATION: Orn
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (29)..(29)
<223> OTHER INFORMATION: Har-NHCH3

<400> SEQUENCE: 16

Tyr Arg Asp Ala Ile Xaa Thr Ala Xaa Xaa His Xaa Val Leu Xaa Gln
1               5                   10                  15

Leu Ser Ala His Xaa Leu Leu Gln Asp Ile Xaa Arg Xaa
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (12)..(12)
<223> OTHER INFORMATION: Orn
<220> FEATURE:
<221> NAME/KEY: MISC_FEATURE
```

<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NHCH3

<400> SEQUENCE: 17

Tyr Arg Asp Ala Ile Xaa Thr Ala Xaa Xaa His Xaa Val Leu Xaa Gln
1               5                   10                  15

Leu Ser Ala His Xaa Leu Leu Gln Asp Ile Xaa Arg Xaa
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (12)..(12)
<223> OTHER INFORMATION: Orn
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

```
<400> SEQUENCE: 18

Tyr Arg Asp Ala Ile Xaa Thr Ala Xaa Xaa His Xaa Val Leu Xaa Gln
1               5                   10                  15

Leu Ser Ala His Xaa Leu Leu Gln Asp Ile Xaa Arg Xaa
                20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: 5FPhe
<220> FEATURE:
<221> NAME/KEY: MISC_FEATURE
<222> LOCATION: (9)..(9)
<223> OTHER INFORMATION: Har
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (12)..(12)
<223> OTHER INFORMATION: Orn
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

<400> SEQUENCE: 19

Tyr Arg Asp Ala Ile Xaa Thr Ala Xaa Tyr His Xaa Val Leu Xaa Gln
1               5                   10                  15

Leu Ser Ala His Xaa Leu Leu Gln Asp Ile Xaa Arg Xaa
                20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
```

```
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

<400> SEQUENCE: 20

Tyr Arg Asp Ala Ile Xaa Thr Asn Arg Tyr Arg Lys Val Leu Xaa Gln
1               5                   10                  15

Leu Ser Ala His Xaa Leu Leu Gln Asp Ile Xaa Arg Xaa
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bound to 5FPhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
```

```
<223> OTHER INFORMATION: D isoform
<220> FEATURE:
<221> NAME/KEY: MISC_FEATURE
<222> LOCATION: (29)..(29)
<223> OTHER INFORMATION: Har - Ada-NH2

<400> SEQUENCE: 21

Tyr Arg Asp Ala Ile Xaa Thr Asn Arg Tyr Arg Lys Val Leu Xaa Gln
1               5                   10                  15

Leu Ser Ala His Xaa Leu Leu Gln Asp Ile Xaa Arg Xaa
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (29)..(29)
<223> OTHER INFORMATION: AMIDATION

<400> SEQUENCE: 22

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: PhAC-Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: Cpa
<220> FEATURE:
<221> NAME/KEY: MISC_FEATURE
<222> LOCATION: (9)..(9)
<223> OTHER INFORMATION: Har
<220> FEATURE:
<221> NAME/KEY: MISC_FEATURE
<222> LOCATION: (10)..(10)
<223> OTHER INFORMATION: 5FPhe
<220> FEATURE:
<221> NAME/KEY: MISC_FEATURE
<222> LOCATION: (12)..(12)
<223> OTHER INFORMATION: Orn
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (21)..(21)
<223> OTHER INFORMATION: Orn
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
```

```
<222> LOCATION: (28)..(28)
<223> OTHER INFORMATION: D isoform
<220> FEATURE:
<221> NAME/KEY: misc_feature
<222> LOCATION: (29)..(29)
<223> OTHER INFORMATION: Xaa can be any naturally occurring amino acid

<400> SEQUENCE: 23

Tyr Arg Asp Ala Ile Xaa Thr Ala Xaa Xaa His Xaa Val Leu Xaa Gln
1               5                   10                  15

Leu Ser Ala His Xaa Leu Leu Gln Asp Ile Xaa Arg Xaa
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: 5FPhAc Ada
<220> FEATURE:
<221> NAME/KEY: MISC_FEATURE
<222> LOCATION: (2)..(2)
<223> OTHER INFORMATION: D isoform
<220> FEATURE:
<221> NAME/KEY: MISC_FEATURE
<222> LOCATION: (6)..(6)
<223> OTHER INFORMATION: 5FPhe
<220> FEATURE:
<221> NAME/KEY: MISC_FEATURE
<222> LOCATION: (9)..(9)
<223> OTHER INFORMATION: homoarginine
<220> FEATURE:
<221> NAME/KEY: MOD_RES
<222> LOCATION: (10)..(10)
<223> OTHER INFORMATION: METHYLATION
<220> FEATURE:
<221> NAME/KEY: MISC_FEATURE
<222> LOCATION: (15)..(15)
<223> OTHER INFORMATION: Abu
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (28)..(28)
<223> OTHER INFORMATION: D isoform
<220> FEATURE:
<221> NAME/KEY: MISC_FEATURE
<222> LOCATION: (29)..(29)
<223> OTHER INFORMATION: homoarginine
<220> FEATURE:
<221> NAME/KEY: MISC_FEATURE
<222> LOCATION: (29)..(29)
<223> OTHER INFORMATION: bound to Ada-NH2

<400> SEQUENCE: 24

Tyr Arg Asp Ala Ile Xaa Thr Ala Arg Tyr Arg Lys Val Leu Xaa Gln
1               5                   10                  15

Leu Ser Ala Arg Lys Leu Leu Gln Asp Ile Xaa Arg Arg
            20                  25
```

TREATING INFLAMMATORY LUNG DISEASE

CROSS REFERENCE TO RELATED APPLICATIONS

This application is a continuation application under 35 U.S.C. 111(a) of international patent application number PCT/US2020/017375 filed on Feb. 8, 2020 and designated the United States, which claimed the priority of U.S. Provisional Application No. 62/803,170, filed Feb. 8, 2019, and U.S. Provisional Application No. 62/869,687, filed Jul. 2, 2019. The content of these earlier filed applications is hereby incorporated by reference herein in its entirety.

INCORPORATION OF THE SEQUENCE LISTING

The present application contains a sequence listing that is submitted via EFS-Web concurrently with the filing of this application, containing the file name "7085-0003_SL.txt" which is 24,576 bytes in size, created on Feb. 6, 2020, and is herein incorporated by reference in its entirety.

FIELD OF THE INVENTION

The present disclosure is directed to growth hormone-releasing hormone (GHRH) antagonists and the use of such antagonists for, e.g., inhibiting tumor growth, treating cancer, and/or treating pulmonary fibrosis.

BACKGROUND

Growth hormone-releasing hormone (GHRH) is a peptide belonging to the secretin/glucagon family of neuroendocrine and gastrointestinal hormones. Human GHRH (hGHRH) peptide comprises 44 amino acid residues. While the best-known site of production of GH-RH is the hypothalamus, various peripheral organs also synthesize it. hGHRH is also produced, sometimes in large quantities, by human malignant tissues (cancers) of diverse origin. GHRH exerts various physiological and pathophysiological functions. There is increasing evidence for the role of GHRH as an autocrine/paracrine growth factor in various cancers. Splice variant (SV) receptors for GHRH, different from those expressed in the pituitary, have been described in a wide range of human cancers and in some normal peripheral organs.

Pathophysiological GH secretion and IGF-1 activation have growth promoting effects in the lung, and the pituitary type GHRH receptor is present in both normal and IPF lung tissue. Idiopathic pulmonary fibrosis (IPF) is the paradigm of fibrosing interstitial lung diseases. It occurs more commonly in aging males, and often has a limited survival time of 3-5 years (median 3.8 years) after diagnosis (Lederer D, Martinez F (2018). *N Engl J Med* 378:1811-1823). Although the disease is of unknown etiology, it is clearly related to specific genetic abnormalities (e.g., MUC5B, SFTPC and others) and environmental factors (e.g., dust and smoking) (Schwartz D (2016). *Trans Am Clin Climatol Assoc* 127:34-45). In response to injury, fibroblasts proliferate and migrate into the lung. They synthesize extracellular matrix, providing a platform for further cellular growth (Herrera J, Henke C, Bitterman P (2018). *J Clin Invest* 128:45-53). Myofibroblasts secrete cytokines, such as TGF-β, with autocrine and paracrine effects that drive fibrosis in the lung (Wei Y, Kim T, Peng D, Duan D, Gibbons D, Yamauchi M, Jackson J, Le Saux C, Calhoun C, Peters J, Derynck R, Backes B, Chapman H (2017). *J Clin Invest* 127:3675-3688).

SUMMARY

Disclosed herein are peptides comprising formula I: X0-Tyr-DArg-Asp-Ala-Ile-X6-Thr-X8-X9-X10-X11-X12-Val-Leu-Abu-Gln-Leu-Ser-Ala-X20-X21-Leu-Leu-Gln-Asp-Ile-Nle-DArg-X29-X30 (SEQ ID NO: 1), wherein X0 is 5FPhAC-Ada, p-cePhAC, D-Phe-Ada, or PhAC-Ada; X6 is 5FPhe or Cpa; X8 is Ala or Asn; X9 is Arg or Har; X10 is Tyr(Me), Amp or 5FPhe; X11 is Arg or His; X12 is Lys or Orn; X20 is Arg or His; X21 is Lys or Orn; X29 is Har, Har-NH$_2$ or Har-NHCH$_3$; and X30 is present or absent and, when present, is Ada-NH$_2$, Ada-NHCH or Ada-NHCH$_2$CH$_3$, or a pharmaceutically acceptable salt thereof.

Disclosed herein are methods of treating pulmonary fibrosis, the methods comprising: administering to a subject with pulmonary fibrosis a therapeutically effective amount of a growth hormone releasing hormone (GHRH) receptor antagonist.

Disclosed herein are methods of reducing lung inflammation, the methods comprising: administering to a subject with pulmonary fibrosis a therapeutically effective amount of a growth hormone releasing hormone (GHRH) receptor antagonist.

Disclosed herein are methods of reducing lung scarring, the methods comprising: administering to a subject with pulmonary fibrosis a therapeutically effective amount of a growth hormone releasing hormone (GHRH) antagonist.

Disclosed herein are methods of ameliorating one or more symptoms of pulmonary fibrosis, the methods comprising: administering to a subject with pulmonary fibrosis a therapeutically effective amount of a growth hormone releasing hormone (GHRH) antagonist.

Disclosed herein are methods of reducing expression of one or more T cell receptor complex genes, the methods comprising administering to a subject with pulmonary fibrosis a therapeutically effective amount of a growth hormone releasing hormone (GHRH) receptor antagonist.

Disclosed herein are methods of inhibiting tumor growth, the methods comprising administering to a subject in need thereof an effective amount of a growth hormone releasing hormone (GHRH) receptor antagonist.

Other features and advantages of the present compositions and methods are illustrated in the description below, the drawings, and the claims.

BRIEF DESCRIPTION OF THE DRAWINGS

FIG. 1A is a graph showing the effect of GHRH antagonists AVR-333 (5 µg), AVR-352 (2.5 AVR-352 (5 µg), AVR-353 (2.5 µg), AVR-353 (5 µg) and AVR-353 (10 µg) compared to MIA-602 (5 µg) on tumor growth in an animal model of pancreatic cancer. Y-axis, % tumor growth; x-axis, time (weeks).

(2 µg), AVR-333 (2 µg) and AVR-540 (2 µg) compared to MIA-602 (2 µg) on tumor volume in an animal model of stomach cancer. Y-axis, % tumor growth; x-axis, time (weeks). FIG. 1N is a graph showing the effect of GHRH antagonists AVR-352 (5 AVR-353 (5 µg) and AVR-354 (5 µg) compared to MIA-602 (5 µg) on tumor growth in an animal model of prostate cancer. All statistical analyses were performed from comparing GHRH antagonists to non-treated tumor (control). P value of less than 0.05 was considered as statistically significant. (Note: *p<0.05, p<0.01. *p<0.001.)

FIG. 2A shows the inhibitory potency of various GHRH antagonists compared to MIA-602 on lung cancer cells (HCC827). FIG. 2B shows the inhibitory potency of various GHRH antagonists compared to MIA-602 on pancreatic cancer cells (CFPAC-1). FIG. 2C shows the inhibitory potency of various GHRH antagonists compared to MIA-602 on stomach cancer cells (N87). FIG. 2D shows the inhibitory potency of various GHRH antagonists compared to MIA-602 on colon cancer cells (HT29). FIG. 2E shows the inhibitory potency of various GHRH antagonists compared to MIA-602 on breast cancer cells (MX-1). FIG. 2F shows the inhibitory potency of various GHRH antagonists compared to MIA-602 on breast cancer cells (HCC1806).

FIG. 6A shows a representative mitochondrial stress assay of mouse lung fibroblasts (data shown are means±SD of 6 wells in each condition) exposed to vehicle (light grey), 1 µM (medium grey) or 5 µM (black) MIA-602 for 24 hours before measurements of oxygen consumption with oligomycin, FCCP, antimycin A and rotenone. Five µM MIA-602 increased basal oxygen consumption (*, P=0.0403 compared to vehicle) and maximal, uncoupled respiration (**, P<0.0001) of normal mouse lung fibroblasts. FIG. 6B shows that 5 µM MIA-602 increased both basal respiration (*, P=0.0125) and spare respiratory capacity (**, P<0.0001).

FIG. 7A shows heat map analysis showing differential gene expression in lungs from mice treated with bleomycin for 28 days that also received MIA-602 (+) or vehicle (−) for the first 21 days. The left two columns show gene expression in bleomycin- and MIA-602-treated mice, whereas the right two columns show gene expression in bleomycin- and vehicle-treated lungs. FIG. 7B shows pathway analysis showing differentially expressed genes (downregulated, top panel; upregulated, bottom panel) in lungs from bleomycin-treated mice also treated with MIA-602 compared to those also treated with vehicle.

DETAILED DESCRIPTION

Figure 1A:
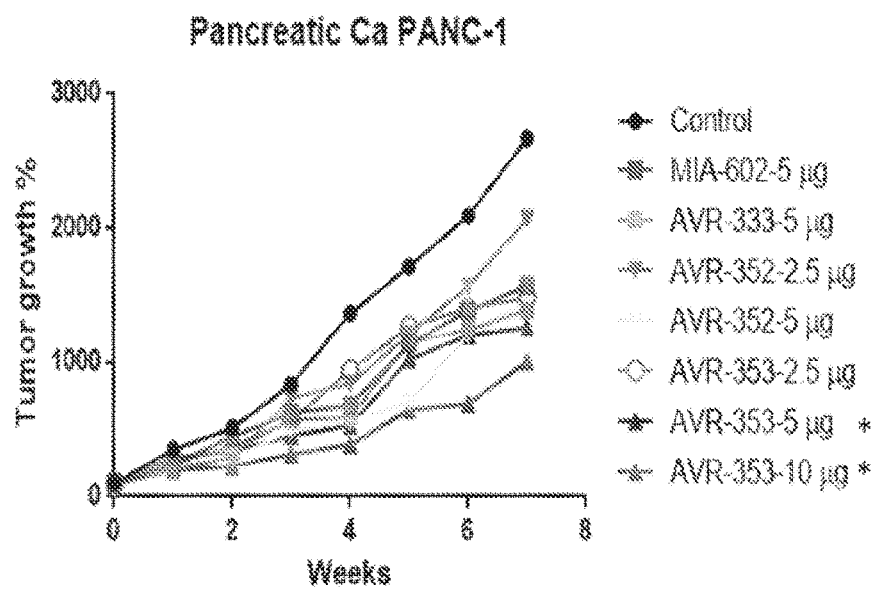
FIGS. 1A-1N are graphs showing the effects of GHRH antagonists.

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosures. Further, the dates of publication provided herein can be different from the actual publication dates, which can require independent confirmation.

Definitions

As used in the specification and in the claims, the term "comprising" can include the aspects "consisting of" and "consisting essentially of." "Comprising" can also mean "including but not limited to."

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

The word "or" as used herein means any one member of a particular list and also includes any combination of members of that list.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject can be a mammal. In some aspects, a subject can a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for pulmonary fibrosis, such as, for example, prior to the administering step. In some aspects of the disclosed methods, the "patient" has been diagnosed with a need for treatment for cancer, such as, for example, prior to the administering step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. Treatment can also be administered to a subject to ameliorate one more signs of symptoms of a disease, disorder, and/or condition. For example, the disease, disorder, and/or condition can be pulomonary fibrosis or a cancer.

The term "fragment" can refer to a portion (e.g., at least 4, 5, 6, 7, 8, 9, 10, 11, 12, 13, 14, 15, 16, 17, 18, 19, 20, 21, 22, 23, 24, 25, 26, 27, 28, 29, 30, etc amino acids) of a peptide that is substantially identical to a reference peptide and retains the biological activity of the reference. In some aspects, the fragment or portion retains at least 50%, 75%, 80%, 85%, 90%, 95% or 99% of the biological activity of the reference peptide described herein. Further, a fragment of a referenced peptide can be a continuous or contiguous portion of the referenced polypeptide (e.g., a fragment of a peptide that is ten amino acids long can be any 2-9 contiguous residues within that peptide).

A "variant" can mean a difference in some way from the reference sequence other than just a simple deletion of an N- and/or C-terminal amino acid residue or residues. For example, disclosed are variants of the growth hormone releasing hormone peptides described herein. Where the variant includes a substitution of an amino acid residue, the substitution can be considered conservative or non-conservative. Conservative substitutions are those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline. In some aspects, the variants can comprise a sequence having at least 20%, 30%, 40%, 50%, 60%, 70%, 80%, 90%, 95%, 98%, 99% identity to any of the sequences described herein. In some aspects, the variants retain at least 50%, 75%, 80%, 85%, 90%, 95% or 99% of the biological activity of the reference peptide described herein.

As used herein, the term "amelioration" refers to a lessening of at least one indicator, sign, or symptom of an associated disease, disorder, or condition. The severity of indicators may be determined by subjective or objective measures, which are known to those skilled in the art.

As used herein the terms "amino acid" and "amino acid identity" refers to one of the 20 naturally occurring amino acids or any non-natural analogues that may be in any of the antibodies, variants, or fragments disclosed. Thus "amino acid" as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In some aspects, the amino acids are in the (S) or L-configuration. If non-naturally occurring side chains are used, non-amino acid substituents may be used, for example to prevent or retard in vivo degradation.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

As used herein, the term "prevent" or "preventing" refers to preventing in whole or in part, or ameliorating or controlling.

| Abbreviations | |
|---|---|
| Amino Acid | Abbreviations |
| 12-aminododecanoic acid | Ada |
| aminobutyric acid | Abu |
| alanine | Ala (A) |
| arginine | Arg (R) |
| asparagine | Asn (N) |
| aspartic acid | Asp (D) |
| cysteine | Cys (C) |
| glutamic acid | Glu (E) |
| glutamine | Gln (K) |
| glycine | Gly (G) |
| histidine | His (H) |
| homoarginine | Har |
| isolelucine | Ile (I) |
| leucine | Leu (L) |
| lysine | Lys (K) |
| methionine | Met (M) |
| norleucine | Nle |
| ornithine | Orn |
| phenylalanine | Phe (F) |
| proline | Pro (P) |
| serine | Ser (S) |
| threonine | Thr (T) |
| tyrosine | Tyr (Y) |
| tryptophan | Trp (W) |
| valine | Val (V) |
| Phenylacetic acid | PhAC |
| Pentafluorophenylacetic acid | 5FPhAC |
| Pentafluorophenylalanine | 5FPhe |
| 8-aminoocotanotic acid | Aoc |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The present disclosure is based in part on the discovery that certain growth hormone-releasing hormone (GHRH) antagonists have an inhibitory effect on several human cancers, including human gastric, pancreatic, colorectal and lung cancers.

Growth hormone-releasing hormone (GHRH) is secreted primarily from the hypothalamus, but various other tissues can produce it locally (Kiaris H, Chatzistamou I, Papavassiliou A, Schally A (2011). Trends Endocrinol Metab 22:311-317). GHRH stimulates the secretion and release of growth hormone (GH) by the pituitary and in turn regulates the secretion of GH and insulin-like growth factor 1 (IGF-1) through the pituitary GH/hepatic IGF-1 axis (Hung C, Rohani M, Lee S, Chen P, Schnapp L (2013). Respir Res 14:102). Expression of pituitary type GHRH-receptor (pGHRH-R) has been found in normal human and IPF lung tissue by western blotting, suggesting that GHRH or GH could participate in lung development, growth and repair (Jackson R, Ai L, Zhang C, Zhang X, Delcroix G, Lazerson A, Mirsaeidi M, Schally A (2018). European Respiratory Journal 52 (suppl 62): OA5349).

GHRH belongs to a peptide family that includes glucagon, secretin, vasoactive intestinal peptide (VIP), and pituitary adenylate cyclase-activating peptide (PACAP) (Kiaris H, Chatzistamou I, Papavassiliou A, Schally A (2011). Trends Endocrinol Metab 22:311-317). GHRH-R antagonists exert growth-inhibitory effects in cancers in vitro and in vivo (Perez R, Schally A, Vidaurre I, Ricon R, Block N, Rick F (2012). Oncotarget (3):988-997; Schally A, Varga J, Engel J (2007). Nature Clin Pract Endo Metab 4:33-43; and Zarandi M, Cai R, Kovacs M, Popovics P, Szalontay L, Cui T, Sha W, Jaszberenyi M, Varga J, Zhang X, Block N, Rick F, Halmos G, Schally A (2017). Peptides 89:60-70), in addition to having anti-inflammatory and anti-oxidative effects (Barbutis N, Schally A (2008). PNAS 105:20470-20475).

Human fibroblasts express GHRH receptors, which stimulate proliferation of fibroblasts through GH/IGF-1-mediated signaling. When skin wounds in mice are exposed to GHRH agonist, fibroblasts increase and repair of epithelium is accelerated (Cui T, Jimenez J, Block N, Badiavas E, Rodriguez-Menocal L, Vila Granda A, Cai R, Sha W, Zarandi M, Perez R, Schally A (2016). Oncotarget 7: 52661-52672). GHRH stimulates the expression of α-smooth muscle actin (αSMA), which confers contractile activity in myofibroblasts (Zhang X, Xing R, Chen L, Liu C, Miao Z (2016). Molecular Medicine Reports 14(6):5699-570). In addition to its effects on GH and IGF-1, GHRH-R antagonist MIA-602 inhibits signaling pathways, including PAK1-STAT3/NF-κB in gastric cancer cells, suggesting it could modulate inflammatory and fibrotic processes (Gan J, Ke X, Jiang J, Dong H, Yao Z, Lin Y, Lin W, Wu X, Yan S, Zhuang Y, Chu W, Cai R, Zhang X, Cheung H, Block N, Pang C, Schally A, Zhang H (2016). Proc Natl Acad Sci USA 113:14745-14750).

Described herein is the use of an established bleomycin model of lung inflammation and fibrosis in C57/B16 mice and synthetic GHRH receptor antagonist MIA-602 to test whether inhibition of GHRH receptors would limit inflammation and/or fibrosis.

Disclosed herein are methods of synthesizing highly potent antagonists of growth hormone-releasing hormone (GHRH) AVR class, and methods for using them to inhibit tumor growth, lung inflammation and/or fibrosis.

Compositions

Disclosed herein are growth hormone releasing hormone (GHRH) receptor antagonists (GHRH-R antagonists). In some aspects, the growth hormone releasing hormone (GHRH) receptor antagonists are peptides. In some aspects, the growth hormone releasing hormone (GHRH) receptor antagonists are growth hormone releasing peptides. For example, MIA-602 is a GHRH-R antagonist having the following amino acid sequence, Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-NH$_2$ (SEQ ID NO: 21). MIA-602 can also be referred to as hGH-RH(1-29)NH$_2$. hGH-RH(1-29)NH$_2$ I is considered a standard GHRH-R antagonist [Ac-Tyr$^1$,D-Arg$^2$]. hGH-RH (1-29)NH$_2$ is fragment of the native GH-RH. Synthetic analogs of GHRH based on the structure of hGH-RH(1-29) NH$_2$ (SEQ ID NO: 21) can be used in the methods disclosed herein. Examples of GHRH analogs are disclosed in U.S. Pat. No. 9,260,504 and are incorporated herein by reference. Also disclosed are variants of MIA-602 and fragments thereof.

Disclosed herein are growth hormone releasing hormone (GHRH) receptor antagonists that can be used in methods of treating pulmonary fibrosis; reducing lung inflammation; reducing lung scarring; ameliorating one or more symptoms of pulmonary fibrosis; and reducing expression of one or more T cell receptor complex genes.

In some aspects, the GHRH receptor antagonist can be a growth hormone releasing hormone peptide. In some aspects, the growth hormone releasing hormone peptide comprises or consists of:

(AVR-235, SEQ ID NO: 3)
(a) 5FPhAC-Ada-Tyr-DArg-Asp-Ala-Ile-5FPhe-Thr-Ala-

Har-Tyr(Me)-Arg-Lys-Val-Leu-Abu-Gln-Leu-Ser-Ala-

Arg-Lys-Leu-Leu-Gln-Asp-Ile-Nle-DArg-NHCH$_3$;

(AVR-333, SEQ ID NO: 4)
(b) 5FPhAC-Ada-Tyr-DArg-Asp-Ala-Ile-Cpa-Thr-Asn-

Har-Tyr(Me)-Arg-Lys-Val-Leu-Abu-Gln-Leu-Ser-Ala-

Arg-Lys-Leu-Leu-Gln-Asp-Ile-Nle-DArg-Har-Ada-NH$_2$;

(AVR-352, SEQ ID NO: 5)
(c) 5FPhAC-Ada-Tyr-DArg-Asp-Ala-Ile-5FPhe-Thr-Ala-

Har-Tyr(Me)-Arg-Lys-Val-Leu-Abu-Gln-Leu-Ser-Ala-

Arg-Lys-Leu-Leu-Gln-Asp-Ile-Nle-DArg-Har-Ada-NH$_2$;

(AVR-353, SEQ ID NO: 6)
(d) 5FPhAC-Ada-Tyr-DArg-Asp-Ala-Ile-Cpa-Thr-Ala-

Har-5FPhe-Arg-Lys-Val-Leu-Abu-Gln-Leu-Ser-Ala-Arg-

Lys-Leu-Leu-Gln-Asp-Ile-Nle-DArg-Har-Ada-NH$_2$;
or (AVR-354, SEQ ID NO: 7)
(e) 5FPhAC-Ada-Tyr-DArg-Asp-Ala-Ile-Cpa-Thr-Ala-

Har-5FPhe-Arg-Lys-Val-Leu-Abu-Gln-Leu-Ser-Ala-Arg-

Lys-Leu-Leu-Gln-Asp-Ile-Nle-DArg-Har-NHCH$_3$.

Also disclosed are variants of these growth hormone releasing hormone peptides.

In some aspects, the growth hormone releasing hormone peptide comprises or consists of:

(AVR-104, SEQ ID NO: 8)
(a) PhAC-Ada-Tyr-DArg-Asp-Ala-Ile-Cpa-Thr-Ala-Arg-

Tyr(Me)-Arg-Lys-Val-Leu-Abu-Gln-Leu-Ser-Ala-His-

Orn-Leu-Leu-Gln-Asp-Ile-Nle-DArg-Har-NH$_2$;

(AVR-107, SEQ ID NO: 9)
(b) PhAC-Ada-Tyr-DArg-Asp-Ala-Ile-Cpa-Thr-Ala-Arg-

Tyr-Arg-Lys-Val-Leu-Abu-Gln-Leu-Ser-Ala-Arg-Lys-

Leu-Leu-Gln-Asp-Ile-Nle-DArg-Har-NH$_2$;

(AVR-116, SEQ ID NO: 10)
(c) PhAC-Ada-Tyr-DArg-Asp-Ala-Ile-Cpa-Thr-Ala-Arg-

5FPhe-Arg-Lys-Val-Leu-Abu-Gln-Leu-Ser-Ala-His-Orn-

Leu-Leu-Gln-Asp-Ile-Nle-DArg-Har-NH$_2$;

-continued (d) D-Phe-Ada-Tyr-DArg-Asp-Ala-Ile-Cpa-Thr-Ala-
Arg-Tyr(Me)-Arg-Lys-Val-Leu-Abu-Gln-Leu-Ser-Ala-
His-Orn-Leu-Leu-Gln-Asp-Ile-Nle-DArg-Har-NH$_2$;
(AVR-120, SEQ ID NO: 11)

(e) PhAC-Ada-Tyr-DArg-Asp-Ala-Ile-Cpa-Thr-Ala-Arg-
Amp-Arg-Lys-Val-Leu-Abu-Gln-Leu-Ser-Ala-His-Orn-
Leu-Leu-Gln-Asp-Ile-Nle-DArg-Har-NHCH$_3$;
(AVR-201, SEQ ID NO: 12)

(f) PhAC-Ada-Tyr-DArg-Asp-Ala-Ile-Cpa-Thr-Asn-Arg-
Tyr(Me)-Arg-Lys-Val-Leu-Abu-Gln-Leu-Ser-Ala-Arg-
Lys-Leu-Leu-Gln-Asp-Ile-Nle-DArg-Har-NHCH$_3$;
(AVR-234, SEQ ID NO: 13)

(g) PhAC-Ada-Tyr-DArg-Asp-Ala-Ile-Cpa-Thr-Asn-Har-
Tyr(Me)-Arg-Lys-Val-Leu-Abu-Gln-Leu-Ser-Ala-Arg-
Lys-Leu-Leu-Gln-Asp-Ile-Nle-DArg-Har-Aoc-NHCH$_3$;
(AVR-321, SEQ ID NO: 14)

(h) 5FPhAC-Ada-Tyr-DArg-Asp-Ala-Ile-Cpa-Thr-Asn-
Har-Tyr(Me)-Arg-Lys-Val-Leu-Abu-Gln-Leu-Ser-Ala-
Arg-Lys-Leu-Leu-Gln-Asp-Ile-Nle-DArg-Har-Aoc-
NHCH$_3$;
(AVR-322, SEQ ID NO: 15)

(i) 5FPhAC-Ada-Tyr-DArg-Asp-Ala-Ile-Cpa-Thr-Ala-
Har-5FPhe-His-Orn-Val-Leu-Abu-Gln-Leu-Ser-Ala-His-
Orn-Leu-Leu-Gln-Asp-Ile-Nle-DArg-Har-NHCH$_3$;
(AVR-542, SEQ ID NO: 16)

(j) 5FPhAC-Ada-Tyr-DArg-Asp-Ala-Ile-Cpa-Thr-Ala-
Har-5FPhe-His-Orn-Val-Leu-Abu-Gln-Leu-Ser-Ala-His-
Orn-Leu-Leu-Gln-Asp-Ile-Nle-DArg-Har-Ada-NHCH$_3$;
(AVR-543, SEQ ID NO: 17)

(k) 5FPhAC-Ada-Tyr-DArg-Asp-Ala-Ile-Cpa-Thr-Ala-
Har-5FPhe-His-Orn-Val-Leu-Abu-Gln-Leu-Ser-Ala-His-
Orn-Leu-Leu-Gln-Asp-Ile-Nle-DArg-Har-Ada-NH$_2$;
(AVR-552, SEQ ID NO: 18)

(l) 5FPhAC-Ada-Tyr-DArg-Asp-Ala-Ile-5FPhe-Thr-Ala-
Har-Tyr(Me)-His-Orn-Val-Leu-Abu-Gln-Leu-Ser-Ala-
His-Orn-Leu-Leu-Gln-Asp-Ile-Nle-DArg-Har-Ada-NH$_2$;
or
(AVR-553, SEQ ID NO: 19)

(m) 5FPhAC-Ada-Tyr-DArg-Asp-Ala-Ile-Cpa-Thr-Asn-
Arg-Tyr(Me)-Arg-Lys-Val-Leu-Abu-Gln-Leu-Ser-Ala-
His-Orn-Leu-Leu-Gln-Asp-Ile-Nle-DArg-Har-Ada-NH$_2$.
(AVR-620, SEQ ID NO: 20)

Also disclosed are variants of these growth hormone releasing hormone peptides.

In some aspects, the growth hormone releasing hormone peptide or GHRH receptor antagonist is not MIA-602, SEQ ID NO: 21. In some aspects, the growth hormone releasing hormone peptide or GHRH receptor antagonist does not comprise the sequence of MIA-602, SEQ ID NO: 21

Described herein is a GHRH antagonist comprising the amino acid sequence (formula I): X0-Tyr-DArg-Asp-Ala-Ile-X6-Thr-X8-X9-X10-X11-X12-Val-Leu-Abu-Gln-Leu-Ser-Ala-X20-X21-Leu-Leu-Gln-Asp-Ile-Nle-DArg-X29-X30 (SEQ ID NO: 1). In some aspects, X0 can be 5FPhAC-Ada, D-Phe-Ada, P-C1PhAC, or PhAC-Ada; X6 can be 5FPhe or Cpa; X8 can be Ala or Asn; X9 can be Arg or Har; X10 can be Tyr(Me), 5FPhe or Amp; X11 can be Arg or His; X12 can be Lys or Orn; X20 can be Arg or His; X21 can be Lys or Orn; X29 can be Har, Har-NH$_2$ or Har-NHCH$_3$; and X30 can be present or absent and, when present, can be Ada-NH$_2$, Aoc-NHCH$_3$ or Ada-NHCH$_3$; or a pharmaceutically acceptable salt thereof.

Described herein is a GHRH antagonist comprising the amino acid sequence (formula II): 5FPhAC-Ada-Tyr-DArg-Asp-Ala-Ile-X6-Thr-X8-Har-X10-Arg-Lys-Val-Leu-Abu-Gln-Leu-Ser-Ala-Arg-Lys-Leu-Leu-Gln-Asp-Ile-Nle-DArg-X29-X30 (SEQ ID NO: 2). In some aspects, X6 can be 5FPhe or Cpa; X8 can be Ala or Asn; X10 can be Tyr(Me) or 5FPhe; X29 can be Har or Har-NHCH$_3$; and X30 can be present or absent and, when present, can be Ada-NH$_2$ or Ada-NHCH$_3$; or a pharmaceutically acceptable salt thereof.

Described herein is a GHRH antagonist comprising the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-NHCH$_3$ (AVR-235, SEQ ID NO: 3). In some aspects, the GHRH antagonist comprises the amino acid sequence 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-NH$_2$ (AVR-333, SEQ ID NO: 4). In some aspects, the GHRH antagonist comprises the amino acid sequence 5FPhAC-Ada-Tyr-DArg-Asp-Ala-Ile-5FPhe-Thr-Ala-Har-Tyr(Me)-Arg-Lys-Val-Leu-Abu-Gln-Leu-Ser-Ala-Arg-Lys-Leu-Leu-Gln-Asp-Ile-Nle-DArg-Har-Ada-NH$_2$ (AVR-352, SEQ ID NO: 5). In some aspects, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NH$_2$ (AVR-353, SEQ ID NO: 6). In some aspects, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Har-NHCH$_3$ (AVR-354, SEQ ID NO: 7). In some aspects, the GHRH antagonist comprises the amino acid sequence PhAC-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH$_2$ (AVR-104, SEQ ID NO: 8). In some aspects, the GHRH antagonist comprises the amino acid sequence PhAC-Ada-Tyr-DArg-Asp-Ala-Ile-Cpa-Thr-Ala-Arg-Tyr-Arg-Lys-Val-Leu-Abu-Gln-Leu-Ser-Ala-Arg-Lys-Leu-Leu-Gln-Asp-Ile-Nle-DArg-Har-NH$_2$ (AVR-107, SEQ ID NO: 9). In some aspects, the GHRH antagonist comprises the amino acid sequence PhAC-Ada-Tyr-DArg-Asp-Ala-Ile-Cpa-Thr-Ala-Arg-5FPhe-Arg-Lys-Val-Leu-Abu-Gln-Leu-Ser-Ala-His-Orn-Leu-Leu-Gln-Asp-Ile-Nle-DArg-Har-NH$_2$ (AVR-116, SEQ ID NO: 10). In some aspects, the GHRH antagonist comprises the amino acid sequence D-Phe-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH$_2$ (AVR-120, SEQ ID NO: 11). In some aspects, the GHRH antagonist comprises the amino acid sequence PhAC-Ada-Tyr-DArg-Asp-Ala-Ile-Cpa-Thr-Ala-Arg-Amp-Arg-Lys-Val-Leu-Abu-Gln-Leu-Ser-Ala-His-Orn-Leu-Leu-Gln-Asp-Ile-Nle-DArg- Har-NHCH$_3$ (AVR-201, SEQ ID NO: 12). In some aspects, the GHRH antagonist comprises the amino acid sequence PhAC-Ada-Tyr-DArg-Asp-Ala-Ile-Cpa-Thr-Asn-Arg-Tyr (Me)-Arg-Lys-Val-Leu-Abu-Gln-Leu-Ser-Ala-Arg-Lys-Leu-Leu-Gln-Asp-Ile-Nle-DArg-Har-NHCH$_3$ (AVR-234, SEQ ID NO: 13). In some aspects, the GHRH antagonist comprises the amino acid sequence PhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp- Ile-Nle-DArg-Har-Aoc-NHCH$_3$ (AVR-321, SEQ ID NO: 14). In some aspects, the GHRH antagonist comprises the amino acid sequence 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-NHCH$_3$ (AVR-322, SEQ ID NO: 15). In some aspects, the GHRH antagonist comprises the amino acid sequence 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-His-Orn-Leu-Leu-Gln-Asp-Ile-Nle-DArg-Har-NHCH$_3$ (AVR-542, SEQ ID NO: 16). In some aspects, the GHRH antagonist comprises the amino acid sequence 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NHCH$_3$ (AVR-543, SEQ ID NO: 17). In some aspects, the GHRH antagonist comprises the amino acid sequence 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NH$_2$ (AVR-552, SEQ ID NO: 18). In some aspects, the GHRH antagonist comprises the amino acid sequence 5FPhAC-Ada-Tyr-DArg-Asp-Ala-Ile-5FPhe-Thr-Ala-Har-Tyr(Me)-His-Orn-Val-Leu-Abu-Gln-Leu-Ser-Ala-His-Orn-Leu-Leu-Gln-Asp-Ile-Nle-DArg-Har-Ada-NH$_2$ (AVR-553, SEQ ID NO: 19). In some aspects, the GHRH antagonist comprises the amino acid sequence 5FPhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-His-Orn-Leu-Leu-Gln-Asp-Ile-Nle- DArg-Har-Ada-NH$_2$ (AVR-620, SEQ ID NO: 20).

As used herein, the term "peptide" refers to a linear molecule formed by binding amino acid residues to each other via peptide bonds. As used herein, the term "polypeptide" refers to a polymer of (the same or different) amino acids bound to each other via peptide bonds.

Analogs, fragments and variants of GHRH and any of the growth hormone releasing hormone peptides described herein can be synthesized using standard techniques of peptide chemistry.

In some aspects, the growth hormone releasing hormone peptides described herein can be further modified to improve stability. In some aspects, any of the amino acid residues of the growth hormone releasing hormone peptides described herein can be modified to improve stability. In some aspects, growth hormone releasing hormone peptides can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the growth hormone releasing hormone peptides described herein.

As used herein, the term "stability" refers to storage stability (e.g., room-temperature stability) as well as in vivo stability. The foregoing protective group can protect the peptides described herein from the attack of protein cleavage enzymes in vivo.

As used herein, the term "growth hormone releasing hormone peptide" can also be used to include functional equivalents of the growth hormone releasing hormone peptides described herein or variants thereof. As used herein, the term "functional equivalents" can refer to amino acid sequence variants having an amino acid substitution, addition, or deletion in some of the amino acid sequence of the growth hormone releasing hormone peptides while simultaneously having similar or improved biological activity, compared with the growth hormone releasing hormone peptides as described herein. In some aspects, the amino acid substitution can be a conservative substitution. Examples of the naturally occurring amino acid conservative substitution include, for example, aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met).

Any of the compositions disclosed herein can further comprise a pharmaceutically acceptable carrier. In some aspects, the pharmaceutically acceptable carrier for the growth hormone releasing hormone peptides can be buffered saline. In some aspects, the pharmaceutically acceptable carrier for the small molecule can be water or DMSO. In some aspects, the pharmaceutically acceptable carrier can comprise a lipid-based or polymer-based colloid. In some aspects, the colliod can be a liposome, a hydrogel, a microparticle, a nanoparticle, or a block copolymer micelle. In some aspects, the compositions described herein can be formulated for intravenous, subcutaneous, intrathecal, intratracheal, intramuscular, oral or intraperitoneal administration.

Methods of Treatment

Disclosed herein are methods of inhibiting tumor growth. In some aspects, the methods can comprise administering to a subject in need thereof an effective amount of any one of the GHRH antagonists described herein. In some aspects, the tumor can be prostate cancer, breast cancer, lung cancer, colorectal cancer, melanoma, bladder cancer, brain/CNS cancer, cervical cancer, esophageal cancer, stomach cancer, colon cancer, head/neck cancer, kidney cancer, liver cancer, lymphoma, ovarian cancer, pancreatic cancer, thyroid cancer, glioblastoma, leukemia or sarcoma. In some aspects, the tumor can be a primary tumor or a metastatic tumor.

In some aspects, any of the GHRH antagonists described herein can inhibit growth of a tumor associated with any cancer type. Examples of cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, glioblastoma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some aspects, the tumor can be associated with a cancer selected from the group consisting of breast cancer, melanoma, prostate cancer, pancreatic cancer, head and neck cancer, lung cancer, non small-cell lung carcinoma, renal cancer, colorectal cancer, bladder cancer, stomach cancer, ovarian cancer, sarcoma, esophageal cancer, cervical cancer and gastric cancer. In some aspects, the cancer can be pancreatic cancer.

The disclosure also contemplates use of any of the GHRH antagonists described herein to inhibit tumor growth or treat cancer, as well as use of any of the GHRH antagonist described herein in the preparation of a medicament for inhibiting tumor growth or treating cancer.

Also disclosed herein are methods of treating cancer. In some aspects, the methods can comprise administering to a subject in need thereof an effective amount of any one of the GHRH antagonists described herein. In some aspects, the cancer can be prostate cancer, breast cancer, lung cancer, colorectal cancer, melanoma, bladder cancer, brain/CNS cancer, cervical cancer, esophageal cancer, stomach cancer, colon cancer, head/neck cancer, kidney cancer, liver cancer, lymphoma, ovarian cancer, pancreatic cancer, thyroid cancer, glioblastoma, leukemia or sarcoma.

Further disclosed herein are methods of treating pulmonary fibrosis comprising: administering to a subject with pulmonary fibrosis a therapeutically effective amount of a growth hormone releasing hormone (GHRH) receptor antagonist. Also disclosed herein are methods of reducing lung inflammation comprising: administering to a subject with pulmonary fibrosis a therapeutically effective amount of a growth hormone releasing hormone (GHRH) receptor antagonist. Lung inflammation can be characterized by infiltration of lung tissue with one or more inflammatory cells resulting in impaired oxygen uptake and one or more symptoms such as breathlessness and cough. Further, lung injury caused by inflammation can cause disordered healing and scar formation, which are also characteristic of pulmonary fibrosis. Further disclosed herein are methods of reducing lung scarring comprising: administering to a subject with pulmonary fibrosis a therapeutically effective amount of a growth hormone releasing hormone (GHRH) receptor antagonist. Also disclosed herein are of methods of ameliorating one or more symptoms of pulmonary fibrosis comprising: administering to a subject with pulmonary fibrosis a therapeutically effective amount of a growth hormone releasing hormone (GHRH) receptor antagonist. In some aspects, the one or more symptoms of pulmonary fibrosis can be breathlessness, cough, decreased exercise tolerance, hypoxemia or a combination thereof.

Disclosed herein are methods of reducing expression of one or more T cell receptor complex genes comprising: administering to a subject with pulmonary fibrosis a therapeutically effective amount of a growth hormone releasing hormone (GHRH) receptor antagonist. In some aspects, the one or more T cell receptor complex genes can be CD3E, CD3G, CD4, or CD8A.

In some aspects, the method can comprise: administering to a subject with pulmonary fibrosis a therapeutically effective amount of a growth hormone releasing hormone (GHRH) receptor antagonist. In some aspects, the GHRH receptor antagonist can be a growth hormone releasing hormone peptide. In some aspects, the growth hormone releasing hormone peptide or GHRH receptor antagonist is not MIA-602 (SEQ ID NO: 21).

In some aspects, the growth hormone releasing hormone peptide used in the methods disclosed herein comprises the amino acid sequence:

```
                                 (AVR-235, SEQ ID NO: 3)
(a) 5FPhAC-Ada-Tyr-DArg-Asp-Ala-Ile-5FPhe-Thr-Ala-

Har-Tyr(Me)-Arg-Lys-Val-Leu-Abu-Gln-Leu-Ser-

Ala-Arg-Lys-Leu-Leu-Gln-Asp-Ile-Nle-DArg-NHCH3;

(AVR-333, SEQ ID NO: 4)
(b) 5FPhAC-Ada-Tyr-DArg-Asp-Ala-Ile-Cpa-Thr-Asn-

Har-Tyr(Me)-Arg-Lys-Val-Leu-Abu-Gln-Leu-Ser-Ala-

Arg-Lys-Leu-Leu-Gln-Asp-Ile-Nle-DArg-Har-Ada-NH2;

(AVR-352, SEQ ID NO: 5)
(c) 5FPhAC-Ada-Tyr-DArg-Asp-Ala-Ile-5FPhe-Thr-Ala-

Har-Tyr(Me)-Arg-Lys-Val-Leu-Abu-Gln-Leu-Ser-Ala-

Arg-Lys-Leu-Leu-Gln-Asp-Ile-Nle-DArg-Har-Ada-NH2;
```

(d) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-Ada-NH$_2$; (AVR-353, SEQ ID NO: 6) or (e) 5FPhAC-Ada-Tyr-DArg-Asp-Ala-Ile-Cpa-Thr-Ala-Har-5FPhe-Arg-Lys-Val-Leu-Abu-Gln-Leu-Ser-Ala-Arg-Lys-Leu-Leu-Gln-Asp-Ile-Nle-DArg-Har-NHCH$_3$ (AVR-354, SEQ ID NO: 7)

or variants or fragments thereof.

In some aspects, the growth hormone releasing hormone peptide comprises the amino acid sequence:

(a) PhAC-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH$_2$; (AVR-104, SEQ ID NO: 8)

(b) PhAC-Ada-Tyr-DArg-Asp-Ala-Ile-Cpa-Thr-Ala-Arg-Tyr-Arg-Lys-Val-Leu-Abu-Gln-Leu-Ser-Ala-Arg-Lys-Leu-Leu-Gln-Asp-Ile-Nle-DArg-Har-NH$_2$; (AVR-107, SEQ ID NO: 9)

(c) PhAC-Ada-Tyr-DArg-Asp-Ala-Ile-Cpa-Thr-Ala-Arg-5FPhe-Arg-Lys-Val-Leu-Abu-Gln-Leu-Ser-Ala-His-Orn-Leu-Leu-Gln-Asp-Ile-Nle-DArg-Har-NH$_2$; (AVR-116, SEQ ID NO: 10)

(d) D-Phe-Ada-Tyr-DArg-Asp-Ala-Ile-Cpa-Thr-Ala-Arg-Tyr(Me)-Arg-Lys-Val-Leu-Abu-Gln-Leu-Ser-Ala-His-Orn-Leu-Leu-Gln-Asp-Ile-Nle-DArg-Har-NH$_2$; (AVR-120, SEQ ID NO: 11)

(e) PhAC-Ada-Tyr-DArg-Asp-Ala-Ile-Cpa-Thr-Ala-Arg-Amp-Arg-Lys-Val-Leu-Abu-Gln-Leu-Ser-Ala-His-Orn-Leu-Leu-Gln-Asp-Ile-Nle-DArg-Har-NHCH$_3$; (AVR-201, SEQ ID NO: 12)

(f) PhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-Arg-Lys-Leu-Leu-Gln-Asp-Ile-Nle-DArg-Har-NHCH$_3$; (AVR-234, SEQ ID NO: 13)

(g) PhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-NHCH$_3$; (AVR-321, SEQ ID NO: 14)

(h) 5FPhAC-Ada-Tyr-DArg-Asp-Ala-Ile-Cpa-Thr-Asn-Har-Tyr(Me)-Arg-Lys-Val-Leu-Abu-Gln-Leu-Ser-Ala-Arg-Lys-Leu-Leu-Gln-Asp-Ile-Nle-DArg-Har-Aoc-NHCH$_3$; (AVR-322, SEQ ID NO: 15)

(i) 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-NHCH$_3$; (AVR-542, SEQ ID NO: 16)

(j) 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NHCH$_3$; (AVR-543, SEQ ID NO: 17)

(k) 5FPhAC-Ada-Tyr-DArg-Asp-Ala-Ile-Cpa-Thr-Ala-Har-5FPhe-His-Orn-Val-Leu-Abu-Gln-Leu-Ser-Ala-His-Orn-Leu-Leu-Gln-Asp-Ile-Nle-DArg-Har-Ada-NH$_2$; (AVR-552, SEQ ID NO: 18)

(l) 5FPhAC-Ada-Tyr-DArg-Asp-Ala-Ile-5FPhe-Thr-Ala-Har-Tyr(Me)-His-Orn-Val-Leu-Abu-Gln-Leu-Ser-Ala-His-Orn-Leu-Leu-Gln-Asp-Ile-Nle-DArg-Har-Ada-NH$_2$; (AVR-553, SEQ ID NO: 19) or (m) 5FPhAC-Ada-Tyr-DArg-Asp-Ala-Ile-Cpa-Thr-Asn-Arg-Tyr(Me)-Arg-Lys-Val-Leu-Abu-Gln-Leu-Ser-Ala-His-Orn-Leu-Leu-Gln-Asp-Ile-Nle-DArg-Har-Ada-NH$_2$ (AVR-620, SEQ ID NO: 20)

or variants or fragments thereof.

In some aspects, the methods can further include the step of identifying a subject (e.g., a human patient) who has or is at risk for having pulmonary fibrosis and then providing to the subject a composition comprising a therapeutically effective amount of a growth hormone releasing hormone (GHRH) receptor antagonist. In some aspects, the GHRH receptor antagonist is a growth hormone releasing hormone peptide. In some aspects, the subject can be identified using standard clinical tests known to those skilled in the art. Examples of tests for diagnosing pulmonary fibrosis include but are not limited to high resolution computed tomographic (HRCT) scans of the chest, video-assisted thoracoscopic (VATS) lung biopsies, pulmonary function tests (PFT) and multidisciplinary consultations.

The therapeutically effective amount can be the amount of the composition administered to a subject that leads to a full resolution of the symptoms of the condition or disease, a reduction in the severity of the symptoms of the condition or disease, or a slowing of the progression of symptoms of the condition or disease. The methods described herein can also include a monitoring step to optimize dosing. The compositions described herein can be administered as a preventive treatment or to delay or slow the progression of pulmonary fibrosis.

The dosage to be administered depends on many factors including, for example, the route of administration, the formulation, the severity of the patient's condition/disease, previous treatments, the patient's size, weight, surface area, age, and gender, other drugs being administered, and the overall general health of the patient including the presence or absence of other diseases, disorders or illnesses. Dosage levels can be adjusted using standard empirical methods for optimization known by one skilled in the art. Administrations of the compositions described herein can be single or multiple (e.g., 2- or 3-, 4-, 6-, 8-, 10-, 20-, 50-, 100-, 150-, or more fold). Further, encapsulation of the compositions in a suitable delivery vehicle (e.g., polymeric microparticles or implantable devices) can improve the efficiency of delivery.

The therapeutically effective amount of the compositions described herein can include a single treatment or a series of treatments (i.e., multiple treatments or administered multiple times). Treatment duration using any of compositions disclosed herein can be any length of time, such as, for example, one day to as long as the life span of the subject (e.g., many years). For instance, the composition can be administered daily, weekly, monthly, yearly for a period of 5 years, ten years, or longer. The frequency of treatment can vary. For example, the compositions described herein can be administered once (or twice, three times, etc.) daily, weekly, monthly, or yearly for a period of 5 years, ten years, or longer.

Combination Therapy

In some aspects, the compositions disclosed herein can also be co-administered with another therapeutic agent. Combination therapy (or "co-therapy") can include the GHRH antagonist and another agent as part of a specific treatment regimen intended to provide the beneficial effect from the combined action of these therapeutic agents. Additional therapeutic agents or therapies contemplated for use with the GHRH antagonist described herein include, but are not limited to, androgen deprivation therapy, a chemotherapeutic agent, a radiotherapeutic agent, an immunotherapeutic agent, an inhibitor of cellular proliferation, a regulator of programmed cell death, surgery and other agents.

Androgen deprivation therapy. In some aspects, androgen deprivation therapy can be administered to the subject in combination with the GHRH antagonist. Androgen deprivation therapy comprises the administration of an inhibitor of androgen synthesis to the subject, administration of an androgen receptor antagonist to the subject, administration of a gonadotropin-releasing hormone (GnRH) agonist, administration of a GnRH antagonist or a combination thereof.

In some aspects, the methods described herein further comprise administering an androgen receptor antagonist to the subject. Examples of androgen receptor antagonists include, but are not limited to, Enzalutamide, Bicalutamide, Ostarine, Flutamide, Cyproterone acetate, Gugguisterone, Nilutamide, PF998245, (R)-Bicalutamide, and 1,1-Dichloro-2,2-bis(4-chlorophenyl)ethene, ARN-509 and MDV-3100.

In some aspects, the methods described herein can further comprise administering an inhibitor of androgen synthesis to the subject. In some aspects, the inhibitor of androgen synthesis can be Abiraterone acetate.

In some aspects, the methods described herein further comprise administering a GnRH agonist to the subject. Examples of GnRH agonists include, but are not limited to, leuprolide, buserelin, histrelin, goserelin and deslorelin.

In some aspects, the methods described herein further comprise administering a GnRH antagonist to the subject. Examples GnRH antagonists include, but are not limited to, cetrorelix, ganirelix, abarelix and degarelix.

Chemotherapeutic Agents. In some aspects, chemotherapy may be administered, optionally in regular cycles. Standard of care chemotherapeutic regimens for patients with prostate cancer include, but are not limited to docetazel, cabazitaxel, mitoxantrone, estramustine, doxorubicin, etoposide, vinblastine, paclitaxel, carboplatin and vinorelbine. In some aspects, docetaxel in combination with predisone can be administered in combination with any of the GHRH antagonist described herein.

Chemotherapeutic agents contemplated for use with the methods described herein, include, but are not limited, to erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), bevacizumab (AVASTIN®, Genentech), trastuzumab (HERCEPTIN®, Genentech), pertuzumab (OMNITARG®, rhuMab 2C4, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanam-ine, NOLVADEX®, ISTUBAL®, VALODEX®), doxorubicin (ADRIAMYCIN®), Akti-1/2, HPPD, rapamycin, and lapatinib (TYKERB®, Glaxo SmithKline), oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone), a camptothecin (including the synthetic analog topotecan), bryostatin, callystatin, CC-1065 (including its adozelesin, carzelesin and bizelesin synthetic analogs); cryptophycins (particularly cryptophycin 1 and cryptophycin 8), dolastatin, duocarmycin (including the synthetic analogs, KW-2189 and CBI-TMI); eleutherobin, pancratistatin, a sarcodictyin; spongistatin, nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyano-morpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

Radiation therapy. Radiation and radiotherapeutic agents may also be used in accordance with the methods described herein. Radiation includes, e.g., 7-rays, X-rays, microwaves and UV-irradiation. Radiation may be applied directly to an area of interest by directed delivery of radioisotopes to tumor cells. It is most likely that any of these factors can effect a broad range of damage on DNA, on the precursors of DNA, on the replication and repair of DNA, and/or on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapeutic agents Immunotherapeutics may also be employed for the treatment of cancer Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, for immunotherapy, the tumor cell must bear some marker that is amenable to targeting, i.e., is not present on the majority of other cells. Many tumor markers exist and any of these may be suitable for targeting in the context of the present invention. Examples of markers expressed in prostate tissues include, but are not limited to, prostate-specific antigen (PSA), prostate-specific membrane antigen (PSMA), prostatic acid phosphatase (PAP), prostate stem cell antigen (PSCA), T cell receptor gamma alternate reading frame protein (TARP), transient receptor potential (trp)-p8 and six-transmembrane epithelial antigen of the prostate 1 (STEAP1).

Regulators of programmed cell death. Apoptosis, or programmed cell death, is an important process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, are contemplated for use in combination the AVPR antagonist described herein.

Surgery. In some aspects, a surgical procedure may be employed. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). In some aspects, any of the compositions and methods described herein can be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with any of the GHRH antagonists described herein. In some aspects, the treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other agents. In some aspects, other agents may be used in combination with the methods described herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. In some aspects, the upregulation of cell surface receptors or their ligands such as Fas/Fas ligand, DR4 or DR5/TRAIL can potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In some aspects, cytostatic or differentiation agents can be used in combination with the invention to improve the anti-hyperproliferative efficacy of the treatments. Inhibitors of cell adhesion can also be administered to improve the efficacy of treatment. In some aspects, the cell adhesion inhibitor can be a focal adhesion kinase (FAK) inhibitor or lovastatin.

Pulmonary fibrosis or lung cancer. In some aspects, the methods disclosed herein can further comprise administering pirfenidone (Esbriet®) or nintedanib (Ofev® and Vargatef®) to the subject. In some aspects, the methods disclosed herein can further comprise administering an anti-inflammatory therapy to the subject.

Pharmaceutical Compositions

As disclosed herein, are pharmaceutical compositions, comprising the compositions disclosed herein. In an aspect, the pharmaceutical composition can comprise any of the growth hormone releasing hormone peptides, fragments of the growth hormone releasing hormone peptides or variants of the growth hormone releasing hormone peptides disclosed herein. In some aspects, the pharmaceutical compositions can further comprise a pharmaceutically acceptable carrier. In some aspects, the pharmaceutical compositions described herein can be sterile and contain any of the GHRH antagonists for producing the desired response in a unit of weight or volume suitable for administration to a subject. In some aspects, the pharmaceutical compositions can contain suitable buffering agents, including, e.g., acetic acid in a salt; citric acid in a salt; boric acid in a salt; and phosphoric acid in a salt.

When administered, the therapeutic composition(s) can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term denotes an organic or inorganic ingredient, natural or synthetic, with which the active ingredient is combined to facilitate the application. The components of the pharmaceutical compositions also are capable of being co-mingled with the GHRH antagonist, and with each other, in a manner such that there is no interaction which would substantially impair the desired pharmaceutical efficacy.

As used herein, the term "pharmaceutically acceptable carrier" refers to solvents, dispersion media, coatings, antibacterial, isotonic and absorption delaying agents, buffers, excipients, binders, lubricants, gels, surfactants that can be used as media for a pharmaceutically acceptable substance. The pharmaceutically acceptable carriers can be lipid-based or a polymer-based colloid. Examples of colloids include liposomes, hydrogels, microparticles, nanoparticles and micelles. The compositions can be formulated for administration by any of a variety of routes of administration, and can include one or more physiologically acceptable excipients, which can vary depending on the route of administration. Any of the growth hormone releasing hormone peptides described herein can be administered in the form of a pharmaceutical composition. The growth hormone releasing hormone peptides can be administered by any conventional route, including injection or by gradual infusion over time. The administration may, for example, be oral, intravenous, intratumoral, intraperitoneal, intramuscular, intracavity, subcutaneous, inhalation, or transdermal.

As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed. The compositions can also include additional agents (e.g., preservatives).

The pharmaceutical compositions as disclosed herein can be prepared for oral or parenteral administration. Pharmaceutical compositions prepared for parenteral administration include those prepared for intravenous (or intra-arterial), intramuscular, subcutaneous, intrathecal or intraperitoneal administration. Paternal administration can be in the form of a single bolus dose, or may be, for example, by a continuous pump. In some aspects, the compositions can be prepared for parenteral administration that includes dissolving or suspending the growth hormone releasing hormone peptides in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

In some aspects, the compositions disclosed herein can be formulated for oral, intramuscular, intravenous, intratracheal, subcutaneous or intraperitoneal administration.

In some aspects, the compositions disclosed herein can be administered by injection or by gradual infusion over time. In some aspects, the administration can be oral, intramuscular, intravenous, intratracheal, subcutaneous or intraperitoneal, intratumoral, intracavity, subcutaneous, or transdermal.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment. The compositions can also be formulated as powders, elixirs, suspensions, emulsions, solutions, syrups, aerosols, lotions, creams, ointments, gels, suppositories, sterile injectable solutions and sterile packaged powders. The active ingredient can be any of the growth hormone releasing hormone peptides described herein in combination with one or more pharmaceutically acceptable carriers. As used herein "pharmaceutically acceptable" means molecules and compositions that do not produce or lead to an untoward reaction (i.e., adverse, negative or allergic reaction) when administered to a subject as intended (i.e., as appropriate).

Any of the GHRH antagonists (or a composition comprising any of the GHRH antagonists) can be administered in effective amounts. An "effective amount" with respect to a GHRH antagonist according to the teachings herein is that amount of a GHRH antagonist composition that alone, or together with further doses, produces the desired response, e.g., treats cancer, decreases the proliferation of cancer cells, inhibits tumor growth, kills tumor cells, treats pulmonary fibrosis, reduces lung inflammation, reduces lung scarring, ameliorates one or more symptoms of pulmonary fibrosis, or reduces expression of one or more T cell receptor complex genes. In the case of treating a cancer or treating pulmonary fibrosis, a desired response can be inhibition of progression of the disease. This may involve slowing the progression of the disease temporarily, although more preferably, it involves halting the progression of the disease permanently. In some aspects, disease progression and/or cancer cell death can be monitored by routine methods. In some aspects, administration of the GHRH antagonist delays onset or prevents the onset of cancer. In some aspects, administration of the GHRH antagonist can mediate a reduction in tumor size, such as a reduction in primary tumor volume, or halts or slows growth of a tumor. Optionally, the method described herein can reduce tumor size by at least 1%, 3%, 5%, 10% or more. Alternatively or in addition, the method described herein reduces tumor burden (by, for example, 1%, 3%, 5%, 10% or more); slows, delays, or prevents metastasis; results in a reduction in cancer specific antigen levels (e.g., prostate specific antigen levels) in the blood (by, for example, 10% or more); or improves cancer grading used by clinicians (e.g., Gleason score for prostate cancer). In some aspects, the method described herein decreases cancer cell proliferation by at least 1%, 3%, 5%, 10% or more. In some aspects, the method described herein reduces levels of prostate specific antigen (PSA) (by, for example, 10%, 15%, 20% or more) in the blood of the subject receiving treatment. In some aspects, the method described herein reduces level of PSA by 2-fold, (5-fold, 6-fold, 7-fold, 8-fold, 9-fold, 10-fold, 20-fold, 30-fold, 40-fold, 50-fold, 60-fold, 70-fold, 80-fold or more) in the blood of the subject receiving treatment. It will be appreciated that "treating cancer" does not require a complete elimination of the disease; any improvement in the disease state is beneficial to the patient and contemplated herein. Additionally, it will be appreciated that "inhibiting tumor growth" does not require complete arrest of tumor growth; slowing of tumor growth or progression is contemplated.

Amounts of GHRH antagonist will depend on the severity of the condition, the individual patient parameters including age, physical condition, size and weight, the duration of the treatment, the nature of concurrent therapy (if any), the specific route of administration and like factors within the knowledge and expertise of the health practitioner. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of growth hormone releasing hormone peptides administered to a subject can be chosen in accordance with different parameters, such as the mode of administration used. In the event that a response in a subject is insufficient at the initial doses applied, higher doses (or effectively higher doses by a different, more localized delivery route) may be employed to the extent that patient tolerance permits.

In general, doses of growth hormone releasing hormone peptides can be formulated and administered in doses between 0.5 mg/kg to about 500 mg/kg. In some aspects, the growth hormone releasing hormone peptides can be formulated and administered at a dose ranging from 0.5 mg/kg to about 5 mg/kg, 0.5 mg/kg to about 200 mg/kg, or about 1 mg/kg to about 100 mg/kg, or about 1 mg/kg to about 50 mg/kg. In some aspects, the growth hormone releasing hormone peptides can be formulated and administered at a dose of about 0.5 mg/kg or about 1 mg/kg, or about 5 mg/kg, or about 10 mg/kg, or about 20 mg/kg, or about 30 mg/kg, or about 40 mg/kg, or about 50 mg/kg, or about 60 mg/kg, or about 70 mg/kg, or about 80 mg/kg, or about 90 mg/kg, or about 100 mg/kg.

In some aspects, doses of growth hormone releasing hormone peptides can be formulated and administered in a dose of ranging from about 30 mg to about 300 mg (or about 30 mg to about 50 mg, or about 30 mg to about 100 mg, or about 50 mg to about 150 mg, or about 75 mg to about 200 mg, or about 100 mg to about 300 mg). In some aspects, the growth hormone releasing hormone peptides can be formulated and administered at a dose of about 30 mg, or about 35 mg, or about 40 mg, or about 45 mg, or about 50 mg, or about 55 mg, or about 60 mg, or about 65 mg, or about 70 mg, or about 75 mg, or about 80 mg, or about 85 mg, or about 90 mg, or about 100 mg, or about 150 mg, or about 200 mg, or about 250 mg or about 300 mg).

In some aspects, administration of GHRH antagonist compositions to mammals other than humans, e.g., for testing purposes or veterinary therapeutic purposes, can be carried out under substantially the same conditions as described above.

EXAMPLES

Example 1: Synthesis of GHRH Antagonists

A plurality of AVR growth hormone-releasing hormone (GHRH) antagonists were synthesized using Fmoc-chemistry. The resulting GHRH antagonists contained modifications at positions 0, 6, 8, 10, 11, 12, 20, 21, 29 and 30 compared to a reference set of GHRH antagonists ("MIA" peptides). See Tables 1 and 2 below.

C-terminal methylamide or ethylamide AVR-GHRH antagonists were synthesized using the Fmoc peptide synthesis on [3-((Methyl-Fmoc-amino)-methyl)indol-1-yl] acetyl AM resin or [3-ethyl-Fmoc-amino)-methyl)indol-1- yl]acetyl AM resin. Before starting the synthesis, the Fmoc group was removed from the resin with 20% piperidine in DMF for 20 min. The side chain of Fmoc-amino acids were protected with acid unstable groups such as β-tert-Butyl ester for ASP, tert-Butyl(But) for Ser, Thr and Tyr; Pentamethyldihydrobenzofuran-5-sulfonyl(Pbf) for Har, DArg, Arg; Nδ-tert-Butoxycarbonyl (Boc) for Orn; Nγ-trityl for Asn; Nδ-trityl for Gln. Nε-trityl for Lys and Nim-trityl for His; The coupling was performed by using 3 equivalents of Fmoc amino acid and [2-(1H-Benzotriazole-1-yl)-1,1,3,3-tetramethyluronium hexafluorophosphate](HBTU) mixed in the 0.5 M 1-Hydroxybenzotriazole (HOBT) DMF solution, followed by addition of 6 equivalents of N,N-Diisopropylethylamine (DIPEA) and stirred for a few minutes to become a complete solution, then immediately added to the resin and shaken for 1-2 hours to finish the coupling reaction. The resin with washing and deprotection of Fmoc group was continued for next coupling with following Fmoc acid.

Exemplary synthesis of AVR-235: The following Fmoc amino acid were coupled in the indicated order on methylamide resin: Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-Tyr(Me), Fmoc-Har(pbf), Fmoc-Ala, Fmoc-Thr(But), Fmoc-5FPhe, Fmoc-Ile, Fmoc-Ala, Fmoc-Asp(oBut), Fmoc-DArg(pbf), Fmoc-Tyr(But), Fmoc-Ada and 5FPhAc to obtain the protected resin 5FPhAc-Ada-Tyr(But)-DArg(pbf)-Asp(oBut)-Ala-Ile-5FPhe-Thr(But)-Ala-Har(pbf)-Tyr(Me)-Arg(pbf)-Lys(Boc)-Val-Leu-Abu-Gln(Trt)-Leu-Ser(But)-Ala-Arg(pbf)-Lys(Boc)-Leu-Leu-Gln(Trt)-Asp(oBut)-Ile-Nle-DArg(pbf)-Har(pbf)-NHCH$_3$-®. The protected peptide resin was treated with a mixed reagent and scavengers containing TFA/thioanisol/1,2-Ethanedithiol (EDT)/Anisol/H2O/Phenol (85%/5%/3%/2%/3%/2% by volume) at room temperature for 3 hr. The crude peptide was precipitated with tert-butyl methyl ether and purified with HPLC and analyzed by mass spectrometry.

The purification of the crude peptides was performed on a Beckman Gold HPLC System (Beckman Coulter, Inc., Brea, CA) equipped with 127P solvent Module, model 166P UVVIS Detector, using an XBridge™ reversed phase column (10 mm×250 mm), packed with C18 silica gel, 300A° pore size, 5 m particle size (Waters Co., Milford, MA). The peptides were eluted with a solvent system consisting of solvent A (0.1% aqueous TFA) and solvent B (0.1% TFA in 70% aqueous acetonitrile (MeCN)) in a linear gradient mode of 30-55% of solvent B for 120 min at a flow rate of 5 ml/min. The eluent was monitored at 220 and 280 nm, and the fractions were examined by analytical HPLC using a Hewlett-Packard Model HP-1090 liquid chromatograph and pooled to give maximum purity. Analytical HPLC was carried out on a Supelco Discovery HS C18 reversed-phase column (2.1 mm×50 mm, C18, 300A° pore size, 3 m particle size; Supelco Bellefonte, PA) using gradient elution from 40 to 80% B for 40 min with a solvent system consisting of solvents A and B, defined above, with a flow rate of 0.2 ml/min. The peaks were monitored at 220 and 280 nm. The peptides were judged to be substantially (>95%) pure by analytical HPLC. Molecular masses were determined by Agilent 6210 time-of-flight mass spectrometry in conjugation with 1200 CapLC (Agilent Technologies 6210 Time-of Light LC/MS, Santa Clara, CA). Peptides were eluted on an Agilent Zorbax C18 column (0.5 mm×150 mm, 300A° pore size, 5 m particle size, Agilent, Santa Clara, CA) at a flow rate of 15 l/min with a linear gradient from 35 to 85% B for 30 min. Solvent A is 0.1% formic acid (FA), Solvent B is 90% aqueous MeCN/0.1% FA. TOF settings are as follow: capillary voltage: 4000V; drying gas flow: 7 L/min; drying gas temperature: 300° C.; nebulizer gas: 30 psi; fragmentor voltage: 350V.

Exemplary synthesis of AVR-354: The following Fmoc amino acid were coupled in indicated order on the [3-((Methyl-Fmoc-amino)-methyl)indol-1-yl]acetyl AM resin Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-5FPhe, Fmoc-Har(pbf), Fmoc-Ala, Fmoc-Thr(But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

Synthesis of C-terminal amide compounds of AVR 333, AVR 352 and AVR353: AVR-333, AVR-352 and AVR-353 were synthesized on Rink amide MBHA resin with Fmoc synthesis procedure as described in the synthesis of AVR-235.

For the synthesis of AVR-333, the following Fmoc amid acids were coupled in indicated order on the resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-Tyr(Me), Fmoc-Har(pbf), Fmoc-Asn(Trt), Fmoc-Thr(But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

For the synthesis of AVR 352, the following Fmoc amino acids were coupled in indicated order on Rink amide MBHA resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-5FPhe, Fmoc-Har(pbf), Fmoc-Ala, Fmoc-Thr(But), Fmoc-5FPhe, Fmoc-Ile, Fmoc-Ala, Fmoc-Asp(oBut), Fmoc-DArg(pbf), Fmoc-Tyr(But), Fmoc-Ada and 5FPhAc.

For the synthesis of AVR-353, the following Fmoc amino acids were coupled in indicated order on Rink amide MBHA resin: Fmoc-Ada, Fmoc-Har(pbf), Fmoc-DArg(pbf), Fmoc-Nle, Fmoc-Ile, Fmoc-Asp(oBut), Fmoc-Gln(Trt), Fmoc-Leu, Fmoc-Leu, Fmoc-Lys(Boc), Fmoc-Arg(pbf), Fmoc-Ala, Fmoc-Ser(But), Fmoc-Leu, Fmoc-Gln(Trt), Fmoc-Abu, Fmoc-Leu, Fmoc-Val, Fmoc-Lys(Boc), Fmoc-Arg(pbf), Fmoc-5FPhe, Fmoc-Har(pbf), Fmoc-Ala, Fmoc-Thr(But), Fmoc-Cpa, Fmoc-Ile, Fmoc-Ala, Fmoc-Asp(oBut), Fmoc-DArg(pbf), Fmoc-Tyr(But), Fmoc-Ada and 5FPhAc.

TABLE 1

Amino acid replacements in AVR-GHRH antagonists and MIA-602 and MIA-690 peptides.

| | 0 | 6 | 8 | 9 | 10 | 11 | 12 | 20 | 21 | 29 | 30 | MW | MW-TFA |
|---|---|---|---|---|---|---|---|---|---|---|---|---|---|
| MIA-602 | PhAC-Ada | 5FPhe | Ala | — | — | His | Orn | His | Orn | Har-$NH_2$ | | 3931 | 4843 |

TABLE 1-continued

Amino acid replacements in AVR-GHRH antagonists and MIA-602 and MIA-690 peptides.

| | 0 | 6 | 8 | 9 | 10 | 11 | 12 | 20 | 21 | 29 | 30 | MW | MW-TFA |
|---|---|---|---|---|---|---|---|---|---|---|---|---|---|
| MIA-690 | — | Cpa | — | — | 5FPhe | — | — | — | — | — | | 3934 | 4846 |
| AVR-235 | 5FPhAC-Ada | 5FPhe | — | — | Tyr(Me) | Arg | Lys | Arg | Lys | Har-NH$_2$ | | 4101 | 5013 |
| AVR-333 | — | Cpa | Asn | — | — | — | — | — | — | Har | Ada-NH$_2$ | 4271 | 5183 |
| AVR-352 | — | 5FPhe | Ala | — | — | — | — | — | — | Har | Ada-NH$_2$ | 4284 | 5196 |
| AVR-353 | — | Cpa | — | — | 5FPhe | — | — | — | — | Har | Ada-NH2 | 4287 | 5199 |
| AVR-354 | — | — | — | — | — | — | — | — | — | Har | Ada-NHCH$_3$ | 4301 | 5213 |

TABLE 2

Structures of AVR antagonists tested in vivo.

| | 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| MIA-602 | PhAC-Ada | Tyr | D-Arg | Asp | Ala | Ile | 5FPhe | Thr | Ala | Har | Tyr(Me) | His | Orn | Val | Leu | Abu | Gln |
| MIA-690 | PhAC-Ada | Tyr | D-Arg | Asp | Ala | Ile | Cpa | Thr | Ala | Har | 5FPhe | His | Orn | Val | Leu | Abu | Gln |
| AVR-104 | PhAC-Ada | Tyr | D-Arg | Asp | Ala | Ile | Cpa | Thr | Ala | Arg | Tyr(Me) | Arg | Lys | Val | Leu | Abu | Gln |
| AVR107 | PhAC-Ada | Tyr | D-Arg | Asp | Ala | Ile | Cpa | Thr | Ala | Arg | Tyr | Arg | Lys | Val | Leu | Abu | Gln |
| AVR-116 | PhAC-Ada | Tyr | D-Arg | Asp | Ala | Ile | Cpa | Thr | Ala | Arg | 5FPhe | Arg | Lys | Val | Leu | Abu | Gln |
| AVR-120 | D-Phe-Ada | Tyr | D-Arg | Asp | Ala | Ile | Cpa | Thr | Ala | Arg | Tyr(Me) | Arg | Lys | Val | Leu | Abu | Gln |
| AVR-201 | PhAC-Ada | Tyr | D-Arg | Asp | Ala | Ile | Cpa | Thr | Ala | Arg | Amp | Arg | Lys | Val | Leu | Abu | Gln |
| AVR-234 | PhAC-Ada | Tyr | D-Arg | Asp | Ala | Ile | Cpa | Thr | Asn | Arg | Tyr(Me) | Arg | Lys | Val | Leu | Abu | Gln |
| AVR-235 | 5FPhAC-Ada | Tyr | D-Arg | Asp | Ala | Ile | 5FPhe | Thr | Ala | Har | Tyr(Me) | Arg | Lys | Val | Leu | Abu | Gln |
| AVR-321 | PhAC-Ada | Tyr | D-Arg | Asp | Ala | Ile | Cpa | Thr | Asn | Har | Tyr(Me) | Arg | Lys | Val | Leu | Abu | Gln |
| AVR-322 | 5FPhAC-Ada | Tyr | D-Arg | Asp | Ala | Ile | Cpa | Thr | Asn | Har | Tyr(Me) | Arg | Lys | Val | Leu | Abu | Gln |
| AVR-332 | PhAC-Ada | Tyr | D-Arg | Asp | Ala | Ile | Cpa | Thr | Asn | Har | Tyr(Me) | Arg | Lys | Val | Leu | Abu | Gln |
| AVR-333 | 5FPhAC-Ada | Tyr | D-Arg | Asp | Ala | Ile | Cpa | Thr | Asn | Har | Tyr(Me) | Arg | Lys | Val | Leu | Abu | Gln |
| AVR-352 | 5FPhAC-Ada | Tyr | D-Arg | Asp | Ala | Ile | 5FPhe | Thr | Ala | Har | Tyr(Me) | Arg | Lys | Val | Leu | Abu | Gln |
| AVR-353 | 5FPhAC-Ada | Tyr | D-Arg | Asp | Ala | Ile | Cpa | Thr | Ala | Har | 5FPhe | Arg | Lys | Val | Leu | Abu | Gln |
| AVR-354 | 5FPhAC-Ada | Tyr | D-Arg | Asp | Ala | Ile | Cpa | Thr | Ala | Har | 5FPhe | Arg | Lys | Val | Leu | Abu | Gln |
| AVR-542 | 5FPhAC-Ada | Tyr | D-Arg | Asp | Ala | Ile | Cpa | Thr | Ala | Har | 5FPhe | His | Orn | Val | Leu | Abu | Gln |
| AVR-543 | 5FPhAC-Ada | Tyr | D-Arg | Asp | Ala | Ile | Cpa | Thr | Ala | Har | 5FPhe | His | Orn | Val | Leu | Abu | Gln |
| AVR-552 | 5FPhAC-Ada | Tyr | D-Arg | Asp | Ala | Ile | Cpa | Thr | Ala | Har | 5FPhe | His | Orn | Val | Leu | Abu | Gln |
| AVR-553 | 5FPhAC-Ada | Tyr | D-Arg | Asp | Ala | Ile | 5FPhe | Thr | Ala | Har | Tyr(Me) | His | Orn | Val | Leu | Abu | Gln |
| AVR-620 | 5FPhAC-Ada | Tyr | D-Arg | Asp | Ala | Ile | Cpa | Thr | Asn | Arg | Tyr(Me) | Arg | Lys | Val | Leu | Abu | Gln |

| | 17 | 18 | 19 | 20 | 21 | 22 | 23 | 24 | 25 | 26 | 27 | 28 | 29 | 30 | MW | MW-TFA |
|---|---|---|---|---|---|---|---|---|---|---|---|---|---|---|---|---|
| MIA-602 | Leu | Ser | Ala | His | Orn | Leu | Leu | Gln | Asp | Ile | Nle | D-Arg | Har-NH$_2$ | | 3928 | 4840 |
| MIA-690 | Leu | Ser | Ala | His | Orn | Leu | Leu | Gln | Asp | Ile | Nle | D-Arg | Har-NH$_2$ | | 3931 | 4843 |
| AVR-104 | Leu | Ser | Ala | His | Orn | Leu | Leu | Gln | Asp | Ile | Nle | D-Arg | Har-NH$_2$ | | 3891 | 4803 |
| AVR107 | Leu | Ser | Ala | Arg | Lys | Leu | Leu | Gln | Asp | Ile | Nle | D-Arg | Har-NH$_2$ | | 3909 | 4821 |
| AVR-116 | Leu | Ser | Ala | His | Orn | Leu | Leu | Gln | Asp | Ile | Nle | D-Arg | Har-NH$_2$ | | 3950 | 4862 |
| AVR-120 | Leu | Ser | Ala | His | Orn | Leu | Leu | Gln | Asp | Ile | Nle | D-Arg | Har-NH$_2$ | | 3919 | 4831 |
| AVR-201 | Leu | Ser | Ala | His | Orn | Leu | Leu | Gln | Asp | Ile | Nle | D-Arg | Har-NHCH$_3$ | | 3889 | 4801 |

TABLE 2-continued

Structures of AVR antagonists tested in vivo.

| | | | | | | | | | | | | | | | |
|---|---|---|---|---|---|---|---|---|---|---|---|---|---|---|---|
| AVR-234 | Leu | Ser | Ala | Arg | Lys | Leu | Leu | Gln | Asp | Ile | Nle | D-Arg | Har-NHCH$_3$ | | 3981 | 4893 |
| AVR-235 | Leu | Ser | Ala | Arg | Lys | Leu | Leu | Gln | Asp | Ile | Nle | D-Arg | Har-NHCH$_3$ | | 4098 | 5010 |
| AVR-321 | Leu | Ser | Ala | Arg | Lys | Leu | Leu | Gln | Asp | Ile | Nle | D-Arg | Har | Aoc-NHCH$_3$ | 4136 | 5048 |
| AVR-322 | Leu | Ser | Ala | Arg | Lys | Leu | Leu | Gln | Asp | Ile | Nle | D-Arg | Har | Aoc-NHCH$_3$ | 4226 | 5138 |
| AVR-332 | Leu | Ser | Ala | Arg | Lys | Leu | Leu | Gln | Asp | Ile | Nle | D-Arg | Har | Ada-NH$_2$ | 4178 | 5090 |
| AVR-333 | Leu | Ser | Ala | Arg | Lys | Leu | Leu | Gln | Asp | Ile | Nle | D-Arg | Har | Ada-NH$_2$ | 4268 | 5180 |
| AVR-352 | Leu | Ser | Ala | Arg | Lys | Leu | Leu | Gln | Asp | Ile | Nle | D-Arg | Har | Ada-NH$_2$ | 4281 | 5193 |
| AVR-353 | Leu | Ser | Ala | Arg | Lys | Leu | Leu | Gln | Asp | Ile | Nle | D-Arg | Har | Ada-NH$_2$ | 4284 | 5196 |
| AVR-354 | Leu | Ser | Ala | Arg | Lys | Leu | Leu | Gln | Asp | Ile | Nle | D-Arg | Har | Ada-NHCH$_3$ | 4298 | 5210 |
| AVR-542 | Leu | Ser | Ala | His | Orn | Leu | Leu | Gln | Asp | Ile | Nle | D-Arg | Har-NHCH$_3$ | | 4038 | 4950 |
| AVR-543 | Leu | Ser | Ala | His | Orn | Leu | Leu | Gln | Asp | Ile | Nle | D-Arg | Har | Ada-NHCH$_3$ | 4232 | 5144 |
| AVR-552 | Leu | Ser | Ala | His | Orn | Leu | Leu | Gln | Asp | Ile | Nle | D-Arg | Har | Ada-NH$_2$ | 4218 | 5130 |
| AVR-553 | Leu | Ser | Ala | His | Orn | Leu | Leu | Gln | Asp | Ile | Nle | D-Arg | Har | Ada-NH$_2$ | 4215 | 5127 |
| AVR-620 | Leu | Ser | Ala | His | Orn | Leu | Leu | Gln | Asp | Ile | Nle | D-Arg | Har | Ada-NH$_2$ | 4224 | 5136 |

As shown in Table 1, certain AVR compounds have 5PhAc at N-terminal, Arg at positions 2 and 20, Lys at positions 12 and 21, and modified C-terminal NH$_2$ with —NHCH$_3$ (AVR-235), Ada-NH$_2$ (AVR-253 and AVR-252), or-Ada-NHCH$_3$ (AVR-254).

Example 2: Evaluation of Inhibitory Effects of GHRH Antagonists In Vitro

The inhibitory effects of the various synthesized GHRH antagonists were tested in cell proliferation assays in various human cancer cell lines including stomach cancer (KATOIII, N87), colon cancer (HT-29), urothelial cancer (J82, RT4), pancreatic cancer (PANC-1, CFPAC-1), prostatic cancer (PC3), breast cancer (MX-1, HCC1806), ovarian cancer (SK-OV-3, OVCAR-3) and lung cancer (HCC827, H460).

Cell culture. Human cancer cell lines including pancreatic (PANC-1 and CFPAC-1), lung (HCC827 and H460), stomach (NCI-N87 and KATOIII), urothelial (J82, RT4), prostatic (PC3), breast (MX-1 and HCC 1806), colorectal (HT-29), and ovarian (SK-OV-3 and OVCAR-3) were obtained from the American Type Culture Collection (ATCC) and cultured at 37° C. in a humidified 95% air/5% CO2 atmosphere in the medium recommended by ATCC.

In vitro cell viability. Cell viability was analyzed as follows: cancer cells including pancreatic (PANC-1 and CFPAC-1), lung (HCC827 and H460), stomach (NCI-N87 and KATOIII), urothelial (J82, RT4), prostatic (PC3) and breast (MX-1 and HCC 1806), colorectal (HT-29) and ovarian (SK-OV-3 and OVCAR-3) were grown on 96 well plates to ~60% confluence, the cells were starved for 24 h in culture medium containing 0.5% FBS. Cells were then treated with GHRH antagonists MIA602 AVR compounds at concentrations of 1, 2.5 or 5 µM, or vehicle (0.1% DMSO) in quintuplicates for 72 hours. The medium was replaced every 48 hours. Cell viability was measured using CellTiter 96 aqueous one solution kit (Promega). Inhibitory effects of tested AVR compounds in comparison to that of MIA602 are presented as inhibitory potency.

Figure 2A:
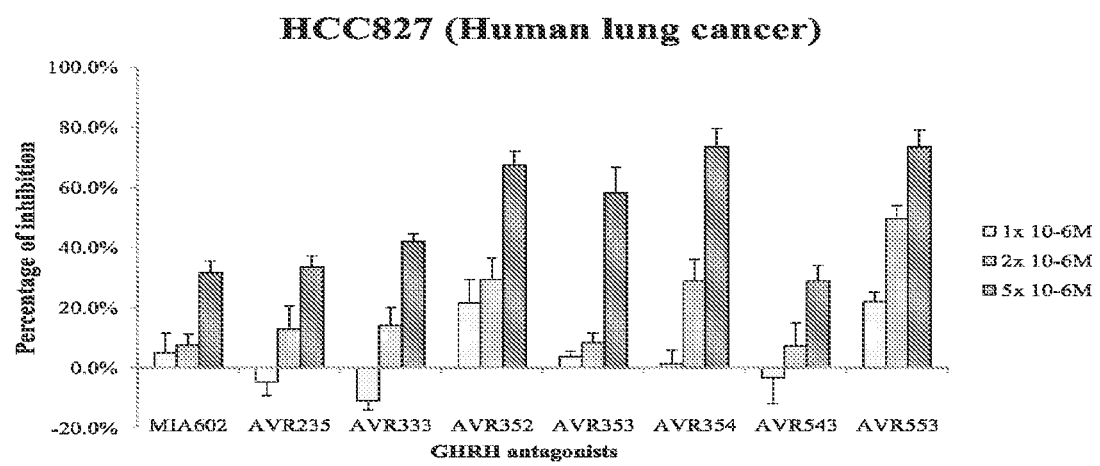
FIGS. 2A-F are graphs showing the inhibitory potency of various GHRH antagonists compared to MIA-602.
Figure 2B:
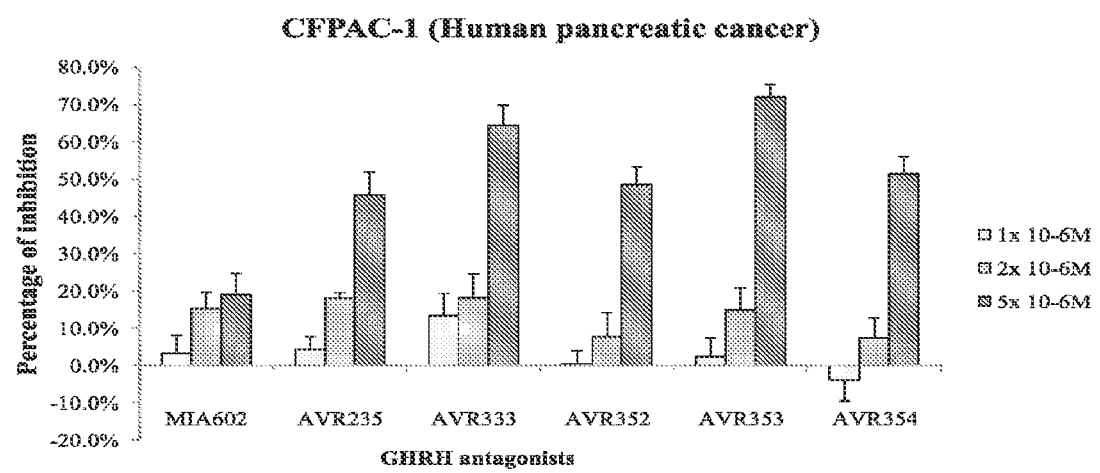
Figure 2C:
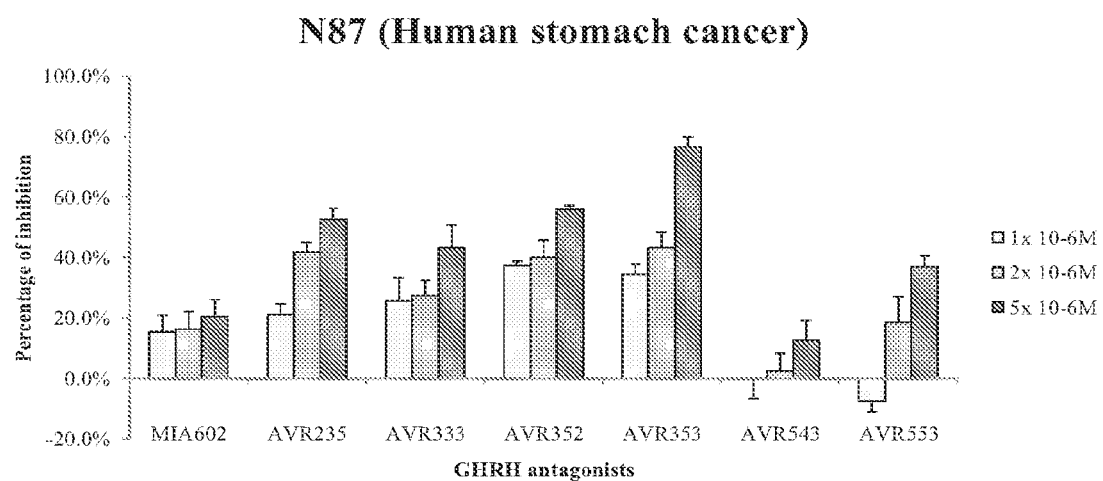
Figure 2D:
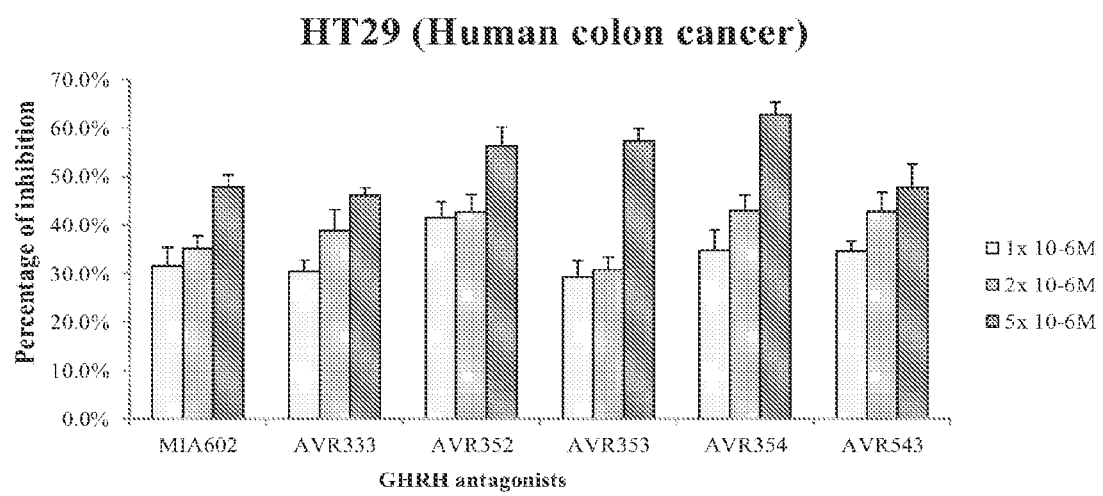
Figure 2E:
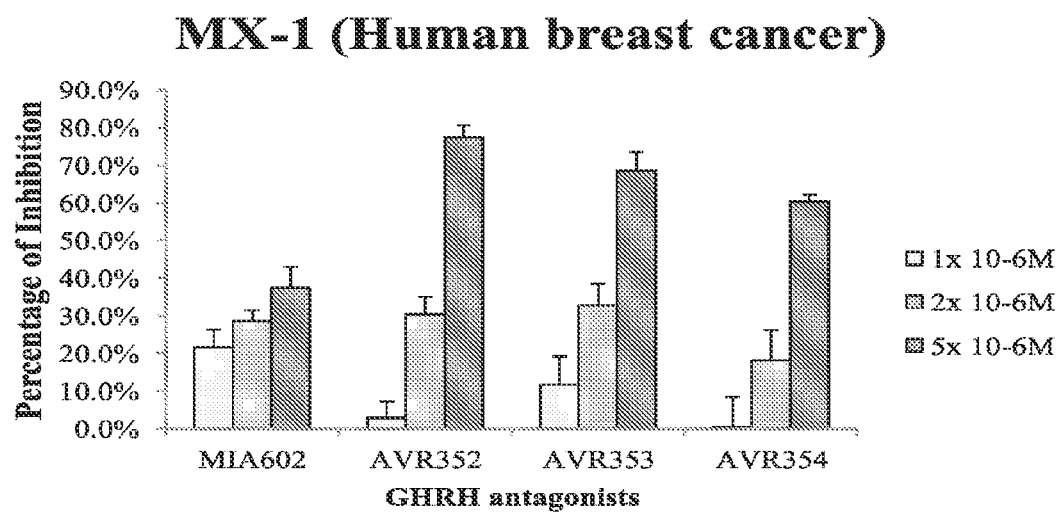
Figure 2F:
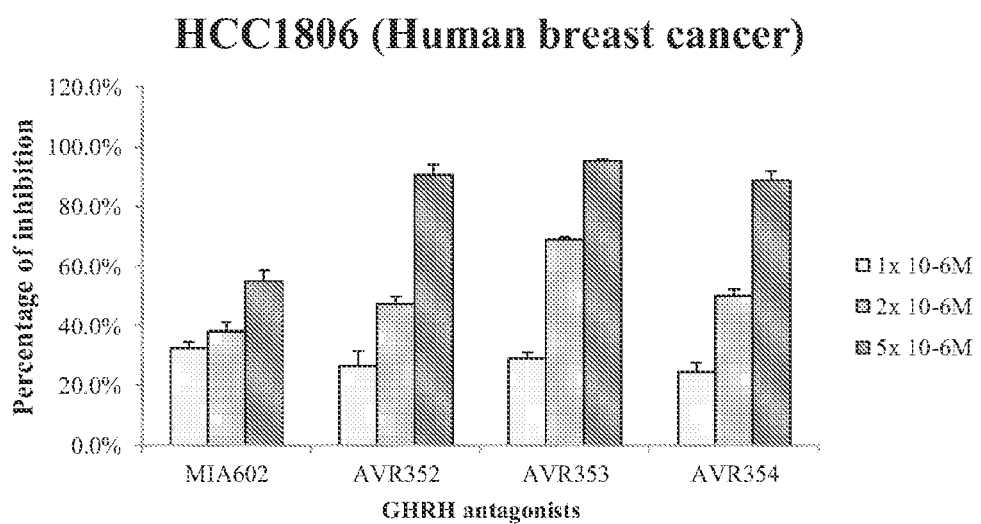

Inhibitory effects of selected AVR compounds in comparison to that of MIA602 are presented as inhibitory potency (e.g., percentage of inhibition). Results for lung cancer cells HCC827 are shown in FIG. 2. FIG. 2 provides a summary of in vitro inhibition of cell viability by the treatment of MIA-602 and selected AVR-antagonists at concentration of 1, 2 and 5 µM for 72 hr. The cell lines tested including lung cancer HCC827 (FIG. 2A), pancreatic cancer CFPAC-1 (FIG. 2B), stomach cancer N87 (FIG. 2C), colon cancer HT-29 (FIG. 2D), breast cancers MX-1 and HCC1806 (FIGS. 2E, F). Based on the results of cell proliferation assay after cancer cells were treated with antagonist at concentration of 5 µM for 72H, the relative inhibitory potency of AVR antagonists in comparison to MIA-602 is summarized in Table 3 A and B. Over 60 AVR compounds were tested in 12 cancer cell lines.

TABLE 3A

GHRH antagonists tested in cancer cell lines.

| GHRH Antagonists | | Stomach | | Lung | Pancreatic | | Urothelial | | Prostatic | Breast | |
|---|---|---|---|---|---|---|---|---|---|---|---|
| Groups | | N87 | KATOIII | HCC827 | CFPAC-1 | Panc-1 | J82 | RT4 | PC3 | HCC1806 | MX-1 |
| MIA | MIA602 | 1 | 1 | 1 | 1 | 1 | 1 | 1 | 1 | 1 | 1 |
| AVR- | 102 | 1.120 | | | | | | | | | |
| | 104 | 2.291 | 1.321 | 1.525 | 1.502 | 1.114 | 3.377 | 1.697 | 1.440 | 1.220 | 1.310 |
| | 105 | | | | 1.090 | 1.120 | 1.380 | | 0.640 | 1.030 | 1.160 |

TABLE 3A-continued

GHRH antagonists tested in cancer cell lines.

| GHRH Antagonists | | Stomach | | Lung | Pancreatic | | Urothelial | | Prostatic | Breast | |
|---|---|---|---|---|---|---|---|---|---|---|---|
| Groups | | N87 | KATOIII | HCC827 | CFPAC-1 | Panc-1 | J82 | RT4 | PC3 | HCC1806 | MX-1 |
| | 107 | | 1.295 | | 1.080 | 1.160 | | | 0.800 | 0.950 | 1.010 |
| | 110 | 1.477 | | | | | | 1.775 | | | |
| | 111 | 1.862 | | | | | | 1.827 | | | |
| | 113 | 0.939 | | | | | | | | | |
| | 115 | 1.963 | | 1.652 | 1.399 | 1.049 | 2.552 | | | | |
| | 116 | 2.484 | 1.202 | 2.470 | 1.445 | 1.208 | 3.034 | | | | |
| | 117 | 1.009 | | | | | | | | | |
| | 118 | 1.332 | | 1.429 | 1.264 | 1.054 | 2.988 | | | | |
| | 119 | 1.568 | | | | | 1.364 | | | | |
| | 120 | 2.339 | 1.271 | 1.423 | 1.617 | 1.306 | 4.841 | 1.611 | | | |
| AVR- | 201 | 3.455 | 1.208 | 1.301 | 1.047 | 1.322 | 0.984 | 1.924 | 0.933 | 1.045 | |
| | 202 | 1.065 | | | | 1.200 | | | 1.010 | 0.920 | |
| | 203 | | | | | 1.120 | | | 1.009 | 0.922 | |
| | 204 | | | | | 1.110 | | | 1.196 | 0.849 | |
| | 205 | | | | | 1.120 | | | 0.979 | 1.091 | |
| | 206 | 1.200 | | | | 1.128 | | | 0.980 | 1.175 | |
| | 207 | | | | | 1.138 | | | 0.901 | 1.219 | |
| | 208 | | | | | 0.945 | | | 0.903 | 0.966 | |
| | 209 | | | | | 1.137 | | | 0.984 | 0.723 | |
| | 210 | | | | | 1.094 | | | 0.982 | 0.664 | |
| | 211 | 1.080 | | | | 1.085 | | | 0.874 | 1.560 | |
| | 212 | | | | | 1.011 | | | 1.111 | 1.119 | |
| | 213 | | | | | 1.112 | | | 1.111 | 1.071 | |
| | 214 | | | | | 0.979 | | | 0.967 | 0.920 | |
| | 215 | | | | | 1.413 | | | 1.012 | 0.820 | |
| | 231 | 1.056 | | | | | | | | | |
| | 232 | 1.466 | | | | | | | | | |
| | 233 | 1.881 | | 1.561 | 1.354 | 0.867 | 1.474 | | | | |
| | 234 | | 1.709 | 4.510 | 2.205 | | | | | | |
| | 235 | 2.911 | 1.220 | 1.506 | 1.399 | 1.139 | 1.518 | | | | |
| | 237 | 1.145 | | | | | | | | | |
| | 238 | 1.603 | | | | | | | | | |

Relative inhibitory potency (continue)

| AVR- | 239 | 0.982 | | | | | | | | | |
|---|---|---|---|---|---|---|---|---|---|---|---|
| | 240 | 1.386 | | | | | | | | | |
| | 241 | 1.117 | | | | | | | | | |
| | 242 | 1.026 | | | | | | | | | |
| | 243 | 2.890 | | 1.438 | 1.340 | 1.034 | 1.296 | | | | |
| | 244 | 1.795 | | 1.160 | 1.118 | 0.970 | 1.176 | | | | |
| | 245 | 1.264 | | | | | | | | | |
| AVR- | 304 | | | 0.631 | | | | | | | |
| | 311 | | 0.919 | | | | | | | | |
| | 312 | | 1.191 | | | | | | | | |
| | 313 | | 1.233 | | | | | | | | |
| | 321 | | 1.414 | | | | | | | | |
| | 322 | | 1.296 | | | | | | | | |
| | 324 | | | 5.227 | | | | | | | |
| | 331 | | 0.907 | | | | | | | | |
| | 332 | | 1.643 | | | | | | | | |
| AVR- | 510 | | 1.064 | | | | | | | | |
| | 520 | | 1.361 | | | | | | | | |
| | 530 | | 1.171 | | | | | | | | |
| | 540 | | 1.626 | | | | | | | | |
| | 551 | | | 1.456 | | | | | | | |
| | 552 | | | 4.376 | 1.57 | | | | | | |
| | 542 | | | 2.649 | 1.312 | | | | | | |
| AVR- | 610 | | 1.479 | | | | | | | | |
| | 620 | | 1.769 | 3.753 | 1.567 | | | | | | |

TABLE 3B

In vitro relative inhibitory potency of AVR-compound in comparison to MIA-602.

| GHRH Antagonists | HCC827 | CFPAC-1 | NCI-N87 | HT-29 | MX-1 | HCC-1806 | SKOV-3 | OVCAR-3 |
|---|---|---|---|---|---|---|---|---|
| MIA-602 | 1 | 1 | 1 | 1 | 1 | 1 | 1 | 1 |
| AVR-235 | 1.08 | 1.497 | 1.67 | 0.968 | — | — | — | — |
| AVR-333 | 1.177 | 2.288 | 1.4 | — | — | — | — | — |
| AVR-352 | 2.01 | 1.576 | 1.809 | 1.197 | 2.793 | 4.85 | 1.15* | 1.68* |

TABLE 3B-continued

In vitro relative inhibitory potency of AVR-compound in comparison to MIA-602.

| GHRH Antagonists | HCC827 | CFPAC-1 | NCI-N87 | HT-29 | MX-1 | HCC-1806 | SKOV-3 | OVCAR-3 |
|---|---|---|---|---|---|---|---|---|
| AVR-353 | 1.641 | 2.922 | 3.404 | 1.222 | 2.001 | 9.396 | 1.04* | 1.55* |
| AVR-354 | 2.595 | 1.67 | — | 1.403 | 1.594 | 3.991 | — | — |
| AVR-543 | 0.961 | 2.05 | 0.908 | 0.999 | — | — | — | — |
| AVR-553 | 2.582 | — | 1.26 | — | — | — | — | — |
| AVR-540 | 1.121 | 2.281 | 1.158 | — | — | — | — | — |

Based on the results of cell proliferation assay after cancer cells were treated with antagonist at concentration of 5 □M for 72H, * at concentration of 2 □M for 72 H.

In vitro assessment of the antagonistic activity of GHRH analogs. Rats were decapitated and pituitaries were collected in pre-warmed HBSS (Hanks' Balanced Salt Solution). Tissue was then cut into small pieces and digested in HBSS medium containing 3% BSA, 50 µg/ml gentamycin and 0.5% collagenase for 50 minutes at 37° C. Cells were further dispersed by pipetting and passed through a 100 µm cell strainer with the addition of DMEM containing 50 µg/ml gentamycin, 10% horse serum and 2.5% FBS (growth medium). Cells were harvested at 475×g for 2 minutes, resuspended in fresh growth medium and seeded onto poly-D-lysine-coated 24-well plates (7 pituitaries/plate). Cells were left to recover for 4 days. Growth medium was then replaced with serum-free DMEM for 4 hours and GHRH analogs (at concentration of 20 nM) were added in DMEM containing 0.1% BSA for 30 minutes. Cells were replenished with medium containing the same concentration of the analogs and 1 nM GHRH(1-29)$NH_2$ for 30 minutes. Medium from this step was collected, centrifuged at 800 g for 3 minutes and GH concentration was determined by ELISA (ALPCO Diagnostics, Mill Valley, CA) according to the manufacturer's instruction.

Figure 3:
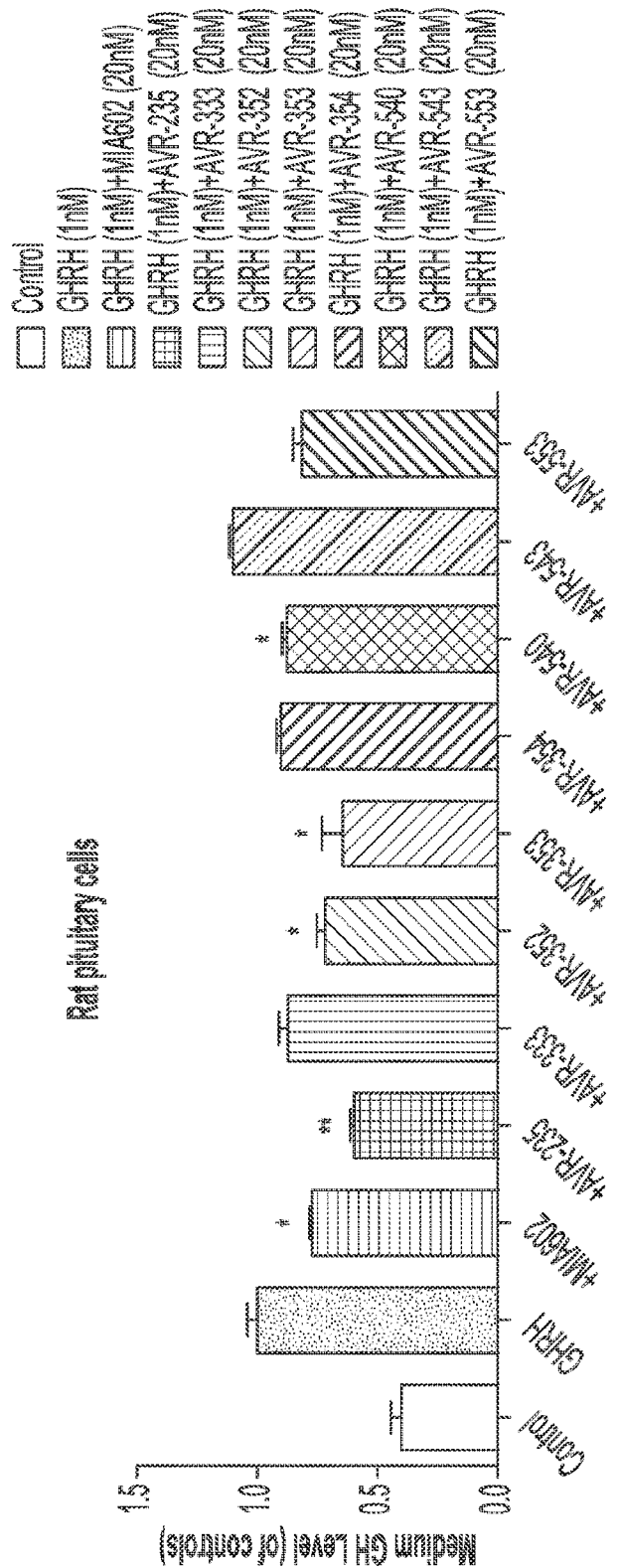
FIG. 3 shows inhibitory effects of GHRH antagonists MIA-602 and AVR-antagonists on the release of GH from rat pituitary cells in vitro. *p<0.05, **p<0.01.

FIG. 3 shows the inhibitory effects of GHRH AVR-antagonists on the release of GH from rat pituitary cells (in vitro) in comparison to antagonists MIA-602. The data is summarized in Table 3C. AVR-235, AVR-352, and AVR-353 showed higher inhibitory effects than MIA-602.

TABLE 3C

Inhibitory effects of GHRH AVR-antagonists on the release of GH from rat pituitary cells (in vitro) in comparison to antagonists MIA-602.

| GHRH antagonists | Relative GH release | p value |
|---|---|---|
| Control | 1.00 ± 0.04 | |
| MIA-602 | 0.78 ± 0.01 | <0.05 |
| AVR-235 | 0.60 ± 0.02 | <0.01 |
| AVR-333 | 0.88 ± 0.03 | ns |
| AVR-352 | 0.72 ± 0.03 | <0.05 |
| AVR-353 | 0.65 ± 0.08 | <0.05 |
| AVR-354 | 0.90 ± 0.02 | ns |
| AVR-540 | 0.88 ± 0.02 | <0.05 |
| AVR-543 | 1.10 ± 0.01 | ns |
| AVR-553 | 0.82 ± 0.04 | 0.06 |

Example 3: Evaluation of Tumor Inhibitory Activity of GHRH Antagonists In Vivo

The inhibitory activity of the GHRH antagonists that displayed high inhibitory properties in the in vitro assays described in Example 2 (i.e., the nineteen antagonists provided in Table 2) were assessed in vivo as to their effect on the growth of human cancers xenografted into nude mice. The peptides' activity was compared with GHRH antagonist MIA-602. All statistical analyzses were performed from comparing GHRA antagonists to non-treated tumor (control).

Peptides and chemicals. GHRH antagonists MIA-602 and AVR-GHRH antagonists (see Table 2 above) were synthesized by solid phase methods and purified by HPLC. The peptides were dissolved in DMSO and further diluted in 10% 1, 2-propanediol. The final concentration of peptides was 50 □g/ml in 10% 1, 2-propanediol containing 0.1% of DMSO.

Cell culture. Human cancer cell lines including pancreatic (PANC-1 and CFPAC-1), lung (HCC827 and H460), stomach (NCI-N87), prostate (PC3), brest (MX-1 and HCC-1806), colorectal (HT-29), and ovarian (SK-OV-3 and OVCAR-3) were obtained from the American Type Culture Collection (ATCC) and cultured at 37° C. in a humidified 95% air/5% $CO_2$ atmosphere in the medium recommended by ATCC.

Xenograft models of human cancers in nude mice. Female athymic (NCr nu/nu) nude mice, 5-to 6-weeks-old, obtained from the Envigo labs (Tampa, FL), were housed in laminar airflow cabinets under pathogen-free conditions with a 12-h light/12-h dark schedule, and were fed autoclaved standard chow and water. To generate mice with xenografted tumors, tumor xenografts were initiated by subcutaneous (s.c.) injection of 10⁷ human cancer cells into female nude mice. After about 4 weeks the resulting tumors were dissected and collected after removing necrosis tissues. The tumors were then cut into particles with size of ~3 mm3 and transplanted s.c. by trocar needle into experimental animals. When tumors grew to the size of 50-60 mm3 (by volume), mice were randomized into groups and treated daily for 4-8 weeks by subcutaneous administration of 5 µg of GHRH antagonists MIA-602 or AVR-compounds (2-10 µg as indicated), or vehicle solutions (0.1% DMSO in 10% 1, 2-propanediol) respectively. Tumor sizes were measured weekly.

Statistical analysis. One-way ANOVA followed by Bonferroni comparison were performed. Data are expressed as Mean±SEM. To determine statistical significance between animal groups, two-tailed Student's t-test was conducted. Differences were considered significant when p<0.05.

Figure 1B:
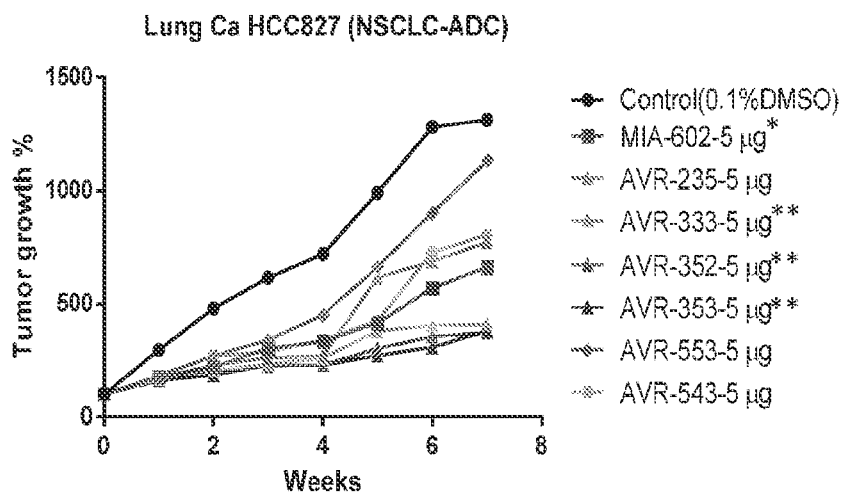
FIG. 1B is a graph showing the effect of GHRH antagonists AVR-235 (5 AVR-333 (5 µg), AVR-353 (5 µg), AVR-553 (5 µg), AVR-543 (5 µg) and AVR-352 (5 µg) compared to MIA-602 (5 µg) on tumor growth in an animal model of lung cancer. Y-axis, % tumor growth; x-axis, time (weeks).
Figure 1C:
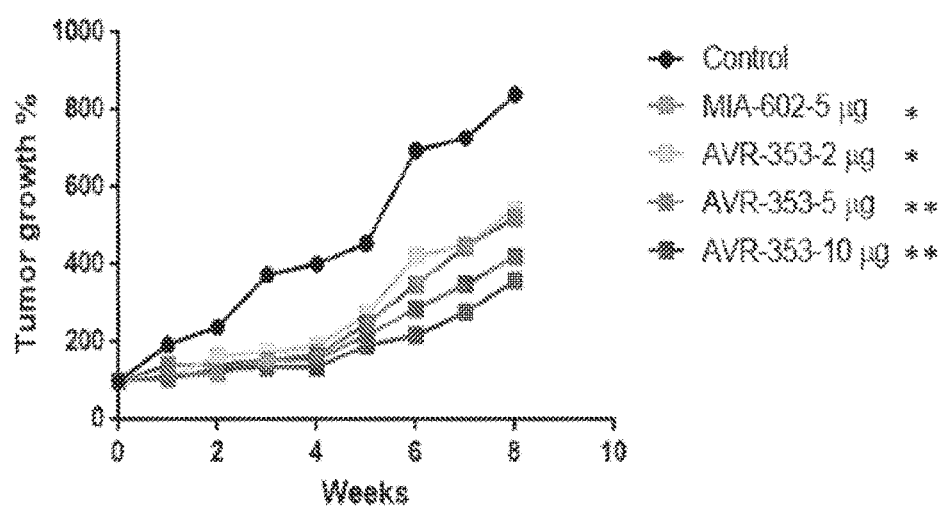
FIG. 1C is a graph showing the effect of GHRH antagonists AVR-353 (2 µg), AVR-353 (5 µg) and AVR-353 (10 µg) compared to MIA-602 (5 µg) on tumor growth in an animal model of lung cancer. Y-axis, % tumor growth; x-axis, time (weeks).
Figure 1D:
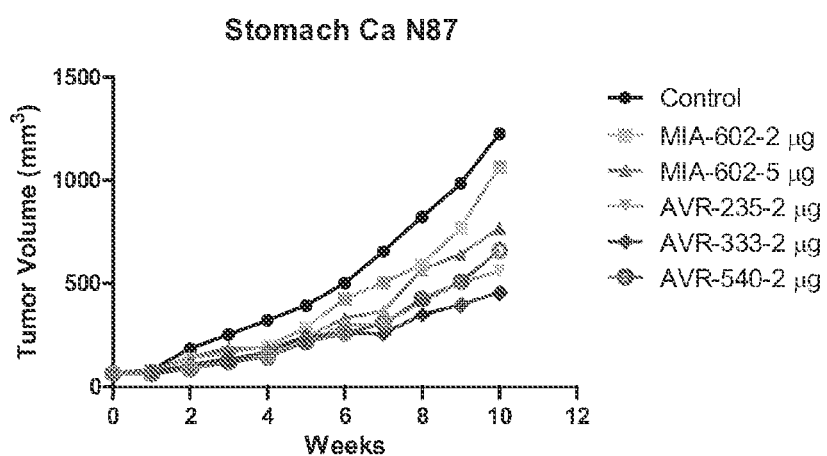
FIG. 1D is a graph showing the effect of GHRH antagonists MIA-602 (5 µg), AVR-235
Figure 1E:
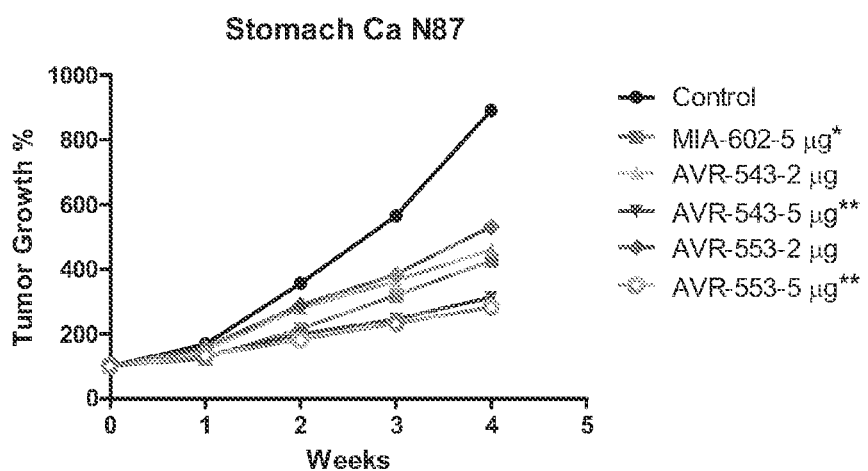
FIG. 1E is a graph showing the effect of GHRH antagonists AVR-543 (2 µg), AVR-543 (5 µg), AVR-553 (2 µg) and AVR-553 (5 µg) compared to MIA-602 (5 µg) on tumor growth in an animal model of stomach cancer. Y-axis, % tumor growth; x-axis, time (weeks).
Figure 1F:
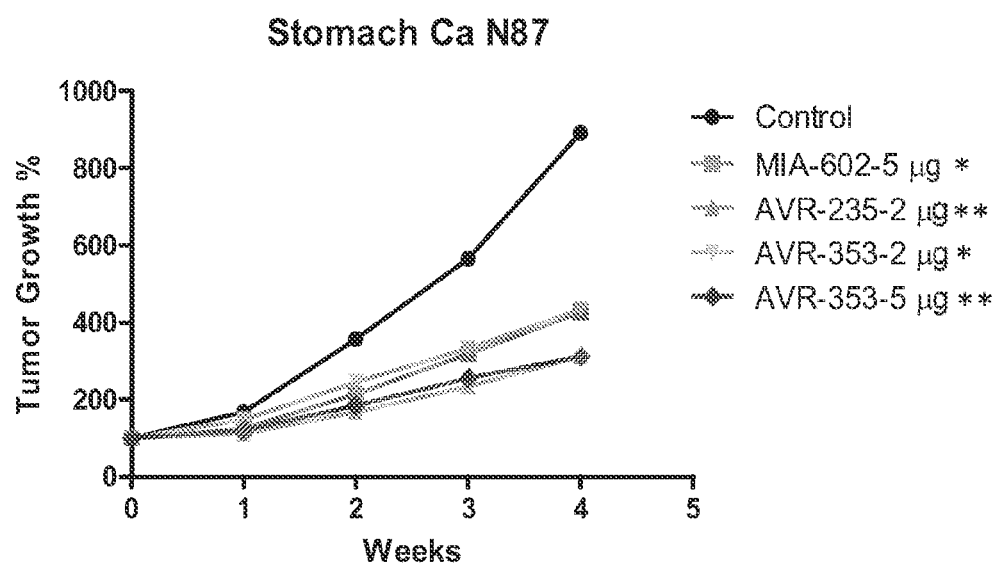
FIG. 1F is a graph showing the effect of GHRH antagonists AVR-235 (2 µg), AVR-353 (2 µg) and AVR-353 (5 µg) compared to MIA-602 (5 µg) on tumor volume in an animal model of stomach cancer. Y-axis, % tumor growth; x-axis, time (weeks).
Figure 1G:
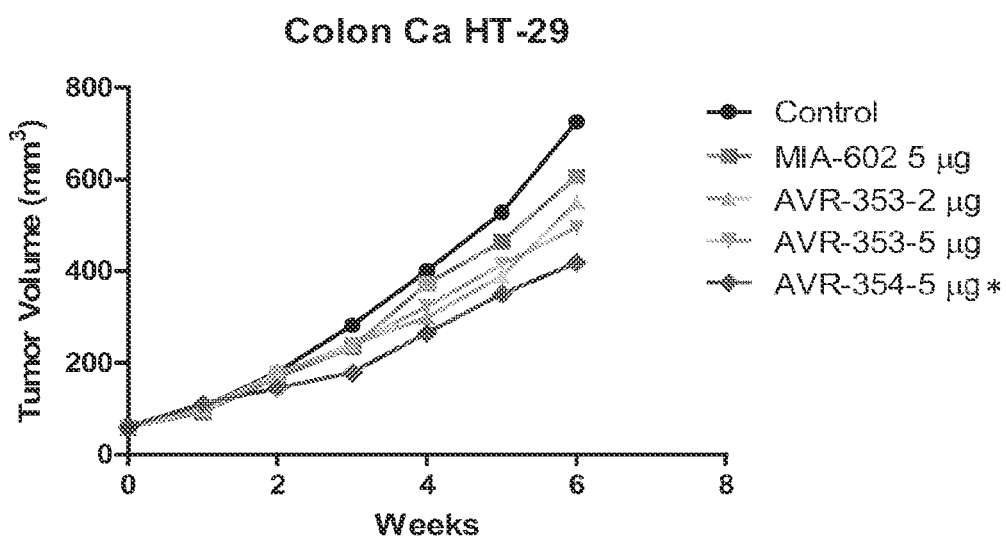
FIG. 1G is a graph showing the effect of GHRH antagonists AVR-353 (2 µg), AVR-353 (5 µg) and AVR-354 (5 µg) compared to MIA-602 (5 µg) on tumor volume in an animal model of colon cancer. Y-axis, % tumor growth; x-axis, time (weeks).
Figure 1H:
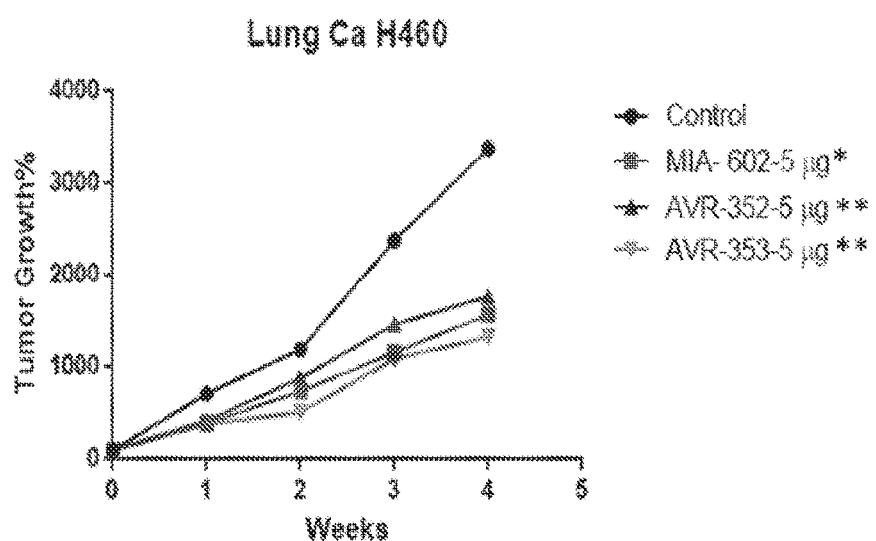
FIG. 1H is a graph showing the effect of GHRH antagonists AVR-352 (5 µg), and AVR-353 (5 µg) compared to MIA-602 (5 µg) on tumor growth in an animal model of lung cancer. Y-axis, % tumor growth; x-axis, time (weeks).
Figure 1I:
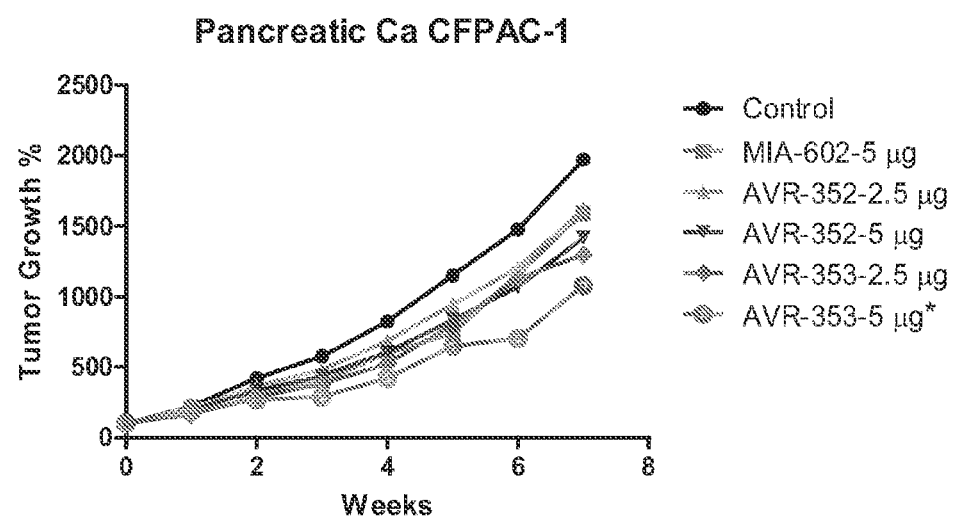
FIG. 1I is a graph showing the effect of GHRH antagonists AVR-352 (2.5 µg), AVR-352 (5 µg), AVR-353 (2.5 µg), and AVR-353 (5 µg) compared to MIA-602 (5 µg) on tumor growth in an animal model of pancreatic cancer.
Figure 1J:
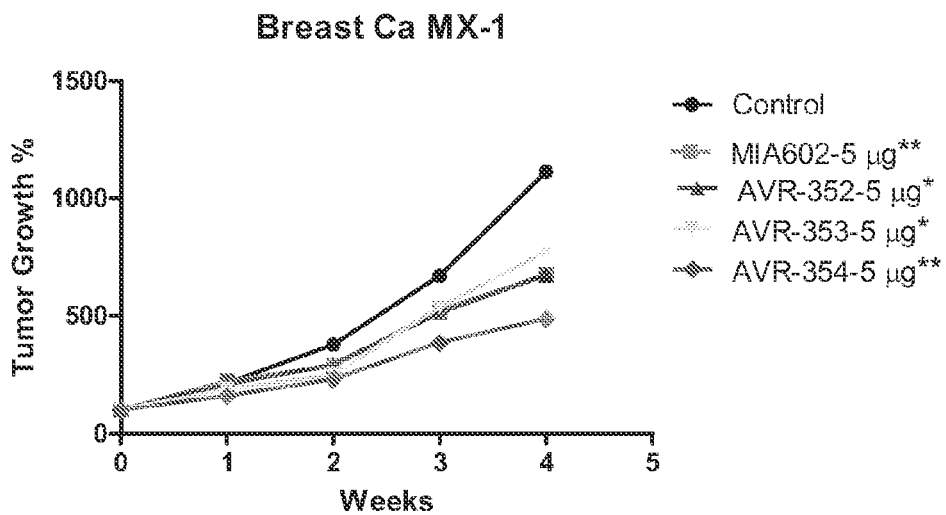
FIG. 1J is a graph showing the effect of GHRH antagonists AVR-352 (5 AVR-353 (5 µg) and AVR-354 (5 µg) compared to MIA-602 (5 µg) on tumor growth in an animal model of breast cancer.
Figure 1K:
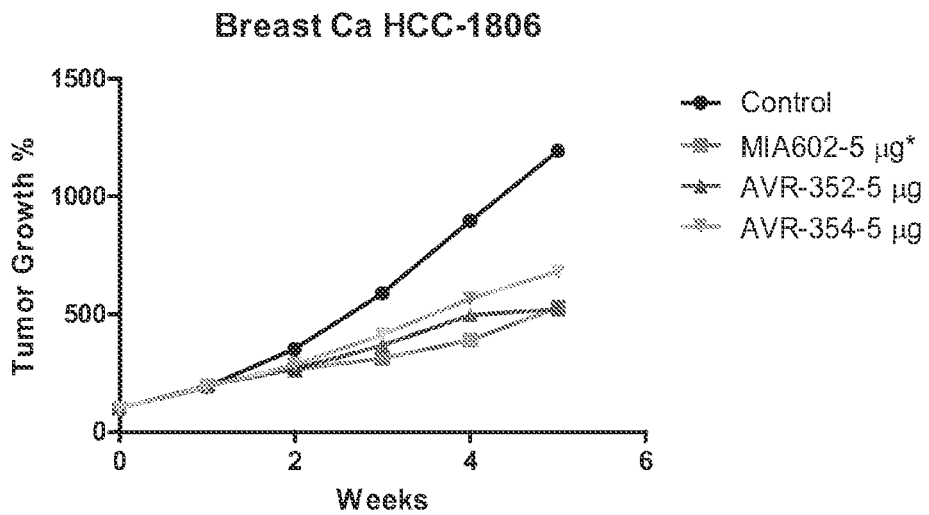
FIG. 1K is a graph showing the effect of GHRH antagonists AVR-352 (5 µg), and AVR-354 (5 µg) compared to MIA-602 (5 µg) on tumor growth in an animal model of breast cancer.
Figure 1L:
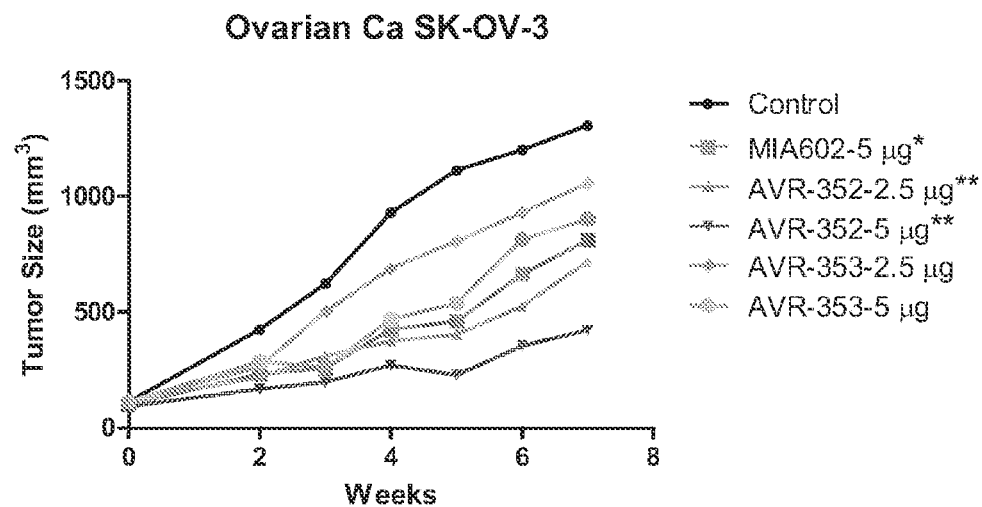
FIG. 1L is a graph showing the effect of GHRH antagonists AVR-352 (2.5 µg), AVR-352 (5 µg), AVR-353 (2.5 µg), and AVR-353 (5 µg) compared to MIA-602 (5 µg) on tumor growth in an animal model of ovarian cancer.
Figure 1M:
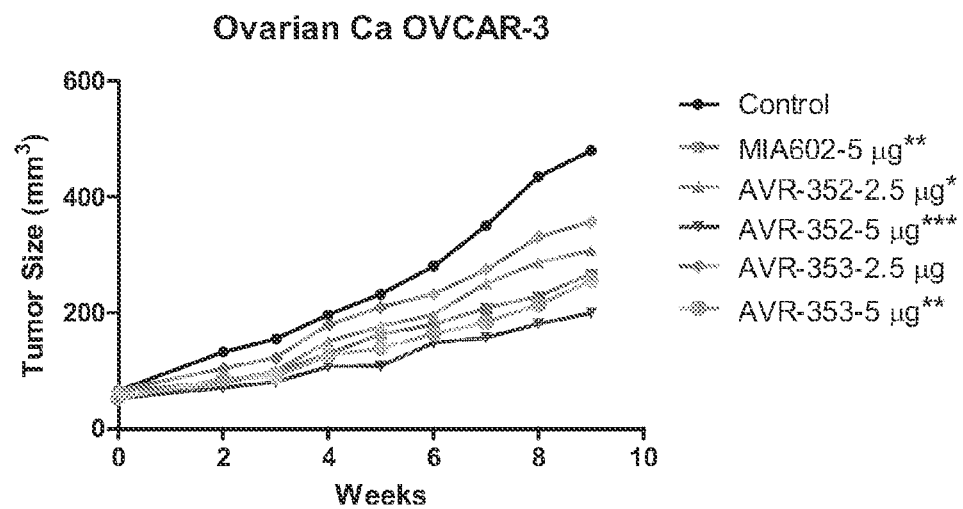
FIG. 1M is a graph showing the effect of GHRH antagonists AVR-352 (2.5 µg), AVR-352 (5 µg), AVR-353 (2.5 µg), and AVR-353 (5 µg) compared to MIA-602 (5 µg) on tumor growth in an animal model of ovarian cancer.
Figure 1N:
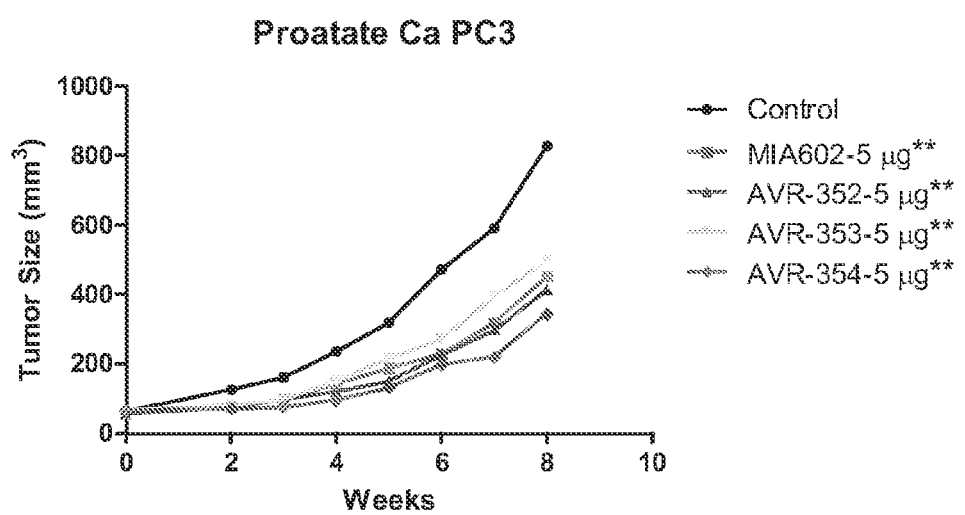

Results. The five AVR GHRH antagonists shown in Table 3 were shown to have the highest inhibitory effects on tumor growth when compared to GHRH antagonist MIA-602. FIG. 1A-N represents in vivo inhibition of tumor growth during the treatment with GHRH antagonist MIA-602 and selected AVR antagonists in nude mice xenografted with various human tumors including pancreatic cancer PANC-1 (FIG. 1A) and CFPAC-1 (FIG. 1I); lung cancer HCC827 (FIGS. 1B, C) and H460 (FIG. 1H); stomach cancer N87 (FIGS. 1D-F); colon cancer HT-29 (FIG. 1G); breast cancer MX-1 and HCC-1806 (FIGS. 1J, K); ovarian cancer SK-OV-3 and OVACAR-3 (FIGS. 1L, M) and prostate cancer PC3 (FIG. 1N). The percentages of inhibition of tumor growth at the end of treatments are summarized in Table 4 (A-N). See also Table 5.

TABLE 4

Oncological in vivo tests on AVR GHRH antagonists.

| Group | Animal (n) Tumor (t) | Tumor Growth % | SEM | P value | % Inhibition |
|---|---|---|---|---|---|
| A Pancreatic Ca PANC-1 (7 weeks) | | | | | |
| Control (0.1% DMSO) | n = 10/t = 13 | 2670.6 | 624.0 | — | — |
| MIA602 (5 µg/day) | n = 9/t = 10 | 1572.7 | 392.3 | ns | 41.1% |
| AVR-333 (5 µg/day) | n = 7/t = 10 | 1384.4 | 169.0 | 0.09 | 48.2% |
| AVR-352 (2.5 µg/day) | n = 10/t = 12 | 2073.0 | 419.9 | ns | 22.4% |
| AVR-352 (5 µg/day) | n = 9/t = 10 | 1456.9 | 217.7 | ns | 45.4% |
| AVR-353 (2.5 µg/day) | n = 8/t = 11 | 1482.8 | 216.4 | ns | 44.5% |
| AVR-353 (5 µg/day) | n = 9/t = 13 | 1257.3 | 268.4 | 0.04 | 52.9% |
| AVR-353 (10 µg/day) | n = 9/t = 11 | 1005.1 | 203.9 | 0.03 | 62.4% |
| B Lung Ca HCC827 (7 weeks) | | | | | |
| Control (0.1% DMSO) | n = 10/t = 16 | 1311.5 | 161.1 | — | — |
| MIA602 (5 µg/day) | n = 10/t = 15 | 662.2 | 88.6 | 0.047 | 49.5% |
| AVR-235 (5 µg/day) | n = 10/t = 15 | 771.0 | 178.0 | ns | 41.2% |
| AVR-333 (5 µg/day) | n = 10/t = 14 | 407.5 | 60.4 | 0.003 | 68.9% |
| AVR-352 (5 µg/day) | n = 10/t = 13 | 371.7 | 102.0 | 0.003 | 71.6% |
| AVR-353 (5 µg/day) | n = 10/t = 12 | 380.3 | 86.8 | 0.004 | 71.0% |
| AVR-553 (5 µg/day) | n = 10/t = 13 | 1132.0 | 218.0 | ns | 13.7% |
| AVR-543 (5 µg/day) | n = 9/t = 15 | 806.0 | 213.0 | ns | 38.6% |
| C Lung Ca HCC827 (8 weeks) | | | | | |
| Control (0.1% DMSO) | n = 11/t = 18 | 840.73 | 100.39 | — | — |
| MIA602 (5 µg/day) | n = 11/t = 18 | 523.03 | 142.47 | 0.04 | 37.8% |
| AVR-353 (2.5 µg/day) | n = 12/t = 17 | 545.65 | 75.25 | 0.03 | 35.1% |
| AVR-353 (5 µg/day) | n = 12/t = 17 | 420.79 | 54.94 | 0.001 | 50.0% |
| AVR-353 (10 µg/day) | n = 11/t = 15 | 359.16 | 72.65 | 0.001 | 57.3% |
| D Stomach Ca N87 (10 weeks) | | | | | |
| Control (0.1% DMSO) | n = 6/t = 11 | 1224.00 | 486.30 | — | — |
| MIA602 (2 µg/day) | n = 6/t = 10 | 1065.00 | 502.10 | ns | 13.0% |
| MIA602 (5 µg/day) | n = 6/t = 12 | 767.00 | 111.40 | ns | 37.3% |
| AVR-235 (2 µg/day) | n = 6/t = 12 | 558.60 | 143.10 | ns | 54.4% |
| AVR-333 (2 µg/day) | n = 6/t = 12 | 454.00 | 58.30 | ns | 62.9% |
| AVR-540 (2 µg/day) | n = 6/t = 12 | 657.80 | 167.60 | ns | 46.3% |

TABLE 4-continued

Oncological in vivo tests on AVR GHRH antagonists.

| Group | Animal (n) Tumor (t) | Tumor Growth % | SEM | P value | % Inhibition |
|---|---|---|---|---|---|
| E Stomach Ca N87 (4 weeks) | | | | | |
| Control (0.1% DMSO) | n = 6/t = 12 | 892.30 | 193.30 | — | — |
| MIA602 (5 µg/day) | n = 6/t = 12 | 427.20 | 72.10 | 0.035 | 52.1% |
| AVR-543 (2 µg/day) | n = 6/t = 12 | 406.8 | 100.2 | 0.061 | 48.4% |
| AVR-543 (5 µg/day) | n = 6/t = 12 | 313.90 | 39.6 | 0.008 | 64.8% |
| AVR-553 (2 µg/day) | n = 6/t = 12 | 532.7 | 57.1 | 0.088 | 40.3% |
| AVR-553 (5 µg/day) | n = 6/t = 12 | 283.3 | 42.0 | 0.006 | 68.3% |
| F Stomach Ca N87 (4 weeks) | | | | | |
| Control (0.1% DMSO) | n = 6/t = 12 | 892.30 | 193.30 | — | — |
| MIA602 (5 µg/day) | n = 6/t = 12 | 427.20 | 72.10 | 0.035 | 52.1% |
| AVR-235 (2 µg/day) | n = 6/t = 12 | 312.80 | 40.90 | 0.008 | 64.9% |
| AVR-353 (2 µg/day) | n = 6/t = 12 | 433.70 | 32.22 | 0.029 | 51.4% |
| AVR-353 (5 µg/day) | n = 6/t = 12 | 312.20 | 42.00 | 0.008 | 65.0% |
| G Colon Ca HT-29 (6 weeks) | | | | | |
| Control (0.1% DMSO) | n = 10/t = 19 | 725.40 | 121.80 | — | — |
| MIA602 (5 µg/day) | n = 10/t = 20 | 582.10 | 145.60 | ns | 16.5% |
| AVR-353 (2 µg/day) | n = 10/t = 16 | 549.30 | 128.80 | ns | 24.2% |
| AVR-353 (5 µg/day) | n = 10/t = 19 | 494.70 | 109.30 | ns | 31.8% |
| AVR-354 (5 µg/day) | n = 10/t = 19 | 417.90 | 66.86 | 0.033 | 42.3% |
| H Lung Ca H460 (4 weeks) | | | | | |
| Control (0.1% DMSO) | n = 11/t = 18 | 3382.6 | 236.4 | | |
| MIA602 (5 µg/day) | n = 9/t = 16 | 1602.7 | 163.5 | <0.001 | 52.6% |
| AVR-352 (5 µg/day) | n = 11/t = 18 | 1738.3 | 306.6 | <0.001 | 48.6% |
| AVR-353 (5 µg/day) | n = 10/t = 16 | 1335.0 | 252.0 | <0.001 | 60.5% |
| I Pancreatic Ca CFPAC-1 (7 weeks) | | | | | |
| Control (0.1% DMSO) | n = 8/t = 13 | 1970.8 | 312.8 | — | — |
| MIA602 (5 µg/day) | n = 7/t = 9 | 1587.5 | 373.9 | ns | 19.5% |
| AVR-352 (2.5 µg/day) | n = 8/t = 14 | 1616.9 | 166.1 | ns | 18.0% |
| AVR-352 (5 µg/day) | n = 11/t = 18 | 1448.4 | 193.1 | ns | 26.5% |
| AVR-353 (2.5 µg/day) | n = 8/t = 14 | 1294.1 | 269.1 | ns | 34.3% |
| AVR-353 (5 µg/day) | n = 9/t = 11 | 1077.6 | 161.4 | 0.018 | 46.2% |
| J Breast Ca MX-1 (4 weeks) | | | | | |
| Control (0.1% DMSO) | n = 10/t = 20 | 1118.4 | 165.5 | — | — |
| MIA602 (5 µg/day) | n = 10/t = 20 | 677.3 | 119.3 | 0.009 | 39.2% |

TABLE 4-continued

Oncological in vivo tests on AVR GHRH antagonists.

| Group | Animal (n) Tumor (t) | Tumor Growth % | SEM | P value | % Inhibition |
|---|---|---|---|---|---|
| AVR-352 (5 µg/day) | n = 10/t = 20 | 673.2 | 108.1 | 0.041 | 39.5% |
| AVR-353 (5 µg/day) | n = 10/t = 20 | 774.2 | 110.1 | 0.046 | 30.5% |
| AVR-354 (5 µg/day) | n = 10/t = 20 | 488.3 | 45.7 | 0.002 | 56.2% |
| K Breast Ca HCC-1806 (5 weeks) | | | | | |
| Control (0.1% DMSO) | n = 10/t = 20 | 1194.7 | 280.1 | | |
| MIA602 (5 µg/day) | n = 10/t = 20 | 529.4 | 63.1 | 0.041 | 55.7% |
| AVR-352 (5 µg/day) | n = 10/t = 20 | 522.7 | 116.2 | 0.056 | 56.2% |
| AVR-354 (5 µg/day) | n = 10/t = 20 | 680.2 | 92.9 | ns | 43.1% |
| L Ovarian Ca SK-OV-3 (7 weeks) | | | | | |
| Control (0.1% DMSO) | n = 10/t = 20 | 1305.7 | 153.1 | | |
| MIA602 (5 µg/day) | n = 10/t = 20 | 810.1 | 68.1 | 0.038 | 38.0% |
| AVR-352 (2.5 µg/day) | n = 10/t = 19 | 718.4 | 135.6 | 0.009 | 45.0% |
| AVR-352 (5 µg/day) | n = 10/t = 20 | 422.3 | 59.5 | 0.005 | 67.7% |
| AVR-353 (2.5 µg/day) | n = 10/t = 19 | 1056.0 | 104.4 | ns | 19.1% |
| AVR-353 (5 µg/day) | n = 10/t = 20 | 910.7 | 134.7 | ns | 30.9% |
| M Ovarian Ca OVCAR-3 (9 weeks) | | | | | |
| Control (0.1% DMSO) | n = 10/t = 20 | 480.2 | 43.9 | | |
| MIA602 (5 µg/day) | n = 10/t = 20 | 267.2 | 27.5 | 0.003 | 44.4% |
| AVR-352 (2.5 µg/day) | n = 10/t = 20 | 307.7 | 43.6 | 0.021 | 35.9% |
| AVR-352 (5 µg/day) | n = 10/t = 20 | 199.9 | 27.8 | <0.001 | 58.4% |
| AVR-353 (2.5 µg/day) | n = 10/t = 20 | 357.0 | 24.8 | ns | 25.7% |
| AVR-353 (5 µg/day) | n = 10/t = 20 | 255.2 | 21.5 | 0.003 | 46.9% |
| N Prostate Ca PC3 (8 weeks) | | | | | |
| Control (0.1% DMSO) | n = 10/t = 20 | 826.7 | 78.6 | | |
| MIA602 (5 µg/day) | n = 10/t = 20 | 450.9 | 41.8 | 0.003 | 45.5% |
| AVR-352 (5 µg/day) | n = 10/t = 20 | 413.3 | 38.4 | 0.007 | 50.0% |
| AVR-353 (5 µg/day) | n = 10/t = 20 | 496.7 | 49.9 | 0.008 | 39.9% |
| AVR-354 (5 µg/day) | n = 10/t = 19 | 343.6 | 28.8 | 0.002 | 58.4% |

TABLE 5

AVR GHRH antagonists demonstrating best inhibitiory activity compared to MIA-602 and MIA-690.

| | 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| MIA-602 | PhAC-Ada | Tyr | D-Arg | Asp | Ala | Ile | 5FPhe | Thr | Ala | Har | Tyr (Me) | His | Orn | Val | Leu | Abu | Gln |
| MIA-690 | PhAC-Ada | Tyr | D-Arg | Asp | Ala | Ile | Cpa | Thr | Ala | Har | 5FPhe | His | Orn | Val | Leu | Abu | Gln |
| AVR-235 | 5FPhAC-Ada | Tyr | D-Arg | Asp | Ala | Ile | 5FPhe | Thr | Ala | Har | Tyr (Me) | Arg | Lys | Val | Leu | Abu | Gln |
| AVR-333 | 5FPhAC-Ada | Tyr | D-Arg | Asp | Ala | Ile | Cpa | Thr | Asn | Har | Tyr (Me) | Arg | Lys | Val | Leu | Abu | Gln |
| AVR-352 | 5FPhAC-Ada | Tyr | D-Arg | Asp | Ala | Ile | 5FPhe | Thr | Ala | Har | Tyr (Me) | Arg | Lys | Val | Leu | Abu | Gln |
| AVR-353 | 5FPhAC-Ada | Tyr | D-Arg | Asp | Ala | Ile | Cpa | Thr | Ala | Har | 5FPhe | Arg | Lys | Val | Leu | Abu | Gln |
| AVR-354 | 5FPhAC-Ada | Tyr | D-Arg | Asp | Ala | Ile | Cpa | Thr | Ala | Har | 5FPhe | Arg | Lys | Val | Leu | Abu | Gln |

| | 17 | 18 | 19 | 20 | 21 | 22 | 23 | 24 | 25 | 26 | 27 | 28 | 29 | 30 | MW | MW-TFA |
|---|---|---|---|---|---|---|---|---|---|---|---|---|---|---|---|---|
| MIA-602 | Leu | Ser | Ala | His | Orn | Leu | Leu | Gln | Asp | Ile | Nle | D-Arg | Har-NH$_2$ | | 3931 | 4843 |
| MIA-690 | Leu | Ser | Ala | His | Orn | Leu | Leu | Gln | Asp | Ile | Nle | D-Arg | Har-NH$_2$ | | 3934 | 4846 |
| AVR-235 | Leu | Ser | Ala | Arg | Lys | Leu | Leu | Gln | Asp | Ile | Nle | D-Arg | Har-NHCH$_3$ | | 4101 | 5013 |
| AVR-333 | Leu | Ser | Ala | Arg | Lys | Leu | Leu | Gln | Asp | Ile | Nle | D-Arg | Har | Ada-NH$_2$ | 4271 | 5183 |
| AVR-352 | Leu | Ser | Ala | Arg | Lys | Leu | Leu | Gln | Asp | Ile | Nle | D-Arg | Har | Ada-NH$_2$ | 4284 | 5196 |
| AVR-353 | Leu | Ser | Ala | Arg | Lys | Leu | Leu | Gln | Asp | Ile | Nle | D-Arg | Har | Ada-NH$_2$ | 4287 | 5199 |
| AVR-354 | Leu | Ser | Ala | Arg | Lys | Leu | Leu | Gln | Asp | Ile | Nle | D-Arg | Har | Ada-NHCH$_3$ | 4301 | 5213 |

Molecular weights are listed as free base and TFA salt. MIA-602 (SEQ ID NO: 21); MIA-690 (SEQ ID NO: 22); AVR-235 (SEQ ID NO: 3); AVR-333 (SEQ ID NO: 4); AVR-352 (SEQ ID NO: 5); AVR-353 (SEQ ID NO: 6); and AVR-354 (SEQ ID NO: 7).

Example 4: Binding Affinities of AVR GHRH Antagonists

Receptor binding affinities in vitro. Preparation of human pituitary membrane fractions and receptor binding of analogs of GH-RH were performed (Halmos G, Rekasi Z, Szoke B, Schally A V. (1993) Receptor 3:87-97). Human pituitary was purchased from the National Hormone and Peptide Program. In the competitive binding analysis, 125I-labeled [His$^1$-Nle$^{27}$]-hGH-RH-(1-32)-NH$_2$ (0.2 nM) was displaced by GH-RH-antagonists at 10-6-10-12 M. The final binding affinities were expressed as IC$_{50}$ values and were calculated by using the LIGAND PC computerized curve-fitting program of Munson and Rodbard as modified by McPherson (Halmos G, Rekasi Z, Szoke B, Schally A V. (1993) Receptor 3:87-97). Relative affinities compared to hGH-RH(1-29)NH$_2$ were calculated as the ratio of IC$_{50}$ (dose causing 50% inhibition of specific binding to receptors) of the tested peptides to the IC$_{50}$ of hGH-RH(1-29)NH$_2$. The values were calculated from technical duplicate tubes.

Nineteen new AVR analogs of GHRH were tested in the receptor binding assay. Table 6 presents the $IC_{50}$ values of GHRH antagonists to membrane GHRH-receptors binding on human anterior pituitary cells. AVR-352, AVR-353, AVR-354, AVR-552 and AVR-553 showed the higher binding affinity in comparison to MIA-602.

TABLE 6

$IC_{50}$ values of new AVR hGH-RH analogs to membrane receptors on human anterior pituitary cells.

| Peptide | | |
|---|---|---|
| SEQ ID No. | Code | $IC_{50}$ [a] (nM) |
| 22 | MIA-690 | 0.53 |
| 21 | MIA-602 | 0.27 |
| 8 | AVR-104 | 0.59 |
| 9 | AVR-107 | 0.61 |
| 10 | AVR-116 | 0.50 |
| 11 | AVR-120 | 0.48 |
| 12 | AVR-201 | 0.61 |
| 13 | AVR-234 | 0.45 |
| 3 | AVR-235 | 0.49 |
| 14 | AVR-321 | 0.23 |
| 15 | AVR-322 | 0.25 |
| 23 | AVR-332 | 0.34 |
| 4 | AVR-333 | 0.30 |
| 5 | AVR-352 | 0.09 |
| 6 | AVR-353 | 0.11 |
| 7 | AVR-354 | 0.14 |
| 16 | AVR-542 | 0.21 |
| 17 | AVR-543 | 0.25 |
| 18 | AVR-552 | 0.17 |
| 19 | AVR-553 | 0.15 |
| 20 | AVR-620 | 0.31 |

[a] $IC_{50}$ values represent mean of two to three determinations. (5FPhAc Ada Tyr DArg Asp Ala Ile 5FPhe Thr Ala HArg Tyr(Me) Arg Lys Val Leu Abu Gln Leu Ser Ala Arg Lys Leu Leu Gln Asp Ile Nle DArg HArg Ada $NH_2$; SEQ ID NO: 23; AVR-332).

Based on these studies GHRH analogs AVR-352, AVR-353, AVR-354, AVR-552 and AVR-553 showed the highest binding affinities to the membrane receptors of human pituitary cells. And, in particular, AVR-352 and AVR-353 strong candidates for further development.

Example 5: Growth Hormone-Releasing Hormone Receptor Antagonist Modulates Lung Inflammation and Fibrosis Due to Bleomycin Abstract. Purpose. Growth hormone-releasing hormone (GHRH) is a 44-amino acid peptide that regulates growth hormone (GH) secretion. It was tested whether a GHRH receptor (GHRH-R) antagonist, MIA-602, would inhibit bleomycin-induced lung inflammation and/or fibrosis in C57Bl/6J mice. Methods. It was tested whether MIA-602 (5 μg or vehicle given subcutaneously [SC] on days 1-21) would decrease lung inflammation (at day 14) and/or fibrosis (at day 28) in mice treated with intraperitoneal (IP) bleomycin (0.8 units on days 1, 3, 7, 10, 14 and 21). Bleomycin resulted in inflammation and fibrosis around airways and vessels evident histologically at days 14 and 28. Results. Inflammation (histopathologic scores assessed blindly) was less evident in mice treated with MIA-602 for 14 days. After 28 days, lung hydroxyproline (HP) content increased significantly in mice treated with vehicle; in contrast, lung HP did not increase significantly compared to naïve controls in mice treated with GHRH-R antagonist. GHRH-R antagonist increased basal and maximal oxygen consumption of cultured lung fibroblasts. Multiple genes related to chemotaxis, IL-1, chemokines, regulation of inflammation and extracellular signal-regulated kinases (ERK) were upregulated in lungs of mice treated with bleomycin and MIA-602. MIA-602 also prominently suppressed multiple genes related to the cellular immune response including those for T cell differentiation, receptor signaling, activation, and cytokine production. Conclusions. MIA-602 reduced lung inflammation and fibrosis due to bleomycin. Multiple genes related to immune response and T cell functions were downregulated, supporting the view that MIA-602 can modulate the cellular immune response to bleomycin lung injury.

Methods. Materials. The GHRH-R antagonist, MIA-602 (MW 4843), was synthesized (PhAC-Ada, Tyr D-Arg, Asp, Ala, Ile, 5FPhe, Thr, Ala, Har, Tyr(Me), His, Orn, Val, Leu, Abu, Gin, Leu, Ser, Ala, His, Orn, Leu, Leu, Gin, Asp, Ile, Nle, D-Arg, Har $NH_2$; SEQ ID NO: 21) at the Miami VAHS by solid phase methods and purified by HPLC.

Experimental animals. 8-week old C57Bl/6J male mice (The Jackson Laboratory, Bar Harbor, ME) were used in these experiments. Mice weighed about 26 grams at the start. Mice were randomly allocated to the experimental groups and housed in identical filter top cages in a ventilated rack. Mice were exposed to a 12-hour light/dark cycle and had free access to standard laboratory chow and water.

Bleomycin and GHRH-R antagonist treatment. Mice were treated with 0.8 units of bleomycin (Bleomycin for Injection USP, Hospira, Lake Forest, IL) intraperitoneally (IP) on days 1, 3, 7, 10, 14 and 21 (Collins S, Chan-Li Y, Oh M, Vigeland C, Limjunyawong N, Mitzner W, Powell J D, Horton M R (2016). JCI Insight 1(4):1-13). Mice (randomly assigned) were simultaneously treated subcutaneously (sc) with MIA-602 (5 μg/day) or its vehicle (100 μL/day) [14]. MIA-602 was dissolved in DMSO (ACS grade; Sigma-Aldrich) and diluted 1:500 in normal saline for daily sc injection on days 0-21.

Tissue preparations. Mice were killed by CO2 inhalation before any treatment, or on days 14 or 28 for micro-CT scans of lungs and harvesting of lung tissue (Vande Velde G, Poelmans J, De Langhe E, Hillen A, Vanoirbeek J, Himmelreich U, Lories R (2016). Dis Model Mech 9:91). The right mainstem bronchus was ligated and the right lung removed and frozen at −80° C. for hydroxyproline (HP) assays. The left lung was filled with 10% buffered formalin at ~25 cm $H_2O$ pressure, the bronchus ligated, and the lung fixed in formalin. Fixed lungs were embedded in wax and 5 μm sections stained with hematoxylin and eosin (H&E) or Masson's trichrome stain.

Lung histopathology. Fibrosis was quantified in trichrome-stained sections using a modification of the Ashcroft score that describes grades of fibrosis. Inflammation in lung tissue was quantified in H&E stained sections (Hubner R, Gitter W, El Mokhtari N, Mathiak M, Both M, Bolte H, Freitag-Wolf S, Bewig B (2008). Biotechniques 44:507-517).

Hydroxyproline assay. Right lungs were weighed and homogenized in 10 volumes of distilled water. Homogenates were hydrolyzed in 12 M HCl at 120° C. for 3 hours (Kennedy J, Chandler D, Jackson R, Fulmer J (1986). Chest 89 (3 Suppl):123S-125S). Hydroxyproline was measured colorimetrically (560 nm) after hydrolysis using an assay kit (MAK008, Sigma-Aldrich, St. Louis, MO).

Micro-CT. Mice in each group were assessed by micro-CT scans (Bruker SkyScan 1176 Low Dose Micro-CT, Knotich, Belgium) of the lungs after CO2 inhalation. A tracheostomy tube was inserted and lungs inflated with air. Scans were examined qualitatively to confirm development of infiltrates and reticular densities.

Lung fibroblasts. Newborn mouse lung fibroblasts (Mlg 2908) were obtained from the American Type Culture Collection, Manassas, VA and cultured in Eagle's minimal essential medium. Cells were grown in 6-well plates before incubation with 1 or 5 μM MIA-602 or vehicle, RNA isolation, and oxygen consumption measurements.

Annexin V-propidium iodide assay. Apoptosis and necrosis were assessed with annexin-V/propidium iodide staining (Annexin V: FITC Assay Kit, Bio Rad, Hercules, CA 94547) of lung fibroblasts incubated in 0, 1 or 5 μM MIA-602 for 24 hours (Rieger A, Nelson K, Konowalchuk J, Barreda D. (2011). J Visualized Experiments 50:e2597). Culture medium and trypsinized cells were collected and centrifuged at 400×g for 5 minutes. The pellet was resuspended in 100 μL annexin-V/propidium iodide. The suspension was incubated at 37° C. for 20 minutes, then washed with PBS and resuspended in 500 μL PBS and fluorescence quantified by Beckman Coulter Life Sciences CytoFLEX benchtop flow cytometer (Beckman Coulter, Inc., Brea, CA).

RNA isolation. RNA was extracted from fixed lung tissue in paraffin blocks using a Quick-RNA™ FFPE Kit (R1008, Zymo Research, Irvine, CA) following the manufacturer's protocol (Patel P, Selvarajah S, Guerard K, Bartlett J, Lapointe J, Berman D, Okello J, Park P (2017). PLoS ONE 12:e0179732). Samples were deparaffinized, digested with proteinase K and decrosslinked at 65° C. for 15 minutes. RNA lysis buffer was added and mixed with ethanol. The mixtures were transferred to spin columns to isolate total RNA.

RNA was extracted from cultured fibroblasts using a Direct-zol RNA MicroPrep kit (R2060; Zymo Research, Irvine, CA). Cells were washed with PBS and lysed in TRIreagent™, then purified using Direct-zol RNA columns. DNase I treatment was done in columns and RNA eluted in DNase/Rnase-free water.

Cellular respiration. The effects of MIA-602 on mouse lung fibroblast oxygen consumption was measured using the Agilent Seahorse XF Cell Mito Stress Test (Agilent Technologies, Santa Clara, CA) (Divakaruni A, Paradyse A, Ferrick D, Murphy A, Jastroch M (2014). Methods in Enzymology 547:309-354). Fibroblasts were incubated with vehicle, 1 or 5 μM MIA-602 for 24 hours before measurement of oxygen consumption. One day before assay 80,000 fibroblasts were seeded into Seahorse 24-well plates (n=6 wells per condition). Basal respiration was established and oligomycin, FCCP and rotenone plus antimycin A were added sequentially to measure ATP production, uncoupled respiration; and, non-mitochondrial oxygen consumption (Wangpaichitr, Wu C, Li Y, Nguyen D, Kandemir H, Shah S, Chen S, Feun L, Prince J, Kuo M, Savaraj N (2017). Oncotarget 8(30):49275-49292).

RNAseq and Pathway analyses. At least 10 ng of total RNA was used as input for the KAPA RNA HyperPrep Kit with RiboErase (HMR) to create ribosomal RNA-depleted sequencing libraries, including sample indexing, to allow for multiplexing. Cluster generation and sequencing was done on the Illumina cBOT and HiSeq 3000 using reagents provided by Illumina, finally generating >32 million single-end 100 base reads per sample.

De-multiplexed FASTQ files were created with Illumina supplied scripts in BCL2FASTQ software (v2.17). Illumina adapters were trimmed using the Trim Galore! package and aligned to the mouse reference genome (mm10) with STAR aligner (v2.5.0a) with default alignment parameters (Dobin A, Davis C, Shlesinger F, Drenkow J, Zaleski C, Jha S, Batut P, Chaisson M, Gingeras T (2013). Bioinformatics 29:15-21).

Gene counts were normalized using trimmed mean of M-values (TMM) method. Differential expression between groups was calculated with the exact test implemented in edgeR (Robinson M, McCarthy D, Smyth G (2010). Bioinformatics 26:139-140).

Pathway enrichment analyses was completed using Enrichr online and DAVID bioinformatics resource (Chen E, Tan C, Kou Y, Duan Q, Wang Z, Meirelles G, Clark N, Ma'ayan A (2013). BMC Bioinformatics 14:128; and Huang W, Sherman B, Lempicki R (2009) Systematic and integrative analysis of large gene lists using DAVID bioinformatics resources. Nature Protocols 4:44-57).

Data analysis. Data are reported as arithmetic means±SEM or SD as indicated. Confidence intervals (5-95%) and ranges were used to describe histopathological scores. ANOVA followed by Dunnett's test or the Bonnferoni correction was used for multiple comparisons with a control or among groups (Kusuoka H, Hoffman J (2002). Circ Res 91:662-671). At least six mice were planned to be available at each time point in each group, so that there would be sufficient power to detect a 20% change in lung hydroxyproline given an assumed coefficient of variance of 0.2. P≤0.05 was considered significant.

Results. Micro-CT scans. Mice treated with vehicle developed patchy infiltrative densities that persisted to day 28. Mice that received bleomycin plus MIA-602, the GHRH-R antagonist, appeared to have less prominent infiltrative densities in their lungs.

Figure 4:
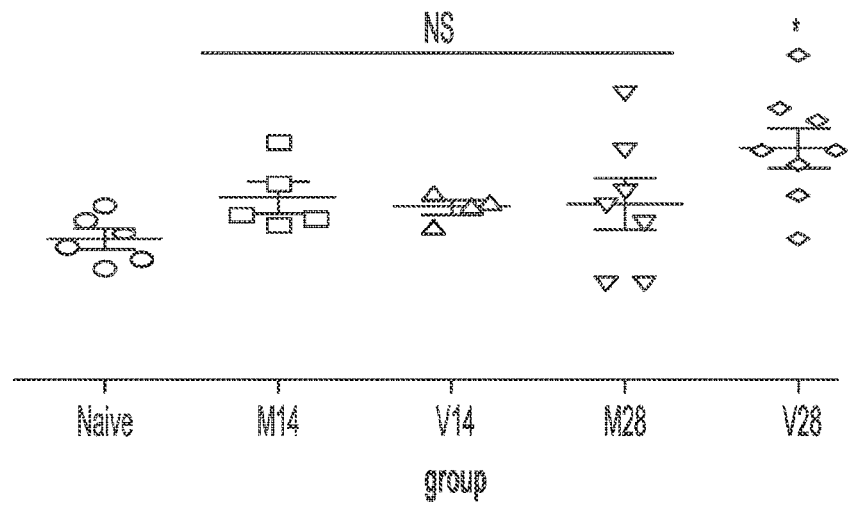
FIG. 4 shows lung hydroxyproline content. Evaluation of lung hydroxyproline (HP) content to estimate changes in collagen due to bleomycin and the effect of MIA-602. Data shown are mean hydroxyproline contents of right lungs±SEM at 14- and 28-day time points. Normal C57Bl/6J mice (n=6) had about 20 µg HP in the right lung. HP content increased significantly (*, P=0.0060 compared to Naive) after 28 days in mice treated with bleomycin and vehicle. No significant increase in HP content occurred in lungs of mice treated with bleomycin and the GHRH-R antagonist MIA-602. M14, MIA-602 group at 14 days (n=5); V14, vehicle group at 14 days (n=4); M28, MIA-602 group at 28 days (n=7); V28, vehicle group at 28 days (n=8).

Lung hydroxyproline contents. Lung HP content did not increase significantly after 14 days of intermittent treatment with bleomycin in mice receiving MIA-602 or vehicle. However, after 28 days, lung HP content increased significantly in bleomycin-treated mice that received vehicle, but not in bleomycin-treated mice that received MIA-602 on days 1-21. The data are summarized in FIG. 4.

Figure 5:
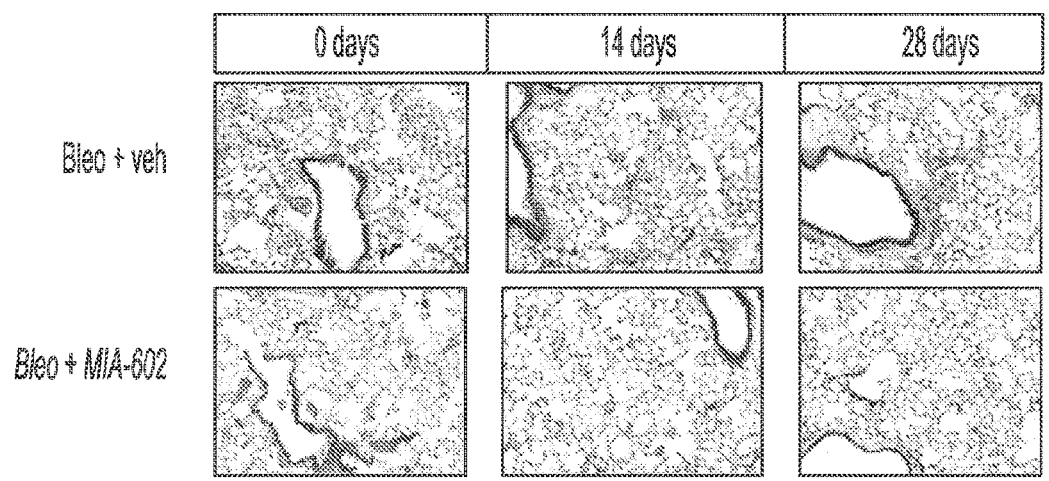
FIG. 5 shows lung histopathology. Mouse lungs were inflated with buffered formalin to 25 cm $H_2O$ pressure and fixed. Five µm sections were stained with Masson's trichrome stain and assessed semi-quantitatively for inflammation and fibrosis as described in the text. Fourteen days after bleomycin was started, cellular inflammation and early fibrosis was detected in lungs of mice treated with bleomycin and vehicle. Less inflammation appeared to be present in lungs of mice that received bleomycin and MIA-602 (middle panels). Twenty-eight days after bleomycin was started, increased fibrosis was evident in lungs of mice treated with bleomycin and vehicle. Less fibrosis appeared to be present in lungs of mice that received bleomycin and MIA-602, the growth hormone receptor antagonist.

Lung histopathology. After 14 days of intermittent bleomycin, inflammation and patchy, mild fibrosis were evident in mouse lungs. More fibrosis and fewer inflammatory cells were evident after 28 days. Both inflammatory changes and fibrosis were decreased in mice that received MIA-602 in addition to bleomycin. Representative examples are shown in FIG. 5.

MIA-602 appeared to reduce inflammation after 14 days in lungs of bleomycin-treated mice (0.4-1.4 [5%-95% CI]; range 0.6-1.2; n=4), compared to mice receiving vehicle (0.6-2.1; 0.8-1.9; n=4). MIA-602 appeared to reduce fibrosis after 28 days in lungs of bleomycin-treated mice that received MIA-602 (1.1-2.9; 1.0-3.0; n=5), but not in mice treated with vehicle (1.9-2.8; 1.5-2.9; n=8).

Lung fibroblast response to MIA-602. Lung fibroblasts were exposed to MIA-602 or vehicle in vitro for 24 hours before annexin-V/PI assay. MIA-602 caused predominantly cytolytic cell death (1 μM, 9.3±1.1%; 5 μM, 34.9±2.5%; P=0.0002) rather than apoptosis.

Figure 6A:
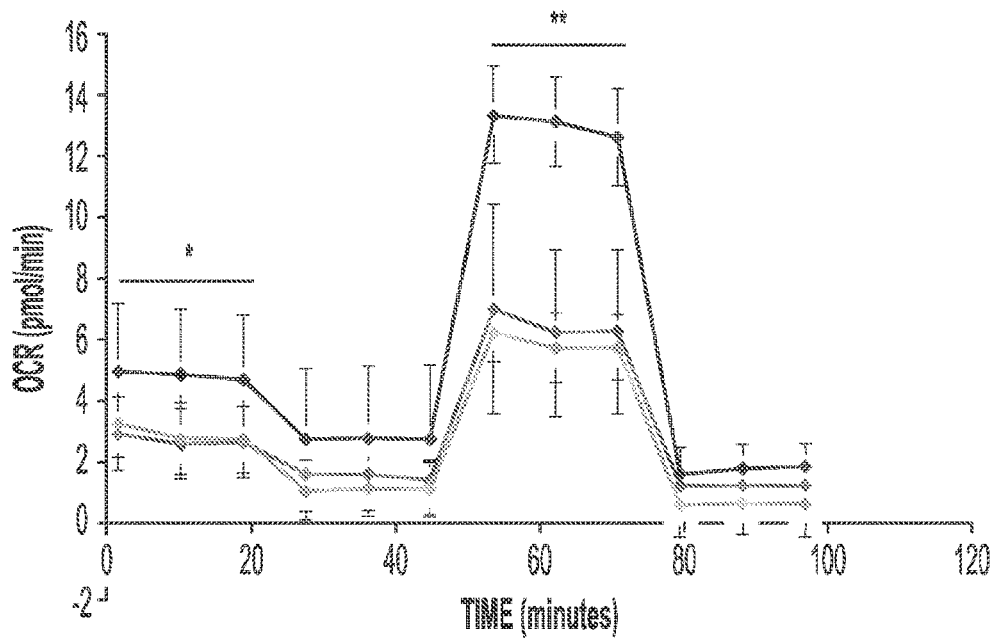
FIGS. 6A-B show that GRHR-R antagonist increases lung fibroblast basal and maximal oxygen consumption.
Figure 6B:
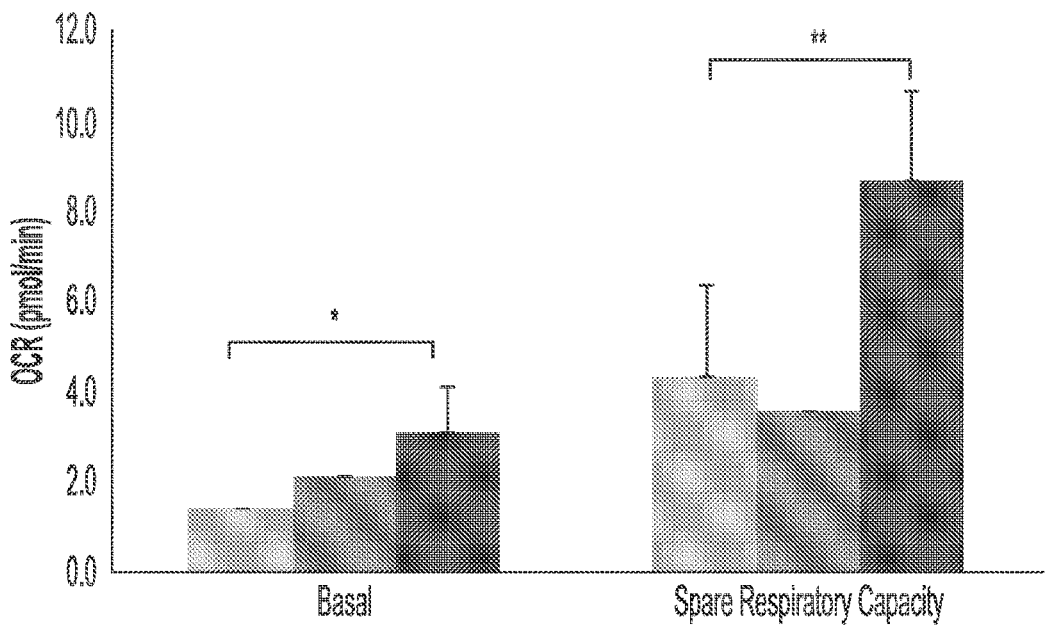

Cellular respiration. In vitro, MIA-602 at 5 μM concentration in complete medium increased fibroblast basal respiration and maximal respiration (after FCCP), compared to vehicle. Both 1 and 5 μM MIA-602 also appeared to increase non-mitochondrial respiration (after antimycin A and rotenone). These data are summarized in FIG. 6.

RNA-seq gene expression. The effects of MIA-602 or vehicle was explored on gene expression in lungs from mice treated in vivo with bleomycin for 28 days (data not shown). Several physiologically relevant genes were expressed differently after treatment with bleomycin (absolute fold change >1.5 and FDR<0.01). Specifically, after 28 days during which bleomycin was administered, genes related to the extracellular matrix, Wnt regulation and signaling, and the extracellular region were upregulated, consistent with known effects of bleomycin. Several relevant genes were found to be downregulated by bleomycin, including those related to lung morphogenesis and development, extracellular matrix organization, and alveolar septal development.

Figure 7A:
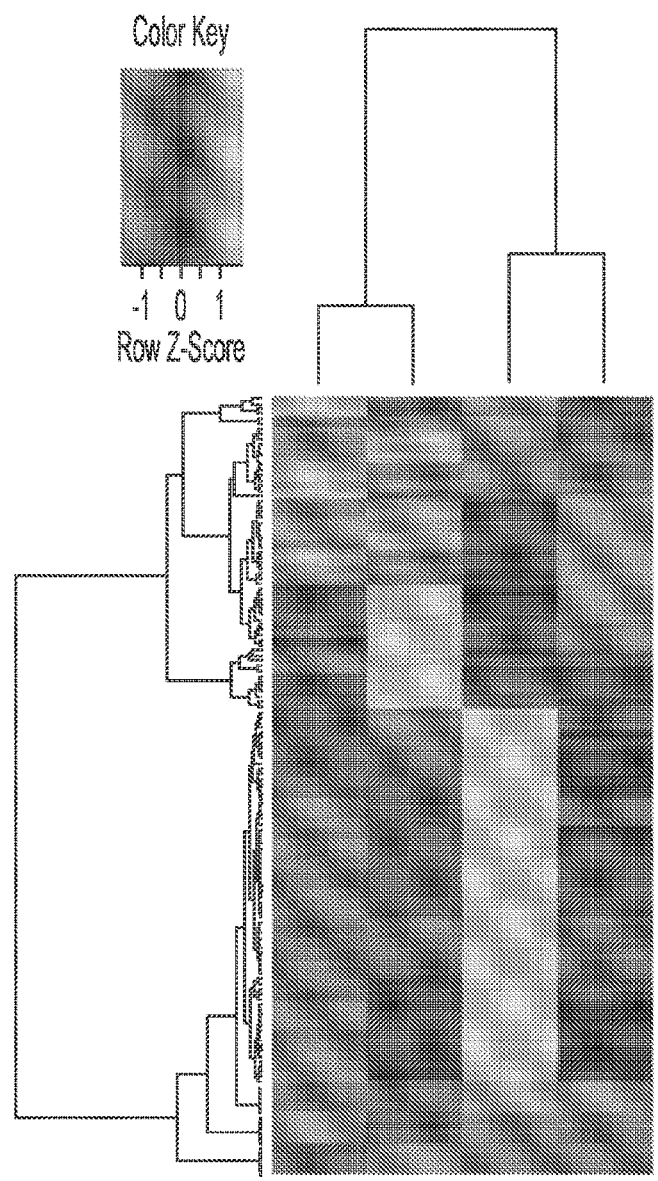
FIGS. 7A-B show transcriptomic analysis of mouse lung tissue RNA after treatment of mice in vivo with bleomycin and MIA-602 or vehicle.
Figure 7B:
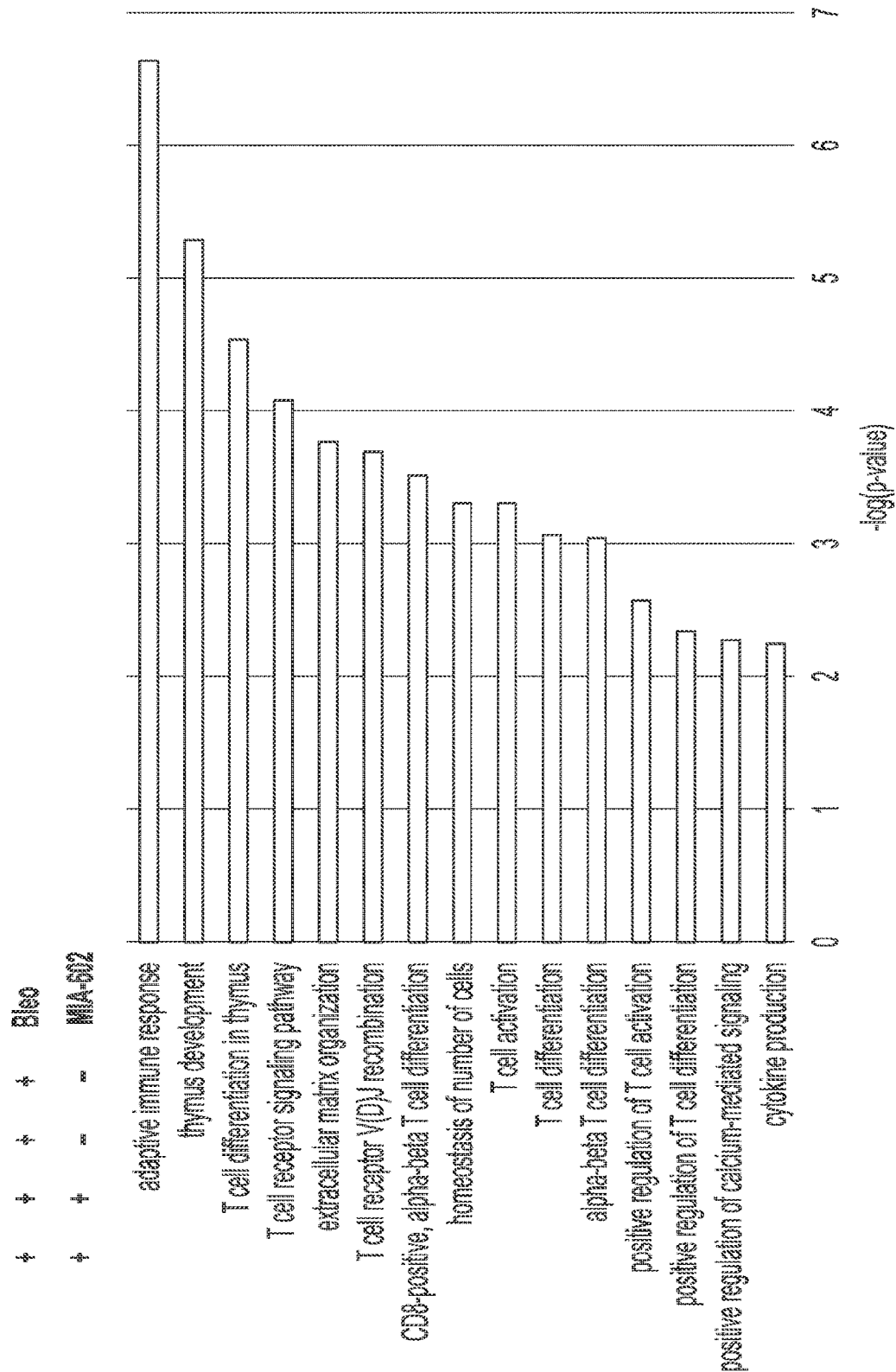
Figure 7B:
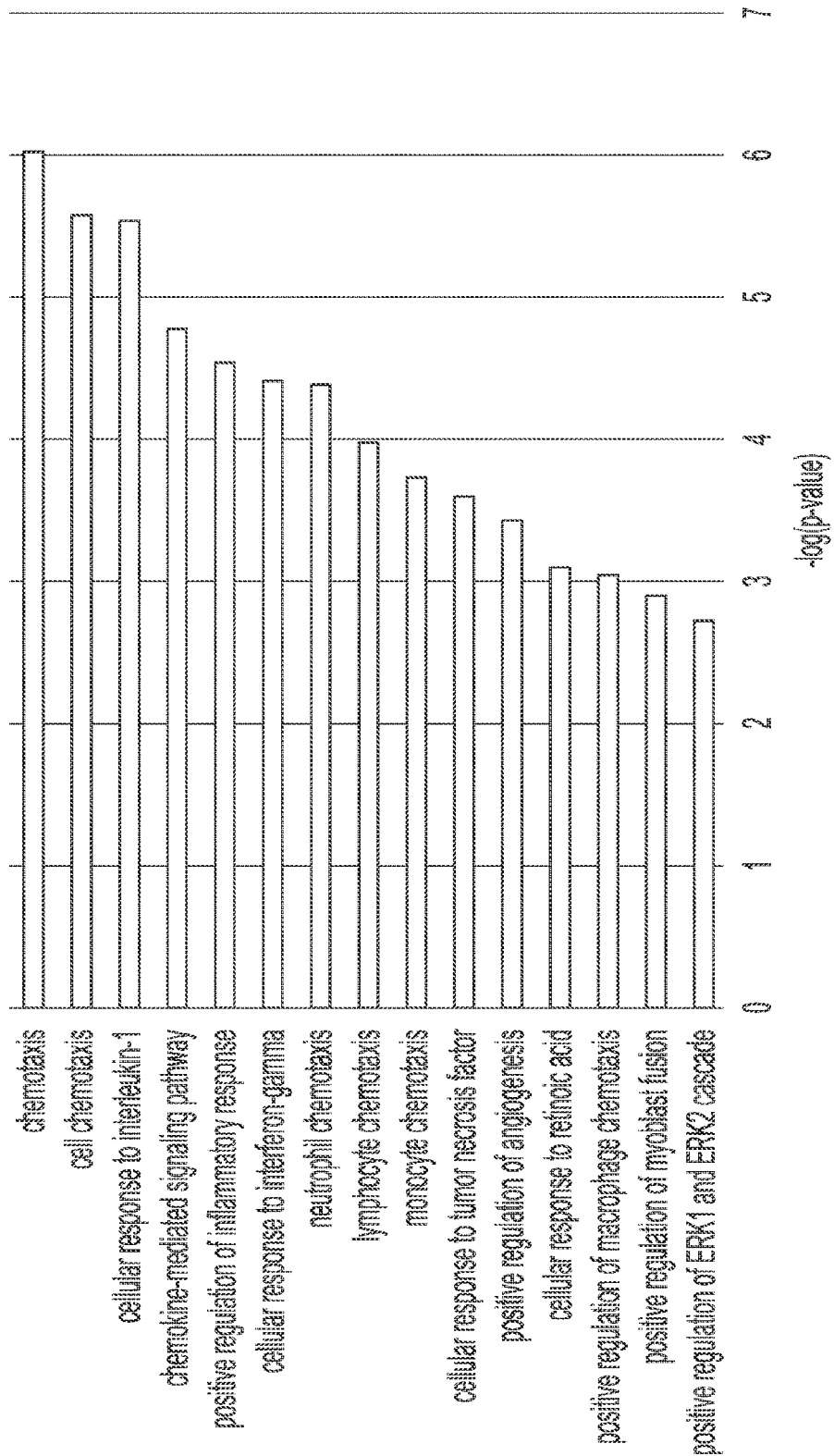

Transcriptome profiles then showed numerous genes expressed differently after treatment with MIA-602. Inversely modulated genes were highly enriched in pathways related to the adaptive immune response, T cell differentiation, T cell signaling, extracellular matrix organization, T cell activation and differentiation and cytokine production, consistent with the putative anti-inflammatory and anti-fibrotic effects of MIA-602. The ten most differentially expressed genes detected in lung tissue treated with MIA-602 compared to vehicle treatment are shown in Table 7. Those genes differentially expressed in fibrotic lungs from bleomycin-exposed mice treated with MIA-602 compared to vehicle are displayed as a heat map in FIG. 7.

TABLE 7

Clusters of the differentially expressed genes and their ontology between bleomycin-induced pulmonary fibrosis treated vs. untreated with MIA-602.

| Name | Gene list | P-value | Adjusted P-value |
|---|---|---|---|
| T cell differentiation (GO: 0030217) | CD4, CD8A, RAG2, RAG1 | 0.000003374 | 0.0007392 |
| T cell activation (GO: 0042110) | CD4, CD8A, CD3G, CD3E, LAT | 0.000003777 | 0.0007392 |
| T cell receptor signaling pathway (GO: 0050852) | PSMB11, CD4, THEMIS, CD3G, CD3E, LAT | 0.000004630 | 0.0007392 |
| Antigen receptor-mediated signaling pathway (GO: 0050851) | PSMB11, CD4, THEMIS, CD3E, LAT | 0.00006007 | 0.007193 |
| V(D) J recombination (GO: 0033151) | RAG2, RAG1 | 0.0001910 | 0.01829 |
| Enzyme linked receptor protein signaling pathway (GO: 0007167) | CD4, CD8A, NPPA, CD3A | 0.0002969 | 0.02370 |

TABLE 7-continued

Clusters of the differentially expressed genes and their ontology between bleomycin-induced pulmonary fibrosis treated vs. untreated with MIA-602.

| Name | Gene list | P-value | Adjusted P-value |
|---|---|---|---|
| T cell differentiation in thymus (GO: 0033077) | RAG2, RAG1 | 0.0004471 | 0.02677 |
| Regulation of leukocyte cell-cell adhesion (GO: 1903037) | CD4, LAT | 0.0004471 | 0.02677 |
| Regulation of lymphocyte activation (GO: 0051249) | CD4. LAT | 0.0006144 | 0.03270 |
| Lymphocyte differentiation (GO: 0030098) | CD4, RAG2, RAG1 | 0.0009974 | 0.04777 |

Similarly, the in vitro effects of 1 and 5 μM MIA-602 was directly tested on normal mouse lung fibroblasts (not exposed to bleomycin) and found significant downregulation of genes involved in collagen fibril organization, cell-matrix adhesion and elastic fiber assembly, consistent with the demonstrated anti-fibrotic effects of MIA-602. Upregulated fibroblast genes included those related to protein kinase activity, the JAK-STAT cascade, cell cycle and DNA replication including histones.

Discussion Pathophysiological GH secretion and IGF-1 activation have growth promoting effects in the lung resulting in increased alveolar size (Garcia-Rio F, Pino J, Diez J, Ruiz A, Villasante C, Villamor J (2001). Am J Respir Crit Care Med 164:852-857). IGF-1 itself increases α-smooth muscle actin in lung fibroblasts and promotes a myofibroblast phenotype. The pituitary type GHRH receptor is present in both normal and IPF lung tissue (Jackson R, Ai L, Zhang C, Zhang X, Delcroix G, Lazerson A, Mirsaeidi M, Schally A (2018). European Respiratory Journal 52 (suppl 62): OA5349), suggesting that local secretion of GH may occur physiologically and have direct effects on lung tissue.

MIA-602 partially inhibits both lung inflammation and fibrosis, assessed histopathologically and biochemically, after intraperitoneal bleomycin. RNA-seq data, importantly, show suppression of the adaptive immune response, T cell differentiation and activation and cytokine production by MIA-602 in bleomycin-treated mouse lungs. The effects of the GHRH-R antagonist observed have implications for fibrosing lung diseases in humans, and they could, importantly, reveal novel pathways amenable to clinical drug development (Jenkins R, Moore B, Chambers R, Eickelberg O, Königshoff M, Kolb M, Laurent G J, Nanthakumar C B, Olman M, Pardo A, Selman M, Sheppard D, Sime P, Tager A, Tatler A, Thannickal V, White E (2017). Am J Respir Cell Mol Biol 56:667-679).

Initially, development of lung infiltrates due to bleomycin was confirmed with micro CT scans, inflammation and fibrosis with histopathological examination, and increased collagen with biochemical assays. Similar models have been used successfully in the development of antifibrotic drugs, including pirfenidone and nintedanib.

Senescent fibroblasts that display respiratory abnormalities, indicating mitochondrial damage, express both STAT3 and p21 as markers of the senescent phenotype (Waters D, Blokland K, Pathinayake P, Wei, Schuliga M, Jaffar J, Hansbro P, Prele C, Mutsaeres S, Bartlett N, Grainge C, Knight D (2019). Am J Resp Cell Molec Biol 10.1165/ rcmb.2018-0328OC). MIA-602 downregulates p21 activated kinase and STAT3 and NFκB in gastric cancer cells (Gan J, Ke X, Jiang J, Dong H, Yao Z, Lin Y, Lin W, Wu X, Yan S, Zhuang Y, Chu W, Cai R, Zhang X, Cheung H, Block N, Pang C, Schally A, Zhang H (2016). Proc Natl Acad Sci USA 113:14745-14750). GHRH antagonists like MIA-602 could modulate the senescent phenotype leading to fibrosis, and conceivably be one of the mechanisms that lessens the fibrotic response in this model.

In vitro, MIA-602 at micromolar concentrations increased basal and maximal mitochondrial respiration, and it resulted in marked cytolytic death of mouse lung fibroblasts. Mitochondrial dysfunction and loss of apoptotic potential occur in fibroblasts from IPF lungs, and enhancement of mitochondrial function itself by MIA-602 at lower concentrations in vivo might modulate fibrosis by maintaining the capacity for mitophagy and apoptosis (Ryter S, Rosas I, Owen C, Martinez F, Choi M, Lee C, Elias J, Choi A. (2018). Ann Am Thorac Soc 15(Suppl 4):5266-5272).

GHRH-R antagonists decrease lipid peroxidation, protein carbonyls and nitrotyrosine in prostate cancer cells (Rekasi Z, Varga J, Schally A, Halmos G, Armatis P, Groot K, Czompoly T (2001). Endocrinology 141:2120-2128), indicating antioxidant effects that would augment their other anti-inflammatory effects (Ren J, Yu Q, Ma D, Liang W, Leung P, Ng T, Chu W, Schally A, Pang C, Chan S (2019). Exp Eye Res 181:277-284). Both GH and IGF-1 stimulate neutrophil superoxide (O2−) production (Schally A, Varga J, Engel J (2007). Nature Clin Pract Endo Metab 4:33-43). Since GHRH-R antagonists inhibit GH secretion and IGF-1 activation (Fu Y, Arkins S, Wang B, Kelley K. J Immunol 146:1602-1608, 1991), it could be predicted that they would inhibit both O2− and hydrogen peroxide ($H_2O_2$) release during the inflammatory phase of injury (Warwick-Davies J, Lowrie D, Cole P (1995). J Immunol 154:1909-1918). Cellular levels of oxidant stress are decreased by MIA-602, and its antioxidant effect would limit redox signaling in response to receptor ligation (Barbutis N, Schally A (2008). PNAS 105:20470-20475).

MIA-602 disrupts the PI3/AKT pathway in several experimental systems. PI3K/AKT signaling is involved in the pathogenesis of bleomycin-induced fibrosis (Kral J, Kuttke M, Schrottmaier W, Birnecker B, Warszawska J, Wernig C, Paar H, Salzmann M, Sahin E, Brunner J S, Österreicher C, Knapp S, Assinger A, Schabbauer G (2016). Sci Rep 6:23034 doi: 10.1038/srep23034), and suppression of the PI3K/AKT pathway by GHRH antagonist could also lessen lung fibrosis. GHRH clearly appears involved in the lung's response to treatment with bleomycin and subsequent healing.

Genes related to the extracellular matrix and the Wnt pathway were over expressed in fibrotic lungs from mice treated with bleomycin, compared gene expression in naïve controls (Cabrera S, Selman M, Lonzano-Bolanos A, Konishi K, Richards T, Kaminski N, Pardo A (2013). Am J Physiol Lung Cell Molec Physiol 304:L593-L601). In contrast, genes related to epithelial tube branching, lung morphogenesis and lung development were under expressed after bleomycin and development of fibrosis. Genes related the immune response, cellular adhesion and remodeling, and T cell signaling were also found to be upregulated in lungs from rats treated with TGF-β (Huang X, Li L, Ammor R, Zhang Y, Wang Y, Ravi K, Thompson J, Jarai G (2019). Am J Physiol Lung Cell Molec Physiol 316:L348-L357).

T cells play an important role in the lungs of patients with pulmonary fibrosis (Simonian P, Roark C, Diaz del Valle F, Palmer B, Douglas I S, Ikuta K, Born W, O'Brien R, Fontenot A (2006). J Immunol 177:4436). T-cell receptors and costimulatory molecules are required for activation of T-cells and in development of inflammation driven lung fibrosis (Elhai M, Avouac J, Hoffmann-Vold A, Ruzehaji N, Amiar O, Ruiz B, Brahiti H, Ponsoye M, Fréchet M, Burgevin A, Pezet S, Sadoine J, Guilbert T, Nicco C, Akiba H, Heissmeyer V, Subramaniam A, Resnick R, Molberg Ø, Kahan A, Chiocchia G, Allanore Y (2016). Proc Natl Acad Sci USA 113:E3901-10). It was found that downregulation of T cell receptor complex genes (CD3E, CD3G, CD4, and CD8A) had the highest associations in pathway analyses. MIA-602 may thus play an important role in lung tissue by modification of T-cell signaling and potentially reducing inflammation and fibrosis.

These data show that GHRH-R is present in human lungs; and, in a relevant in vivo model, lung fibrosis is modulated by its inhibition. Functional findings implicate GHRH and GH in fibrosing lung disease, and they are consistent with demonstrated effects of the GHRH-R antagonist on mitochondrial respiration and fibroblast cytotoxicity. MIA-602 inhibits intracellular signaling pathways, including p21 activated kinase/STAT3/NFκB and PI3K/AKT, in addition to having intrinsic antioxidant activity. Further, it could support mitochondrial function and maintain autophagy, minimizing fibrosis.

What is claimed is:

1. A method of reducing lung inflammation, the method comprising:
   administering to a subject with pulmonary fibrosis a therapeutically effective amount of a growth hormone releasing hormone (GHRH) receptor antagonist, wherein the GHRH receptor antagonist is a peptide comprising the amino acid sequence: PhAC-Ada-Tyr D-Arg Asp Ala Ile 5FPhe Thr Ala Har Tyr(Me) His Orn Val Leu Abu Gln Leu Ser Ala His Orn Leu Leu Gln Asp Ile Nle D-Arg Har-NH$_2$.

2. A method of reducing lung scarring, the method comprising:
   administering to a subject with pulmonary fibrosis a therapeutically effective amount of a growth hormone releasing hormone (GHRH) antagonist, wherein the GHRH receptor antagonist is a peptide comprising the amino acid sequence: PhAC-Ada-Tyr D-Arg Asp Ala Ile 5FPhe Thr Ala Har Tyr(Me) His Orn Val Leu Abu Gln Leu Ser Ala His Orn Leu Leu Gln Asp Ile Nle D-Arg Har-NH$_2$.

3. A method of ameliorating one or more symptoms of pulmonary fibrosis, the method comprising: administering to a subject with pulmonary fibrosis a therapeutically effective amount of a growth hormone releasing hormone (GHRH) antagonist, wherein the GHRH receptor antagonist is a peptide comprising the amino acid sequence: PhAC-Ada-Tyr D-Arg Asp Ala Ile 5FPhe Thr Ala Har Tyr(Me) His Orn Val Leu Abu Gln Leu Ser Ala His Orn Leu Leu Gln Asp Ile Nle D-Arg Har-NH$_2$.

4. The method of claim 3, wherein the one or more symptoms of pulmonary fibrosis is breathlessness, cough, decreased exercise tolerance, hypoxemia or a combination thereof.

\* \* \* \* \*